(12) United States Patent
Miller et al.

(10) Patent No.: US 7,407,976 B2
(45) Date of Patent: Aug. 5, 2008

(54) THIAZOLES AND OXAZOLES USEFUL AS MODULATORS OF ATP-BINDING CASSETTE TRANSPORTERS

(75) Inventors: Mark T. Miller, San Diego, CA (US); Sarah S. Hadida Ruah, La Jolla, CA (US); Peter D. J. Grootenhuis, San Diego, CA (US); Matthew Hamilton, Hackettstown, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 124 days.

(21) Appl. No.: 10/989,218

(22) Filed: Nov. 15, 2004

(65) Prior Publication Data

US 2005/0130970 A1    Jun. 16, 2005

Related U.S. Application Data

(60) Provisional application No. 60/520,355, filed on Nov. 14, 2003.

(51) Int. Cl.
*C07D 277/28* (2006.01)
*C07D 417/12* (2006.01)
*C07D 401/12* (2006.01)
*A61K 31/4725* (2006.01)
*A61K 31/427* (2006.01)

(52) U.S. Cl. .............. 514/365; 514/236.8; 514/255.05; 514/307; 514/326; 514/363; 514/364; 544/133; 544/180; 544/405; 546/146; 546/209; 546/269.7; 548/127; 548/128; 548/131; 548/134; 548/200

(58) Field of Classification Search .................. None
See application file for complete search history.

(56) References Cited

U.S. PATENT DOCUMENTS 6,251,629 B1 * 6/2001 Warren ..................... 435/69.1
6,329,403 B1 * 12/2001 Odaka et al. .............. 514/342
6,479,231 B1 * 11/2002 Cihlar ........................ 435/4
6,630,482 B1 10/2003 Becq et al. ................ 514/294

FOREIGN PATENT DOCUMENTS

| DE | 102 50 110 | 5/2004 |
|---|---|---|
| EP | 0 652 229 | 5/1995 |
| GB | 1 318 291 | 5/1973 |
| JP | 10338680 | * 12/1998 |
| WO | WO 2004/084842 | 10/2004 |

OTHER PUBLICATIONS

Tanaka et al., "A Facile Synthesis of 2-exo-Methylenepenam Through Reductive Cyclization of Allenecarboxylates in a Metal Salt/Metal Bimetal Redox System", Synlett, vol. 11, pp. 878-880 (1992).*
Sako et al., "Thermal reaction of 4-benzothiazolyldithioazetidinone novel formation of isothiazolone derivatives," Chemical & Pharm. Bulletin, vol. 26, Issue 4, pp. 1236-1239 (1978).*
Tanaka et al., STN International, HCAPLUS Database, Columbus, OH, Accession No. 1993:101688, Reg. Nos. 145603-23-2 and 145887-60-1 (2006).*
Sako et al., STN International, HCAPLUS Database, Columbus, OH, Accession No. 1978:443215, Reg. No. 67004-94-8 (2006).*
Hahn, Hoh-Gyu et al., "Synthesis of new trifluoromethylated 1,3-oxazolecarboxanilides and their fungicidal activities", Agricultural Chemistry and Biotechnology (English Edition),45(1), pp. 37-42, 2002.

* cited by examiner

*Primary Examiner*—Kamal A. Saeed
*Assistant Examiner*—Andrew B. Freistein
(74) *Attorney, Agent, or Firm*—Michael DiVerdi

(57) ABSTRACT

The present invention relates to modulators of ATP-Binding Cassette ("ABC") transporters or fragments thereof, including Cystic Fibrosis Transmembrane Regulator ("CFTR"), compositions thereof, and methods therewith. The present invention also relates to methods of treating ABC transporter mediated diseases using such modulators.

15 Claims, No Drawings

THIAZOLES AND OXAZOLES USEFUL AS MODULATORS OF ATP-BINDING CASSETTE TRANSPORTERS

CROSS-REFERENCE TO RELATED APPLICATIONS

The present application claims priority under 35 U.S.C. § 119 to U.S. Provisional application No. 60/520,355, entitled "THIAZOLES AND OXAZOLES USEFUL AS MODULATORS OF ATP-BINDING CASSETTE TRANSPORTERS", filed Nov. 14, 2003, the entire contents of that application being incorporated herein by reference.

TECHNICAL FIELD OF THE INVENTION

The present invention relates to modulators of ATP-Binding Cassette ("ABC") transporters or fragments thereof, including cystic fibrosis transmembrane conductance regulator ("CFTR"), compositions thereof, and methods therewith. The present invention also relates to methods of treating ABC transporter mediated diseases using such modulators.

BACKGROUND OF THE INVENTION

ABC transporters are a group of membrane transporter proteins that play a major role in the transport and protection of cells against a wide variety of pharmacological agents, potentially toxic drugs, and xenobiotics. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. Up until the present time, 48 human ABC transporters have been identified, and these have been arranged into 7 families based on their sequence identity and function.

ABC transporters play a variety of important physiological roles within the body, as well as providing a defense against harmful compounds from the environment. Moreover they represent important potential drug targets both in their own right, as well as, because in many cases therapeutic drugs are also transported out of the target cell by these molecules.

One of the members of the ABC transporter family, namely, CFFR, is believed be the chloride channel responsible for cAMP-mediated chloride secretion in epithelial cells, and to play a key role in the secretion of chloride and maintenance of normal electrolyte transport throughout the body. CFTR is a protein of approximately 1480 amino acids made up of two repeated elements, each comprising six transmembrane segments and a nucleotide-binding domain. The two repeats are separated by a large, polar, regulatory (R)-domain containing multiple potential phosphorylation sites.

The gene associated with CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene leads to cystic fibrosis (hereinafter "CF"), the most common fatal genetic disease in humans affecting approximately one in every 2,500 infants born in the United States. Within the general United States population, up to 10 million people carry a single copy of the defective gene without apparent ill effects. In contrast, individuals with two copies of the CF associated gene suffer from the chronic effects of CF, including chronic lung destruction and death.

In patients with CF, expression of the CF associated gene in airway cells, leads to reduced cellular apical chloride conductance causing an imbalance in ion and fluid transport. It is widely believed that this leads to the abnormal mucus secretion in pancreatic ductules and in the airways that ultimately results in the pulmonary infections and epithelial cell damage typically associated with disease progression in CF. In addition to respiratory problems, CF patients typically suffer from gastrointestinal problems, and pancreatic insufficiency. Males are almost uniformly infertile and fertility is decreased in females. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). At present, more than 1000 mutations in the CF gene have been identified (http://www.genet.sickkids.on.ca/cftr/), but population studies have indicated that the most common CF mutation, a deletion of the 3 nucleotides that encode phenylalanine at position 508 of the CFTR amino acid sequence, is associated with approximately 70% of the cases of cystic fibrosis. The mutated CFTR protein is referred to as $\Delta F508$.

It is believed that the deletion of residue 508 in $\Delta F508$-CFTR prevents the nascent protein from folding correctly, resulting in the inability of this mutant protein to exit the endoplasmic reticulum (hereinafter "ER"), and traffic to the plasma membrane. As a result, insufficient amounts of the mature protein are present at the plasma membrane and chloride transport within epithelial tissues is significantly reduced (Quinton, P. M. (1990), FASEB J. 4: 2709-2727). Hence, the cellular phenomenon of defective ER processing of other proteins like CFTR, by the ER machinery, has been shown to be the underlying basis for a wide range of isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. Studies have shown, however, that $\Delta F508$-CFTR, when presented at the plasma membrane is functional as a cAMP-responsive $Cl^-$ channel (Dalemans et al. (1991), Nature Lond. 354: 526-528; Denning et al., supra.; Pasyk and Foskett (1995), J. Cell. Biochem. 270: 12347-50).

Although CFTR transports a variety of molecules in addition to anions, this role of transporting anions represents an important element in the overall cellular machinery for transporting ions and water across the epithelium. The other elements include the epithelial $Na^+$ channel, ENaC, $Na^+/2Cl^-/K^+$ co-transporter, $Na^+$-$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of: (i) ENaC and CFTR present on the apical membrane; and (ii) the $Na^+$-$K^+$-ATPase pump and Cl-channels expressed on the basolateral surface of the cell.

Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to CF, modulation of CFTR activity may be beneficial for other diseases not directly caused by mutations in CFTR, such as secretory diseases and other protein folding diseases mediated by CFTR. These include, but are not limited to, chronic obstructive pulmonary disease (hereinafter "COPD"), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and to a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as CF and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms include dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

The diseases associated with the first class of ER malfunction are CF (due to misfolded ΔF508-CFTR), hereditary emphysema (due to α1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to Vasopressin hormone/V2-receptor), neprogenic DI (due to aquaporin II), Charcot-Marie Tooth syndrome (due to Peripheral myelin protein 22), Perlizaeus-Merzbacher disease, neurodegenerative diseases such as Alzheimer's disease (due to PAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as Spongiform encephalopathies, such as hereditary Creutzfeldt-Jakob disease (due to Prion protein processing defect), Fabry disease (due to lysosomal α-galactosidase A) and Straussler-Scheinker syndrome (due to Prp processing defect).

In CF, chloride transport mediated by the CFFR is reduced resulting in the abnormal mucus secretion that characterizes the disease. By contrast in secretory diarrheas epithelial water transport is dramatically increased as a result of secretagogue activated chloride transport. The mechanism involves elevation of cAMP and stimulation of CFFR.

Although there are numerous causes of diarrhea, the major consequences of diarrheal diseases, resulting from excessive chloride transport are common to all, and include dehydration, acidosis, death and impaired growth.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

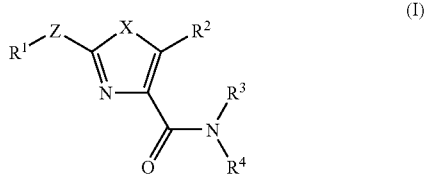

or a pharmaceutically acceptable salt thereof, wherein X, Z, $R^1$, $R^2$, $R^3$, and $R^4$ are described generally and in classes and subclasses below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

DETAILED DESCRIPTION OF THE INVENTION

I. General Description of Compounds of the Invention:

The present invention relates to compounds of formula I useful as modulators of ABC transporter activity:

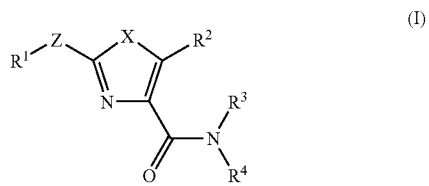

or a pharmaceutically acceptable salt thereof, wherein X is O or S;

Z is a bond or is an optionally substituted $C_{1-4}$alkylidene chain, wherein up to two methylene units of the chain are optionally and independently replaced by —NR—, —S—, —O—, —SO$_2$NR— —NRSO$_2$—, —SO$_2$—, or —CO—;

$R^1$ is hydrogen, or is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein $R^1$ is optionally substituted at one or more carbon or nitrogen atoms with x independent occurrences of —QR$^x$; wherein x is 0-5; wherein Q is a bond or is a $C_1$-$C_6$ alkylidene chain wherein up to two methylene units of Q are optionally and independently replaced by —CO—, —CO$_2$—, —COCO—, —CONR—, —OCONR—, —NRNR—, —NRNRCO—, —NRCO—, —NRCO$_2$—, —NR-CONR—, —SO—, —SO$_2$—, —NRSO$_2$—, —SO$_2$NR—, —NRSO$_2$NR—, —O—, —S—; or —NR—; and each occurrence of R$^x$ is independently R', halogen, NO$_2$, or CN,or —QR$^x$ is =O, =S, or =NR';

each occurrence of R is independently hydrogen or an optionally substituted $C_{1-6}$ aliphatic group; and each occurrence of R is independently hydrogen or an optionally substituted $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R, are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

$R^2$ is halogen, —CN, —CF$_3$, —NO$_2$, or —T$_q$R;

$R^3$ is $U_mR^1$ and $R^4$ is $V_pCy^1$, wherein m, p, and q are each independently 0 or 1, and U, V, and T are each independently an optionally substituted $C_1$-$C_4$alkylidene chain, wherein up to two methylene units of the chain are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—;

$Cy^1$ is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein $Cy^1$ is optionally substituted at one or more carbon or nitrogen atoms with y independent occurrences of —WR$^W$; wherein y is 0-5; wherein W is a bond or is a $C_1$-$C_6$ alkylidene chain wherein up to two methylene units of W are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and each occurrence of R$^W$ is independently R', halogen, NO$_2$, or CN, or —WR$^W$ is =O, =S, or =NR'; or $R^3$ and $R^4$, taken together with the nitrogen atom to which they are bound form an optionally substituted 5-, 6- or 7-membered saturated, partially unsaturated or fully unsaturated ring having the structure:

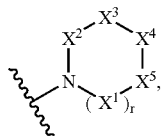

wherein r is 0, 1, or 2; one of $X^3$, $X^4$, or $X^5$ is CH—$V^p$-Cy$^1$ or N—$V_p$-Cy$^1$, and the others of $X^3$, $X^4$, or $X^5$ are CHR' or NR'; and each occurrence of $X^1$, when present, and $X^2$ are each independently C(R')$_2$, —CO—, or —CS—.

In some embodiments, for compounds of formula I as described generally above:

a) when X is S, Z is CH$_2$, and $R^2$ is hydrogen, then $R^1$ is not:

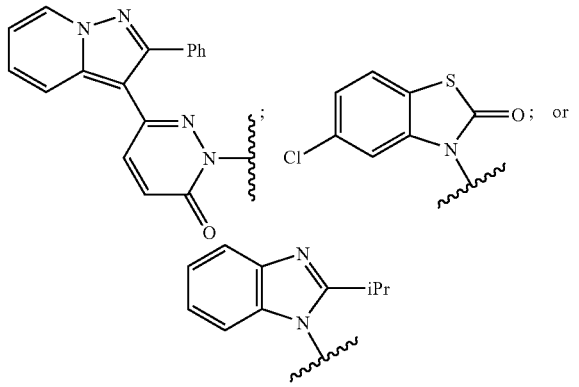

b) when X is S or O; and $R^2$ is formyl, 4,5-dihydro-2-oxazolyl, —COOR', or —COSR'; then:
  i) when Z is —CH$_2$—, $R^1$ is not phenyl optionally substituted with $C_1$-$C_4$alkyl, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, halogen, cyano, or nitro; or
  ii) when Z is $C_{1-6}$alkyl, then $R^1$ is not $C_3$-$C_6$cycloalkyl optionally substituted with $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, halogen, cyano, or nitro;

c) when X is S, $R^2$ is H, Z is —CH$_2$—, and $R^1$ is unsubstituted phenyl, then when $R^3$ is hydrogen, $R^4$ is not:

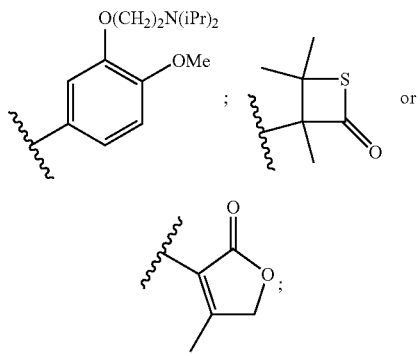

d) when X is S, $R^2$ is SMe or Me, Z is CH$_2$ and $R^1$ is unsubstituted phenyl,
  i) when $R^3$ is hydrogen, then $R^4$ is not unsubstituted benzyl; and
  ii) when $R^3$ is ethyl, then $R^4$ is not unsubstituted phenyl;

e) when X is O, Z is CH$_2$, $R^1$ is unsubstituted phenyl, $R^2$ is Me, and $R^3$ is hydrogen, then $R^4$ is not

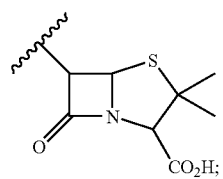

f) when X is O, Z is CH$_2$, $R^1$ is unsubstituted phenyl, $R^2$ is hydrogen, and $R^3$ is hydrogen, then $R^4$ is not unsubstituted phenyl, 4-Me-phenyl, or unsubstituted benzyl; and g) when X is O, Z is —CH($_i$Pr)—, $R^1$ is

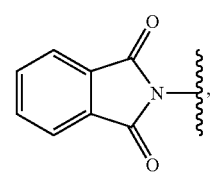

and $R^3$ is hydrogen, then $R^4$ is not —(CH$_2$)$_2$—S-Phenyl;

h) when Z-R$^1$ is methyl, X is S, R$^3$ is iBu, then R$^4$ is not:

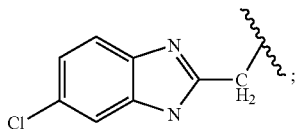

and i) when Z-R$^1$ is phenyl, X is S, and R$_3$ is —(CH$_2$)$_2$-pyrid-2-yl, then R$^4$ is not

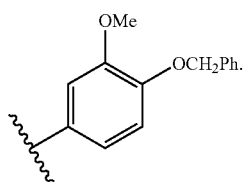

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture, light, or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —P(O)$_2$R°; —PO(R°)$_2$; —OPO(R°)$_2$; —(CH$_2$)$_{0-2}$NHC(O)R°; phenyl (Ph) optionally substituted with R°; —O(Ph) optionally substituted with R°; —(CH$_2$)$_{1-2}$(Ph), optionally substituted with R°; or —CH=CH(Ph), optionally substituted with R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or halo C$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R$^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R$^+$, R, R' or any other variable similarly defined herein), are taken together with the atom(s) to which each variable is bound include, but are not limited to the following: a) two independent occurrences of R° (or R$^+$, R, R' or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, R, R' or any other variable similarly defined herein) that are bound to different atoms and are taken together with both of those atoms to form a ring, for example where a phenyl group is substituted with two occurrences of

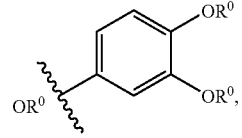

these two occurrences of R° are taken together with the oxygen atoms to which they are bound to form a fused 6-membered oxygen containing ring:

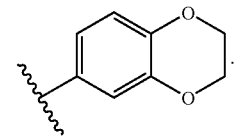

It will be appreciated that a variety of other rings can be formed when two independent occurrences of R° (or R$^+$, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

3. Description of Exemplary Compounds:

As described generally above, for compounds of the invention, X is O or S and compounds of formula I-A or I-B are provided:

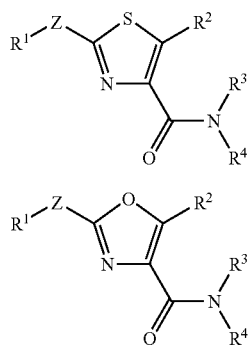

I-A

I-B

As described generally above, Z is a bond or an optionally substituted $C_{1-4}$alkylidene chain, wherein up to two methylene units of the chain are optionally and independently replaced by —NR—, —S—, —O—, or —CO—. In certain exemplary embodiments, Z is —[C(R$^5$)$_2$]$_n$—, wherein n is 0, 1, 2, or 3, and each occurrence of R$^5$ is independently halogen, CN, NO$_2$, or —YR, wherein Y is a bond or is an optionally substituted $C_1$-$C_4$ alkylidene chain wherein up to two methylene units of Y are optionally and independently replaced by —O—, —NR—, —CO—, —S—, —SO—, or —SO$_2$—. In other exemplary embodiments Z is —[C(R$^5$)$_2$]$_n$O—, wherein n is 0, 1, 2, or 3, and each occurrence of R$^5$ is independently halogen, CN, NO$_2$, or —YR, wherein Y is a bond or is an optionally substituted $C_1$-$C_4$ alkylidene chain wherein up to two methylene units of Y are optionally and independently replaced by —O—, —NR—, —CO—, —S—, —SO—, or —SO$_2$—. In still other exemplary embodiments Z is —[C(R$^5$)$_2$]$_n$S—, wherein n is 1, 2, or 3, and each occurrence of R$^5$ is independently halogen, CN, NO$_2$, or —YR, wherein Y is a bond or is an optionally substituted $C_1$-$C_4$ alkylidene chain wherein up to two methylene units of Y are optionally and independently replaced by —O—, —NR—, —CO—, —S—, —SO—, or —SO$_2$—.

In certain other embodiments, Z is a bond. In yet other embodiments, Z is —C(R$^5$)$_2$—.

In certain embodiments, Z is —CH$_2$— or —CH$_2$—CH$_2$—. In some embodiments, Z is —CH$_2$—.

As described generally above, R$^1$ is hydrogen, or is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R$^1$ is optionally substituted at one or more carbon atoms with x independent occurrences of —QR$^x$; wherein x is 0-5. In some embodiments R$^1$ is hydrogen. In other embodiments R$^1$ is selected from one of the following groups:

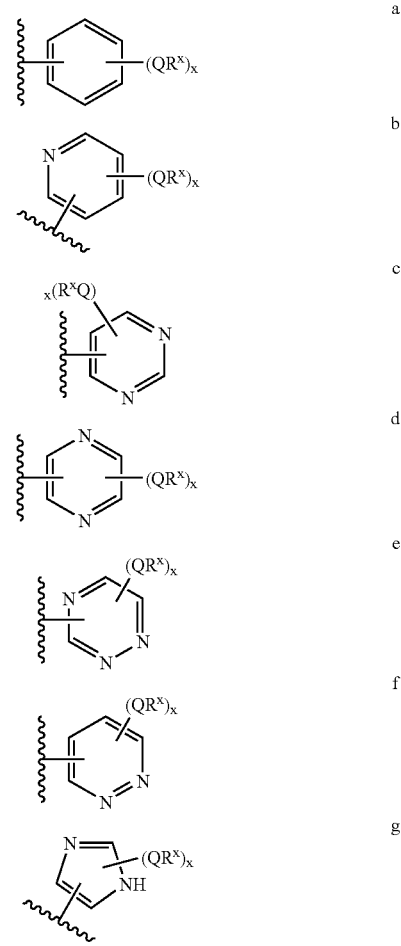

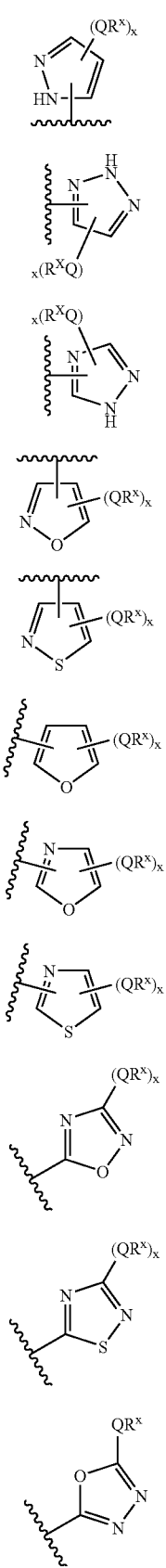
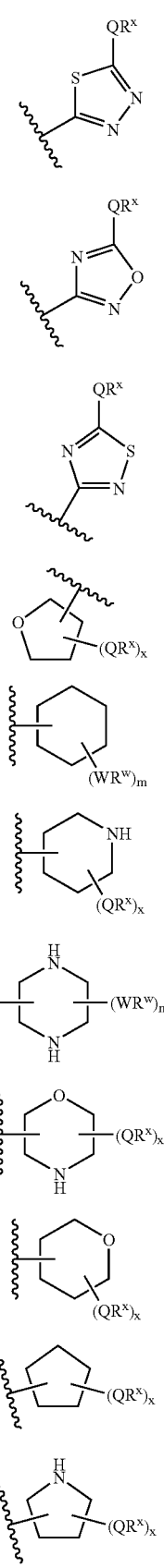

-continued

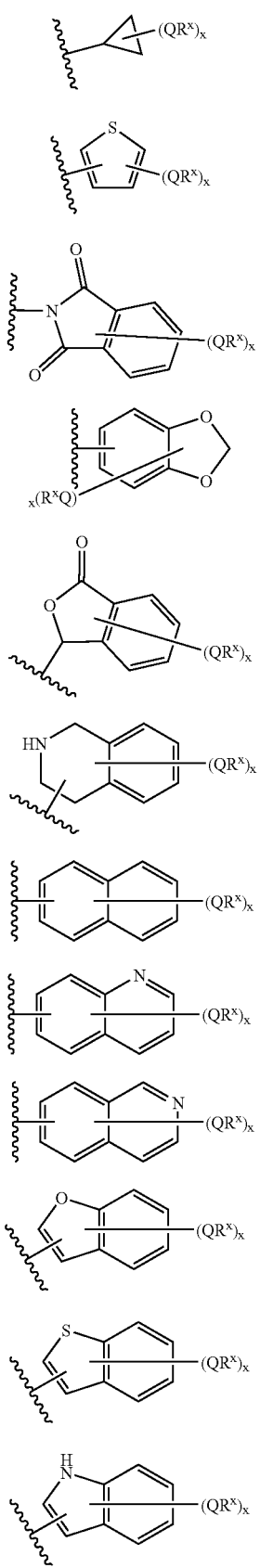

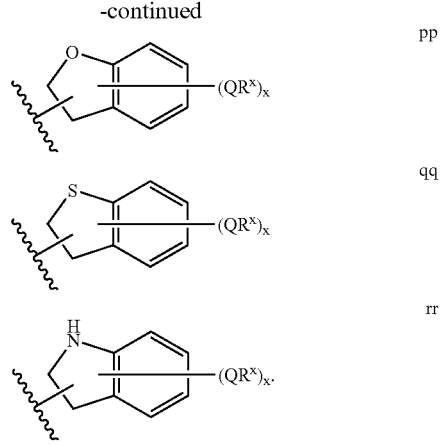

In some embodiments $R^1$ is one of rings a, b, c, d, m, n, o, ee, gg, or pp. In other embodiments $R^1$ is ring a. In certain other embodiments, $R^1$ is ring gg.

It will be appreciated that, as described generally above, $R^1$ is optionally substituted at one or more carbon or nitrogen atoms with x independent occurrences of $-QR^X$; wherein x is 0-5; wherein Q is a bond or is a $C_1$-$C_6$ alkylidene chain wherein up to two methylene units of Q are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and each occurrence of $R^X$ is independently R', halogen, NO$_2$, or CN, or —QR$^X$ is =O, =S, or =NR'. In certain embodiments, x is 0, 1, 2 or 3, and Q is a bond or is an optionally substituted $C_1$-$C_6$ alkylidene chain wherein one or two methylene units are optionally and independently replaced by O, NR, S, SO$_2$, or CO$_2$, CO, and $R^X$ is R' or halogen. In other embodiments, x is 0, 1, 2, or 3 and each occurrence of QR$^X$, when present, is independently —C$_{1-3}$alkyl, —O(C$_{1-3}$alkyl), —CF$_3$, —OCF$_3$, —SCF$_3$, —F, —Cl, —Br, —COOR', —COR', —O(CH$_2$)$_2$N(R)(R'), —O(CH$_2$)N(R)(R'), —CON(R)(R'), —(CH$_2$)$_2$OR', —(CH$_2$)OR', optionally substituted phenyl, optionally substituted benzyl, —N(R)(R'), —(CH$_2$)$_2$N(R)(R'), —(CH$_2$)N(R)(R'), —or SO$_2$NRR'.

As described generally above, $R^2$ is halogen, —CF$_3$, —CN, —NO$_2$, or —T$_q$R. In certain embodiments, $R^2$ is T$_q$R, wherein T is a bond or is a $C_1$-$C_4$alkylidene chain, wherein one or two methylene units of T are optionally replaced by —CO—, —CONR—, —SO$_2$—, —NRSO$_2$—, —SO$_2$NR—, —O—, —S—, or —NR. In other preferred embodiments, $R^2$ is hydrogen or is optionally substituted $C_1$-$C_4$alkyl. In still other preferred embodiments, $R^2$ is hydrogen, —CF$_3$, —CH$_3$, —CH$_2$CH$_3$, —CH$_2$CH$_2$CH$_3$, —CH$_2$OR —(CH$_2$)$_2$OR, —(CH$_2$)$_3$OR, —CH$_2$N(R)$_2$, —(CH$_2$)$_2$N(R)$_2$, —(CH$_2$)$_3$N(R)$_2$, —CH$_2$NRCOR—(CH$_2$)$_2$NRCOR, or —(CH$_2$)$_3$NRCOR.

As described generally above, $R^3$ is U$_m$R' and $R^4$ is V$_p$Cy$^1$; wherein m, p, U, V, and Cy$^1$ are defined generally above and herein; or $R^3$ and $R^4$, taken together with the nitrogen atom to which they are bound form an optionally substituted 5-, 6- or 7-membered saturated, partially unsaturated or fully unsaturated ring having the structure:

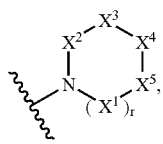

wherein r is 0, 1, or 2; one of $X^3$, $X^4$, or $X^5$ is CH—$V_p$-$Cy^1$ or N—$V_p$-$Cy^1$, and the others of $X^3$, $X^4$, or $X^5$ is $CHR^1$ or NR'; each occurrence of $X^1$, when present, and $X^2$ are each independently $C(R')_2$, —CO—, or —CS—.

In certain embodiments for compounds of general formulas I, I-A, or I-B, $R^3$ is $U_mR'$ and $R^4$ is $V_pCy^1$. In some embodiments, $R^3$ is hydrogen. In yet other embodiments, $R^3$ is optionally substituted $C_{1-4}$alkyl. In yet other embodiments $R^3$ is $U_mR'$ where m is 1 and U is —$CH_2$— and R' is a 5- or 6-membered optionally substituted saturated, partially unsaturated, or fully unsaturated ring having 0-3 heteroatoms independently selected from nitrogen, oxygen, or sulfur. In certain exemplary embodiments, R' is an optionally substituted phenyl or pyridyl group. In some embodiments, p is 1 and V is is —$CH_2C(R^6)_2$— or —$C(R^6)_2$—, wherein each occurrence of $R^6$ is independently halogen, CN, $NO_2$, or —YR, wherein Y is a bond or is an optionally substituted $C_1$-$C_4$ alkylidene chain wherein up to two methylene units of Y are optionally and independently replaced by —O—, —NR—, —CO—, —S—, —SO—, or —$SO_2$—, or wherein the two occurrences of $R^6$ on the same carbon atom are taken together to form an optionally substituted 3-6-membered spiro ring having 0-3 heteroatoms. In certain embodiments, $R^6$ is hydrogen, methyl, or two occurrences of $R^6$ on the same carbon atom are taken together to form an optionally substituted 3-6-membered spiro ring having 0, 1 or 2 heteroatoms selected from nitrogen, oxygen, or sulfur. In still other embodiments, p is 0 and $R^4$ is $Cy^1$.

In yet other embodiments, $R^3$ and $R^4$, taken together with the nitrogen atom to which they are bound form an optionally substituted 5-, 6- or 7-membered saturated, partially unsaturated or fully unsaturated ring having the structure:

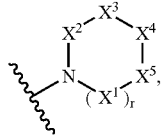

wherein r is 0, 1, or 2; one of $X^3$, $X^4$, or $X^5$ is CH—$V_p$-$Cy^1$ or N—$V_p$-$Cy^1$, and the others of $X^3$, $X^4$, or $X^5$ is $CHR^1$ or NR'; each occurrence of $X^1$, when present, and $X^2$ are each independently $C(R')_2$, —CO—, or —CS—. In certain embodiments, r is 1, $X^1$, $X^2$, $X^3$ and $X^5$ are each $CH_2$, and $X^4$ is CH—$V_p$-$Cy^1$, or N—$V_p$-$Cy^1$. In certain other embodiments, p is 1 and V is $SO_2$, —$NRSO_2$, CO, or NRCO. In still other embodiments, $X^4$ is N—$V_p$-$Cy^1$, p is 1 and V is $SO_2$ or CO.

As described generally above, $Cy^1$ is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein $Cy^1$ is optionally substituted at one or more carbon or nitrogen atoms with y independent occurrences of —$WR^W$; wherein y is 0-5; wherein W is a bond or is a $C_1$-$C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2NR$—, —$NRSO_2NR$—, —O—, —S—; or —NR—; and each occurrence of $R^W$ is independently R', halogen, $NO_2$, or CN, or —$WR^W$ is =O, =S, or =NR'.

In certain embodiments, $Cy^1$ is selected from one of the following rings:

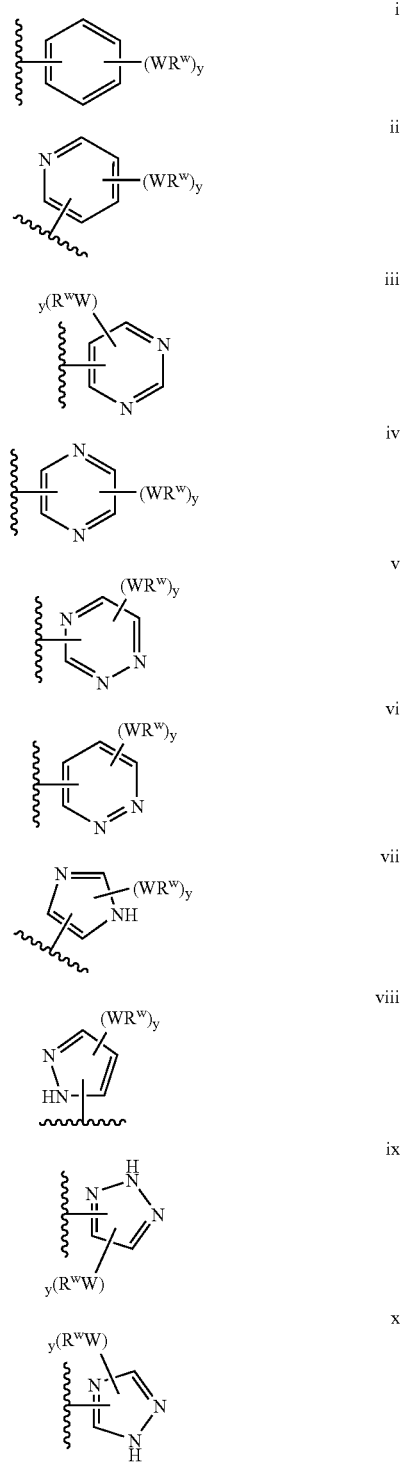

-continued
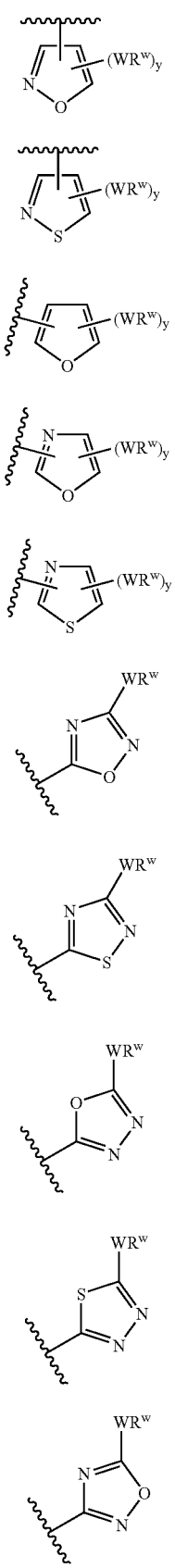
xi
xii
xiii
xiv
xv
xvi
xvii
xviii
xix
xx
-continued
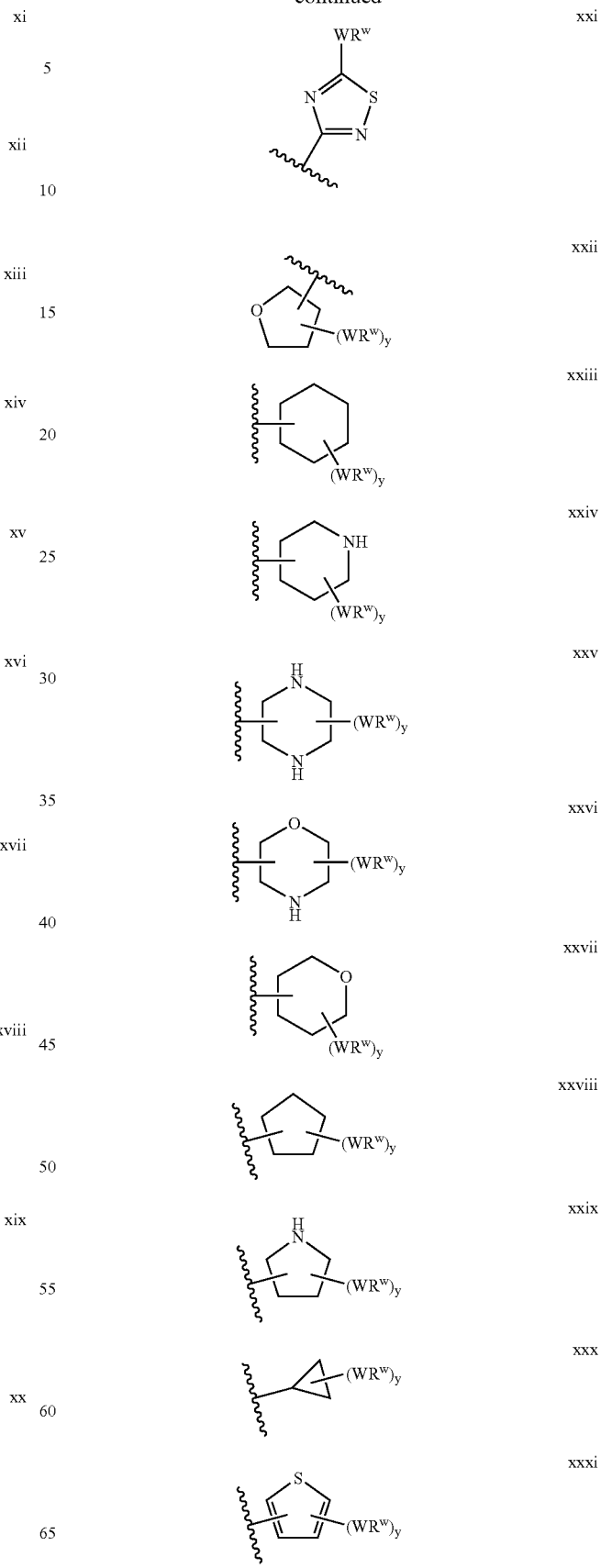
xxi
xxii
xxiii
xxiv
xxv
xxvi
xxvii
xxviii
xxix
xxx
xxxi -continued

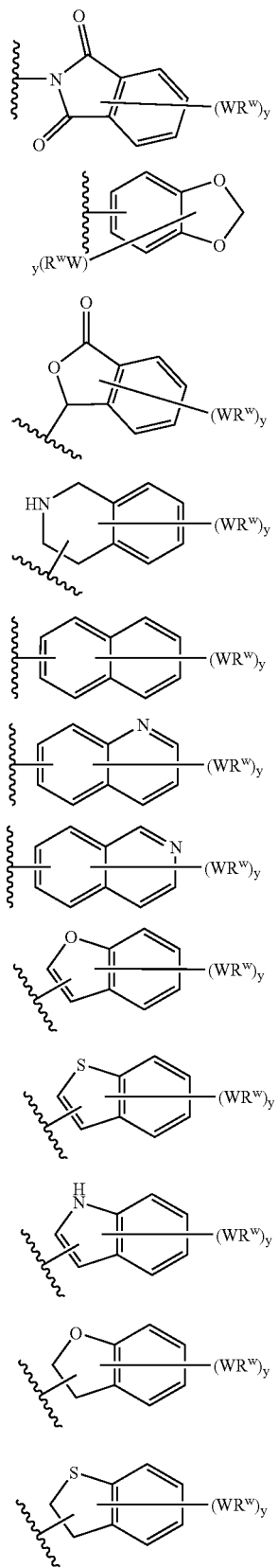

xxxii
xxxiii
xxxiv
xxxv
xxxvi
xxxvii
xxxviii
xxxix
xL
xLi
xLii
xLiii

-continued

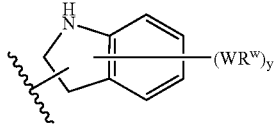

xLiv

It will be appreciated that, as described generally above, $Cy^1$ is optionally substituted at one or more carbon or nitrogen atoms with y independent occurrences of —$WR^W$; y is 0-5; wherein W is a bond or is a $C_1$-$C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2NR$—, —$NRSO_2NR$—, —O—, —S—; or —NR—; and each occurrence of $R^W$ is independently R', halogen, $NO_2$, or CN, or —$WR^W$ is =O, =S, or =NR'. In certain embodiments, y is 0, 1, 2 or 3, and W is a bond or is an optionally substituted $C_1$-$C_6$ alkylidene chain wherein one or two methylene units are optionally and independently replaced by O, NR, S, $SO_2$, or $CO_2$, CO, and $R^W$ is R' or halogen. In other embodiments, y is 0, 1, 2, or 3 and each occurrence of $WR^W$, when present, is independently —$C_{1-3}$ alkyl, —O($C_{1-3}$alkyl), —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), -or $SO_2NRR'$.

In addition to the compounds and subsets described above, certain additional compounds are of interest.

For example, in certain embodiments, Z is $CH_2$, $R^2$ and $R^3$ are each hydrogen, and $R^4$ is $V_pCy^1$, where p is 1 and V is —$CH_2C(R^6)_2$ and compounds have the general formula II:

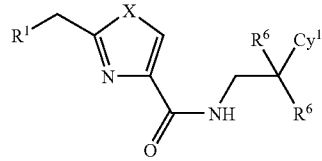

II where $R^1$, X, $R^6$ and $Cy^1$ are as defined generally above and in subsets herein.

As described generally above, X is S or O and compounds of formula II-A or II-B are provided:

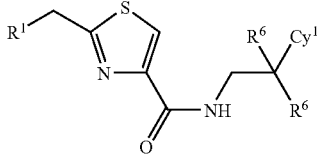

II-A

-continued
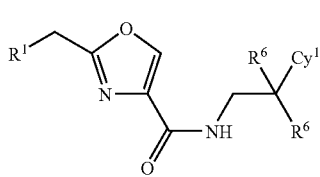
II-B
In some embodiments, for compounds of general formulae II, II-A, or II-B, $R^1$ is selected from one of the following groups:
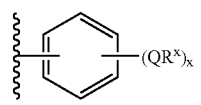 a
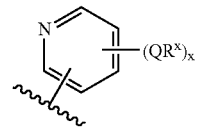 b
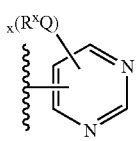 c
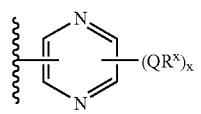 d
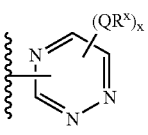 e
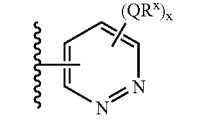 f
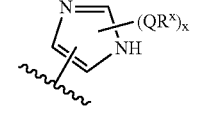 g
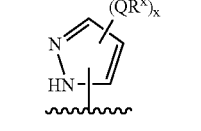 h
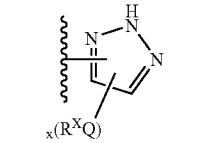 i
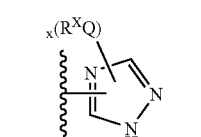 j
-continued
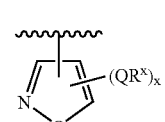 k
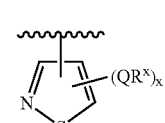 l
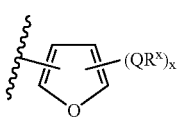 m
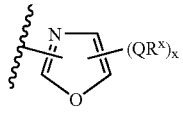 n
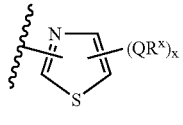 o
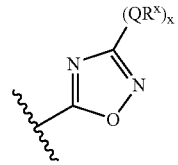 p
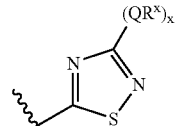 q
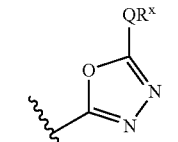 r
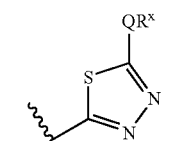 s
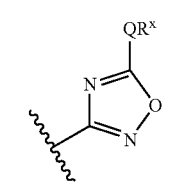 t

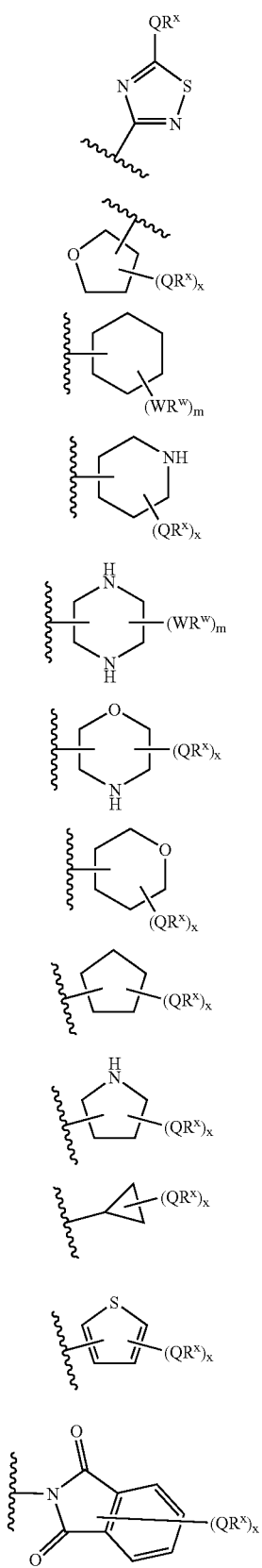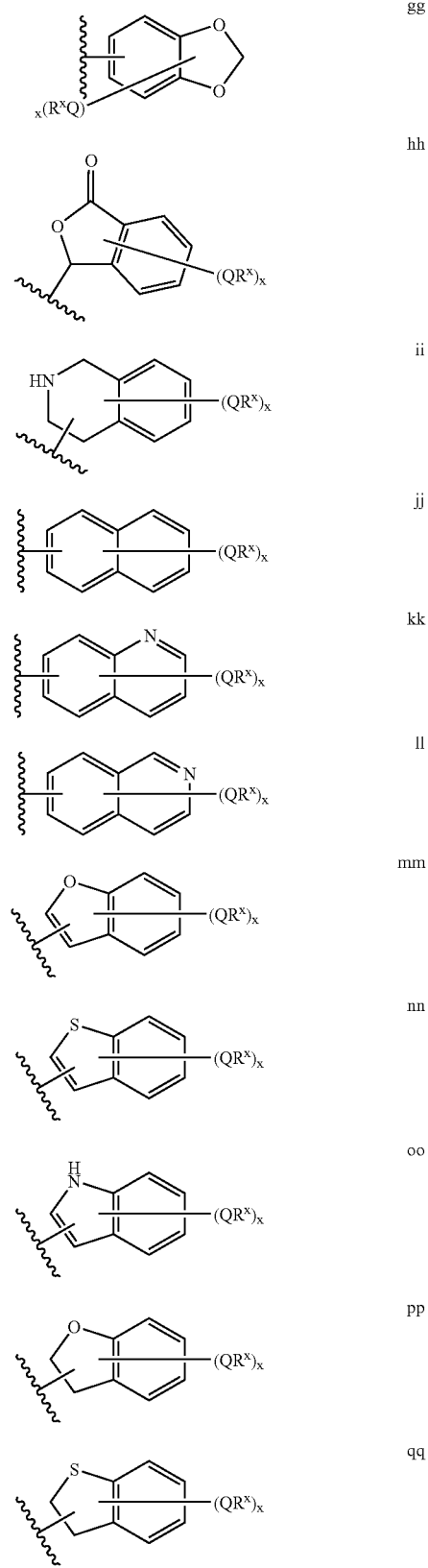

-continued

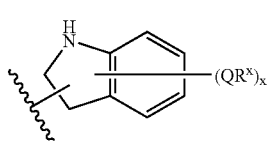
rr

In other embodiments $R^1$ is one of rings a, b, c, d, m, n, o, ee, gg, or pp. In other embodiments $R^1$ is ring a. In certain other embodiments, $R^1$ is ring gg.

In certain embodiments, for compounds of formulae II, II-A, or II-B, x is 0, 1, 2 or 3, and Q is a bond or is an optionally substituted $C_{1-6}$ alkylidene chain wherein one or two methylene units are optionally and independently replaced by O, NR, S, $SO_2$, or $CO_2$, CO, and $R^X$ is R' or halogen. In other embodiments, x is 0, 1, 2, or 3 and each occurrence of $QR^X$, when present, is independently —$C_{1-3}$alkyl, —O($C_{1-3}$alkyl), —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), —or $SO_2$NRR'.

In yet other embodiments, for compounds of general formulae II, II-A, or II-B, $R^6$ is hydrogen, methyl, or two occurrences of $R^6$ on the same carbon atom are taken together to form an optionally substituted 3-6-membered spiro ring having 0, 1 or 2 heteroatoms selected from nitrogen, oxygen, or sulfur.

In certain embodiments, for compounds of general formulae II, II-A, or II-B, $Cy^1$ is selected from one of the following rings:

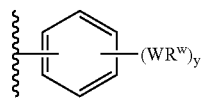
i

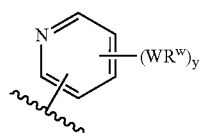
ii

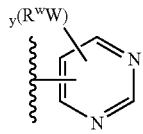
iii

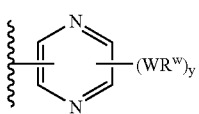
iv

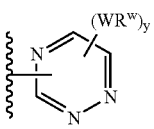
v

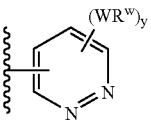
vi

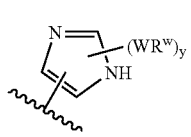
vii

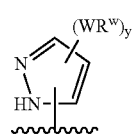
viii

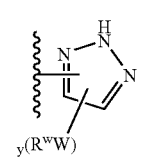
ix

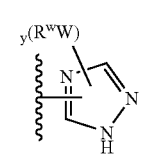
x

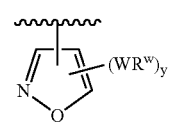
xi

xii

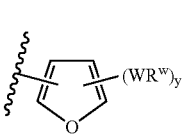
xiii

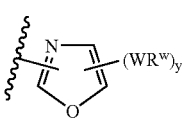
xiv

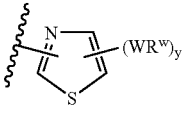
xv

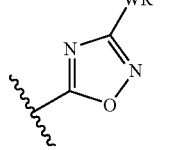
xvi

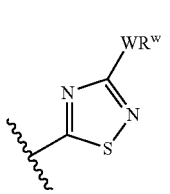
xvii

-continued
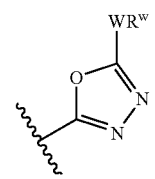 xviii
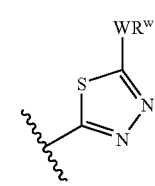 xix
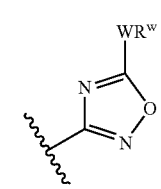 xx
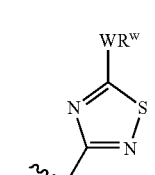 xxi
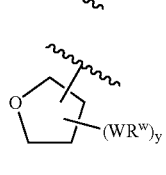 xxii
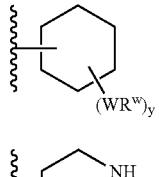 xxiii
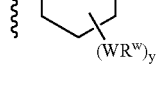 xxiv
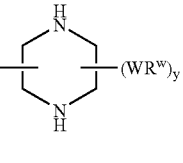 xxv
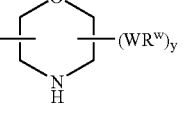 xxvi
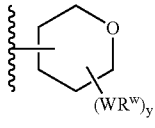 xxvii
-continued
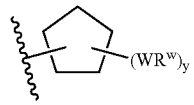 xxviii
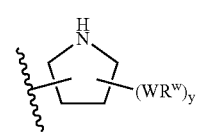 xxix
 xxx
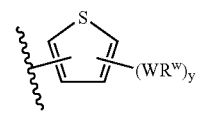 xxxi
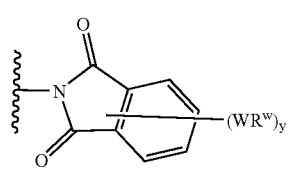 xxxii
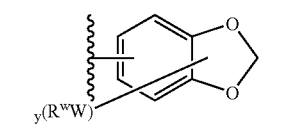 xxxiii
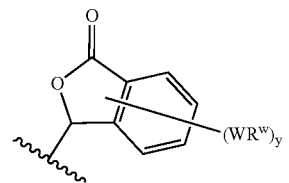 xxxiv
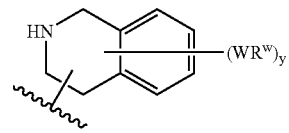 xxxv
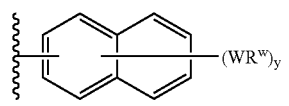 xxxvi
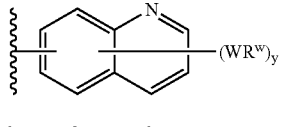 xxxvii
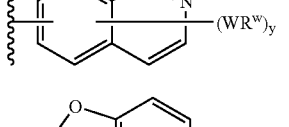 xxxviii
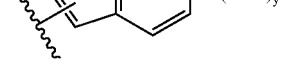 xxxix -continued

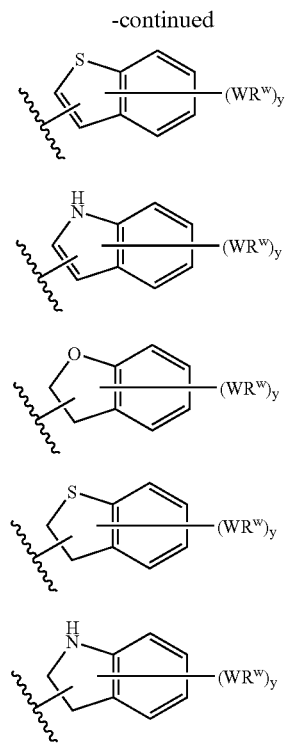

xL xLi xLii xLiii xLiv

In certain embodiments, for compounds of formulae II, II-A, or II-B, y is 0-5; wherein W is a bond or is a $C_1$-$C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2$NR—, —$NRSO_2$NR—, —O—, —S—; or —NR—; and each occurrence of $R^W$ is independently R', halogen, $NO_2$, or CN, or —$WR^W$ is =O, =S, or =NR'. In certain embodiments, y is 0, 1, 2 or 3, and W is a bond or is an optionally substituted $C_{1-6}$ alkylidene chain wherein one or two methylene units are optionally and independently replaced by O, NR, S, $SO_2$, or $CO_2$, CO, and $R^W$ is R' or halogen. In other embodiments, y is 0, 1, 2, or 3 and each occurrence of $WR^W$, when present, is independently —$C_{1-3}$ alkyl, —O($C_{1-3}$alkyl), —OPh, —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), -or $SO_2$NRR'.

In yet other embodiments, Z is a bond and R' is 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; $R^2$ is hydrogen; $R^3$ is $U_m$R' where m is 0 or 1, and U, when present, is —$CH_2$— and R' is a 5- or 6-membered optionally substituted saturated, partially unsaturated, or fully unsaturated ring having 0-3 heteroatoms independently selected from nitrogen, oxygen, or sulfur; and $R^4$ is —$CH_2$$Cy^1$ and compounds of formula III are provided:

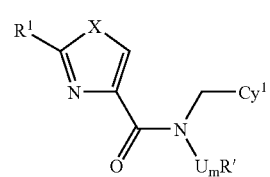

III where $R^1$, X, U, m, R', and $Cy^1$ are as defined generally above and in subsets herein.

As described generally above, X is S or O and compounds of formula III-A or III-B are provided:

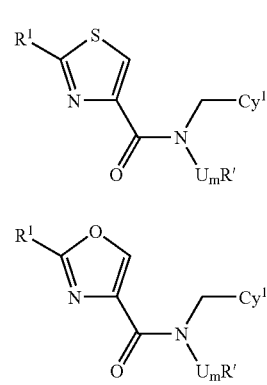

III-A

III-B

In some embodiments, for compounds of general formulae III, III-A, or III-B, $R^1$ is selected from one of the following groups:

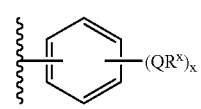

a

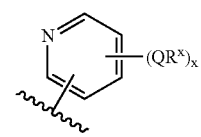

b

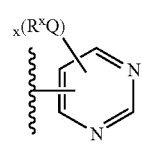

c

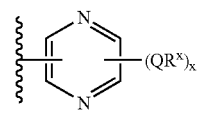

d

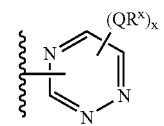

e

-continued
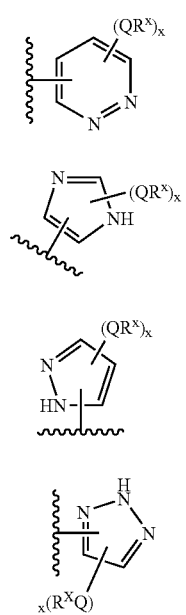
f
g
h
i
j
k
l
m
n
o
p
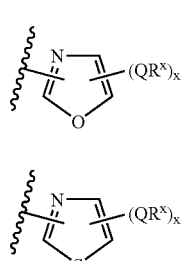
-continued
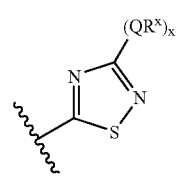
q
r
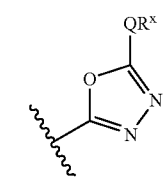
s
t
u
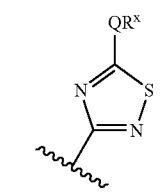
v
w
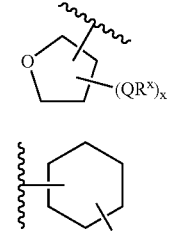
x
y
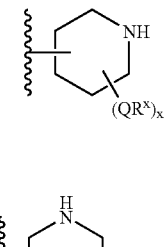

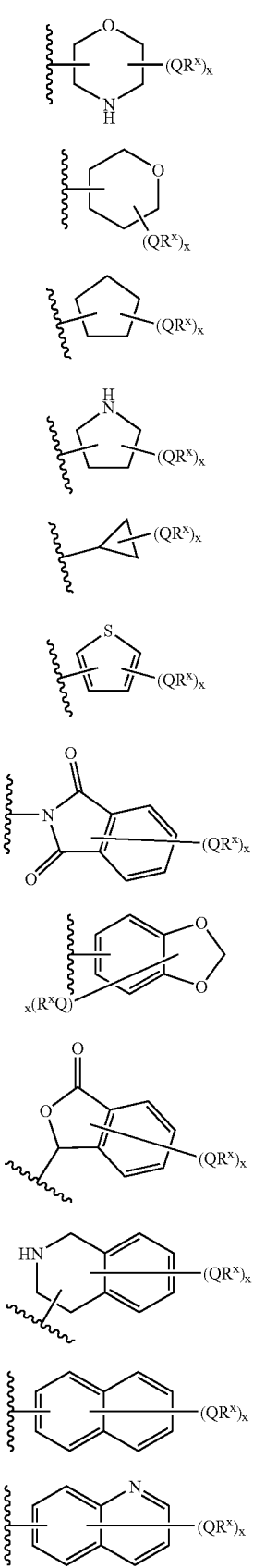

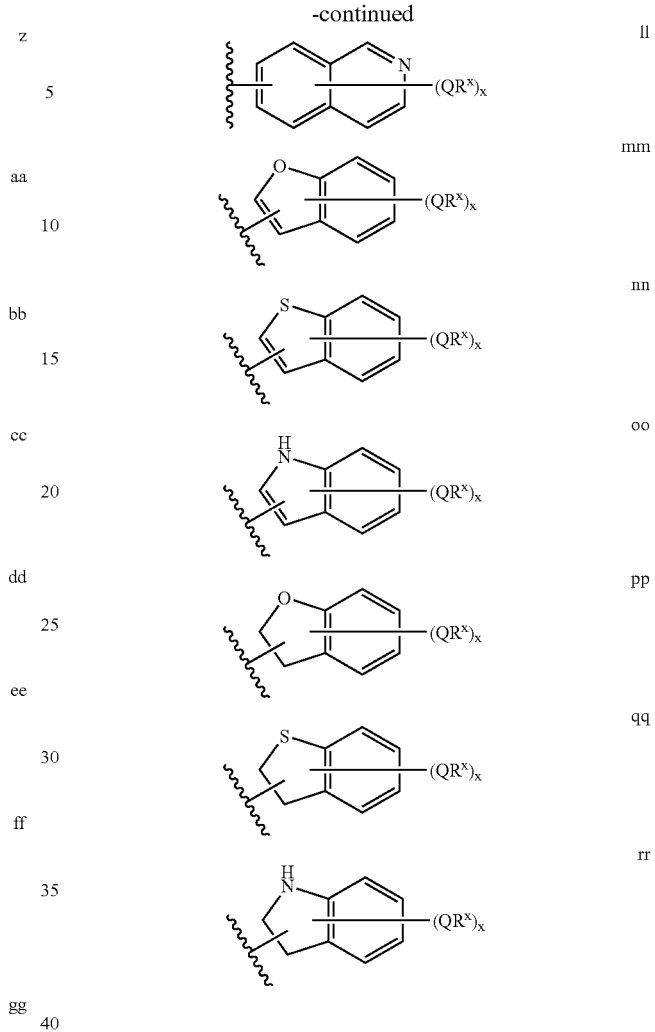

In other embodiments $R^1$ is one of rings a, b, c, d, m, n, o, ee, gg, or pp. In other embodiments $R^1$ is ring a. In certain other embodiments, $R^1$ is ring gg.

In certain embodiments, for compounds of formulae III, III-A, or III-B, x is 0, 1, 2 or 3, and Q is a bond or is an optionally substituted $C_{1-6}$ alkylidene chain wherein one or two methylene units are optionally and independently replaced by O, NR, S, $SO_2$, or $CO_2$, CO, and $R^x$ is R' or halogen. In other embodiments, x is 0, 1, 2, or 3 and each occurrence of $QR^x$, when present, is independently —$C_{1-3}$ alkyl, —O($C_{1-3}$alkyl), —$CF_3$, —$OCF_3$, —$SCF_3$, —F, —Cl, —Br, —COOR', —COR', —O($CH_2)_2$N(R)(R'), —O($CH_2$)N(R)(R'), —CON(R)(R'), —($CH_2)_2$OR', —($CH_2$)OR', optionally substituted phenyl, optionally substituted benzyl, —N(R)(R'), —($CH_2)_2$N(R)(R'), —($CH_2$)N(R)(R'), —or $SO_2NRR'$.

As described generally above for compounds of formula III, $R^3$ is $U_mR'$ where m is 0 or 1, and U, when present, is —$CH_2$— and R' is a 5- or 6-membered optionally substituted saturated, partially unsaturated, or fully unsaturated ring having 0-3 heteroatoms independently selected from nitrogen, oxygen, or sulfur. In certain embodiments, R' is an optionally substituted phenyl or pyridyl group.

In certain embodiments, for compounds of general formulae III, III-A, or III-B, $Cy^1$ is selected from one of the following rings:

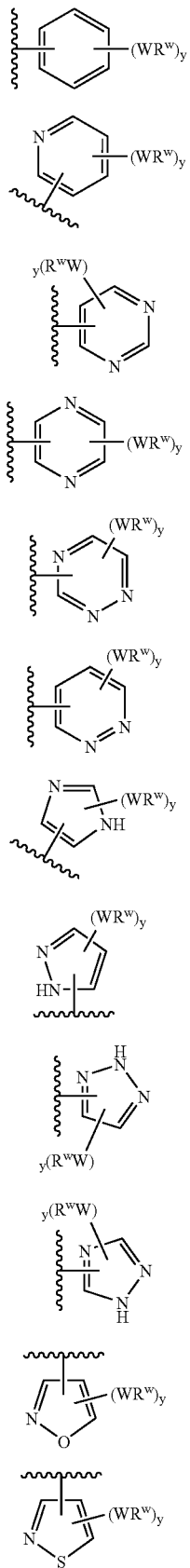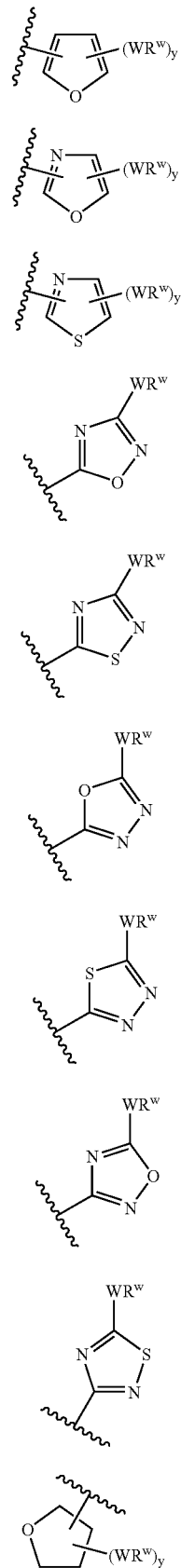

-continued
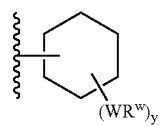 xxiii
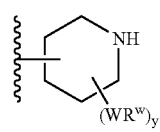 xxiv
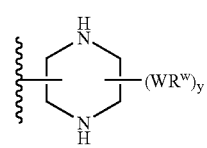 xxv
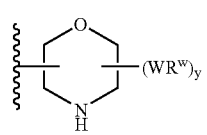 xxvi
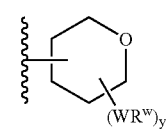 xxvii
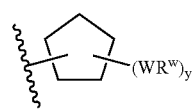 xxviii
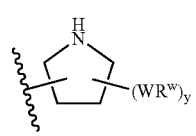 xxix
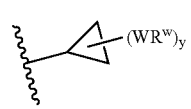 xxx
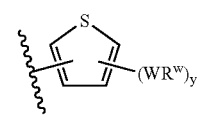 xxxi
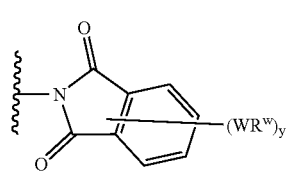 xxxii
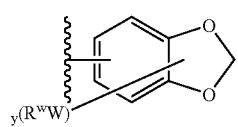 xxxiii
-continued
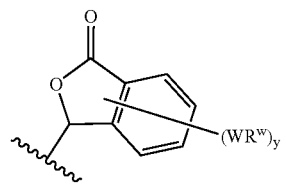 xxxiv
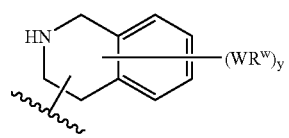 xxxv
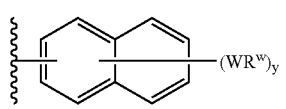 xxxvi
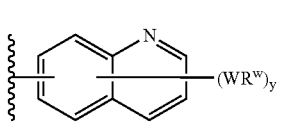 xxxvii
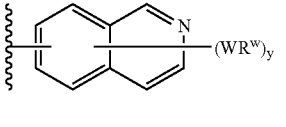 xxxviii
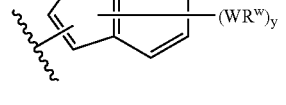 xxxix
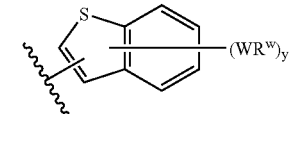 xL
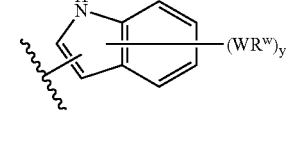 xLi
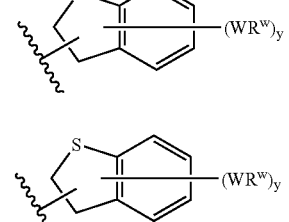 xLii
xLiii
xLiv In certain embodiments, for compounds of formulae III, III-A, or III-B, y is 0-5; wherein W is a bond or is a $C_1$-$C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2NR$—, —$NRSO_2NR$—, —O—, —S—; or —NR—; and each occurrence of $R^W$ is independently R', halogen, $NO_2$, or CN, or —$WR^W$ is =O, =S, or =NR'. In certain embodiments, y is 0, 1, 2 or 3, and W is a bond or is an optionally substituted $C_{1-6}$ alkylidene chain wherein one or two methylene units are optionally and independently replaced by O, NR, S, $SO_2$, or $CO_2$, CO, and $R^W$ is R' or halogen. In other embodiments, y is 0, 1, 2, or 3 and each occurrence of $WR^W$, when present, is independently —$C_{1-3}$ alkyl, —O($C_{1-3}$alkyl), —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), -or $SO_2NRR'$.

In still other embodiments, Z—$R^1$ is —$CH_3$; $R^2$ is hydrogen; $R^3$ is $U_mR'$ where m is 0 or 1, and U, when present, is —$CH_2$— and R' is a 5- or 6-membered optionally substituted saturated, partially unsaturated, or fully unsaturated ring having 0-3 heteroatoms independently selected from nitrogen, oxygen, or sulfur; and $R^4$ is —$CH_2Cy^1$ and compounds of formula IV are provided:

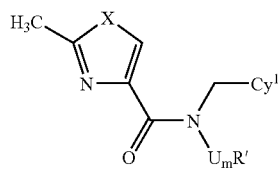

IV where X, U, m, R', and $Cy^1$ are as defined generally above and in subsets herein.

As described generally above, X is S or O and compounds of formula IV-A or IV-B are provided:

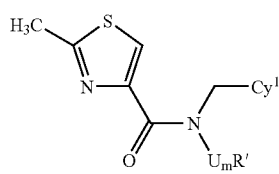

IV-A

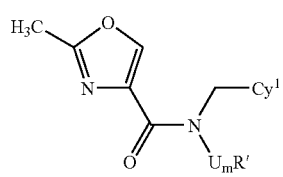

IV-B

As described generally above for compounds of formula IV, $R^3$ is $U_mR'$ where m is 0 or 1, and U, when present, is —$CH_2$— and R' is a 5- or 6-membered optionally substituted saturated, partially unsaturated, or fully unsaturated ring having 0-3 heteroatoms independently selected from nitrogen, oxygen, or sulfur. In certain embodiments, R' is an optionally substituted phenyl or pyridyl group.

In certain embodiments, for compounds of general formulae IV, IV-A, or IV-B, $Cy^1$ is selected from one of the following rings:

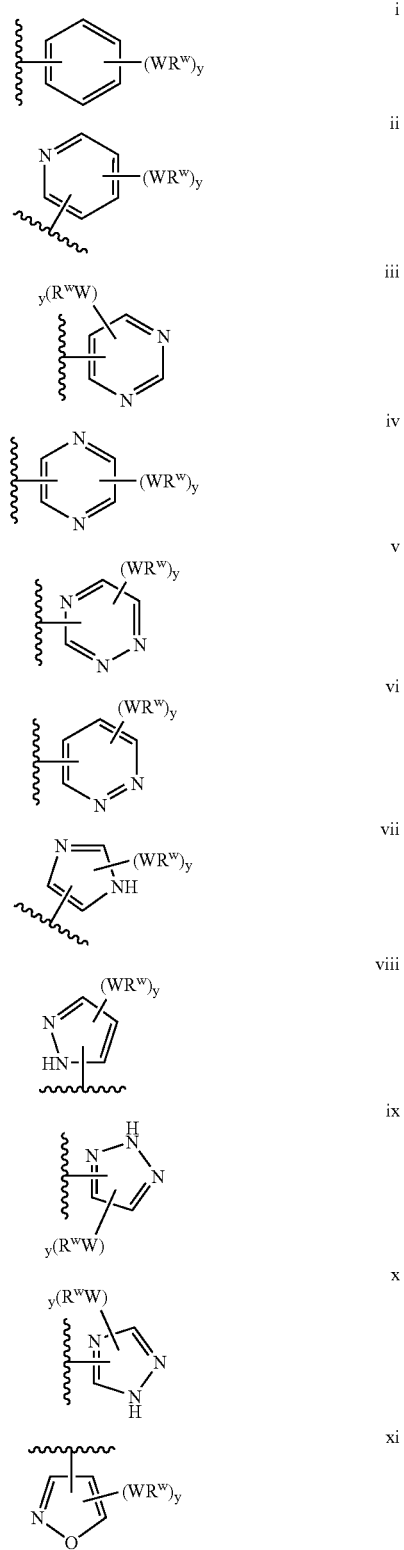

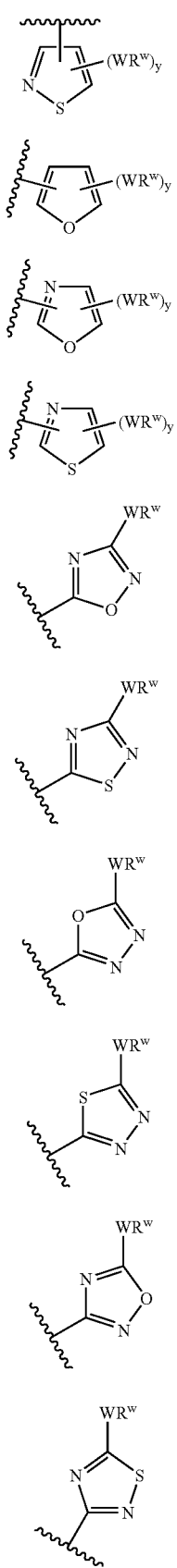
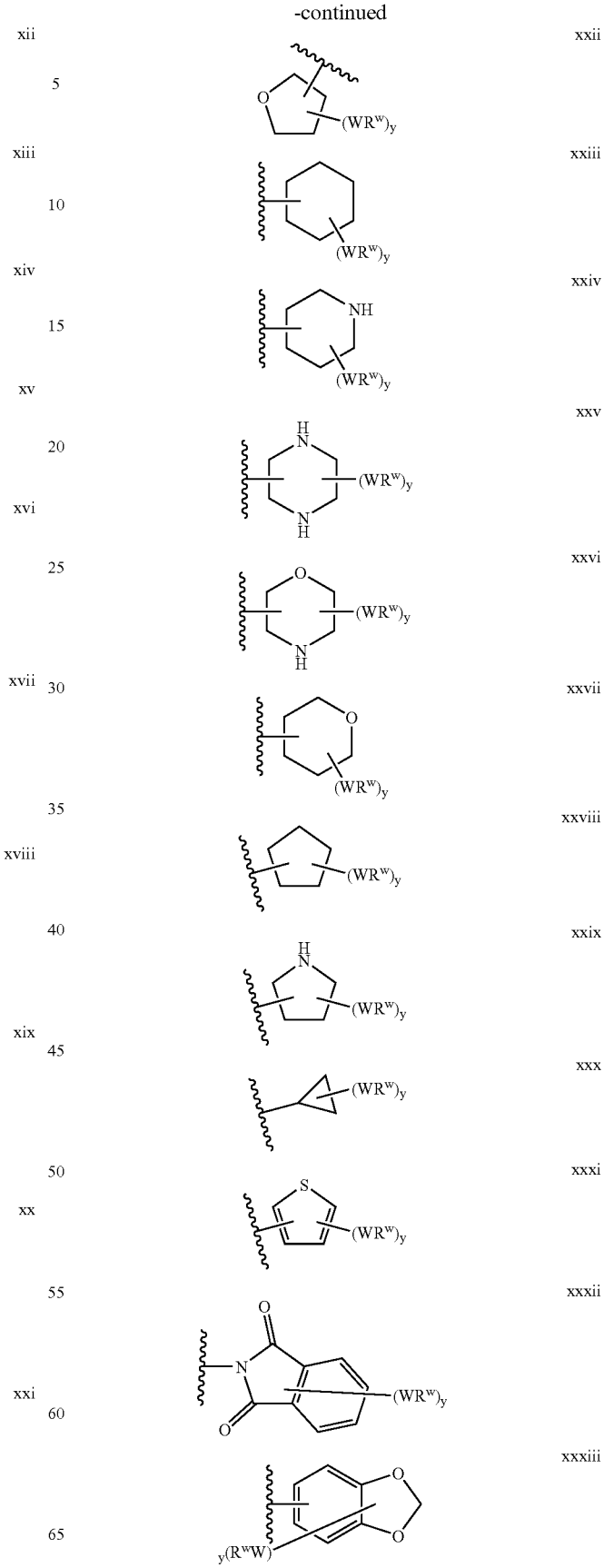

-continued

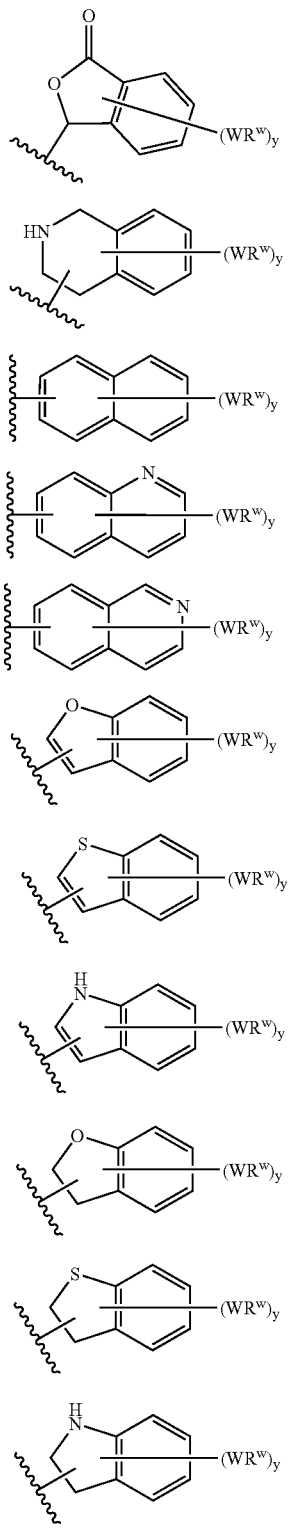

xxxiv xxxv xxxvi xxxvii xxxviii xxxix xL xLi xLii xLiii xLiv

In certain embodiments, for compounds of formulae IV, IV-A, or IV-B, y is 0-5; wherein W is a bond or is a $C_1$-$C_6$ alkylidene chain wherein up to two methylene units of W are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and each occurrence of $R^W$ is independently R', halogen, NO$_2$, or CN, or —WR$^W$ is =O, =S, or =NR'. In certain embodiments, y is 0, 1, 2 or 3, and W is a bond or is an optionally substituted $C_{1-6}$ alkylidene chain wherein one or two methylene units are optionally and independently replaced by O, NR, S, SO$_2$, or CO$_2$, CO, and $R^W$ is R' or halogen. In other embodiments, y is 0, 1, 2, or 3 and each occurrence of WR$^W$, when present, is independently —$C_{1-3}$ alkyl, —O($C_{1-3}$alkyl), —CF$_3$, —OCF$_3$, —SCF$_3$, —F, —Cl, —Br, —COOR', —COR', —O(CH$_2$)$_2$N(R)(R'), —O(CH$_2$)N(R)(R'), —CON(R)(R'), —(CH$_2$)$_2$OR', —(CH$_2$)OR', optionally substituted phenyl, optionally substituted benzyl, —N(R)(R'), —(CH$_2$)$_2$N(R)(R'), —(CH$_2$)N(R)(R'), -or SO$_2$NRR'.

In yet other embodiments, Z is —CH$_2$—; and R$^3$ and R$^4$, taken together with the nitrogen atom to which they are bound form an optionally substituted 5-, 6- or 7-membered saturated, partially unsaturated or fully unsaturated ring having the structure

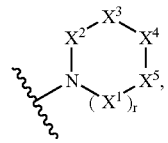

wherein r is 0, 1, or 2; one of X$^3$, X$^4$, or X$^5$ is CH—V$_p$-Cy$^1$ or N—V$_p$-Cy$^1$, and the others of X$^3$, X$^4$, or X$^5$ is CHR' or NR'; each occurrence of X$^1$, when present, and X$^2$ are each independently C(R')$_2$, —CO—, or —CS—, and compounds of formula V are provided:

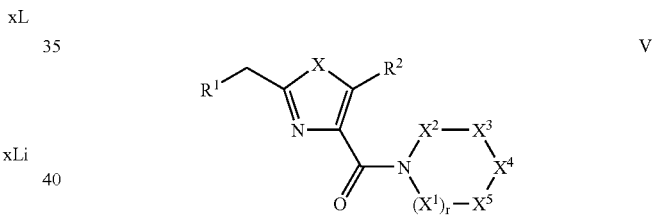

where R$^1$, X, R$^2$, X$^1$, X$^2$, X$^3$, X$^4$, X$^5$ and r are as described generally above and in subsets herein.

As described generally above, X is S or O and compounds of formula V-A or V-B are provided:

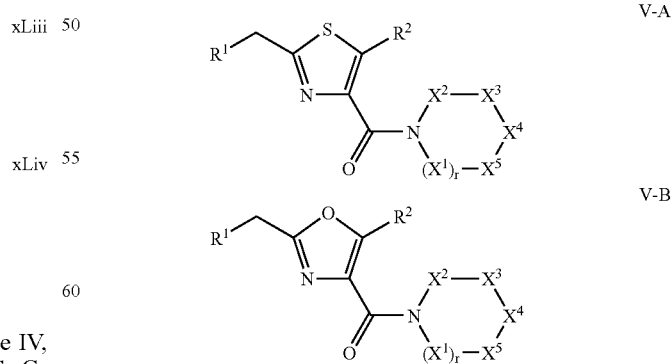

In some embodiments, for compounds of general formulae V, V-A, or V-B, R$^1$ is selected from one of the following groups:

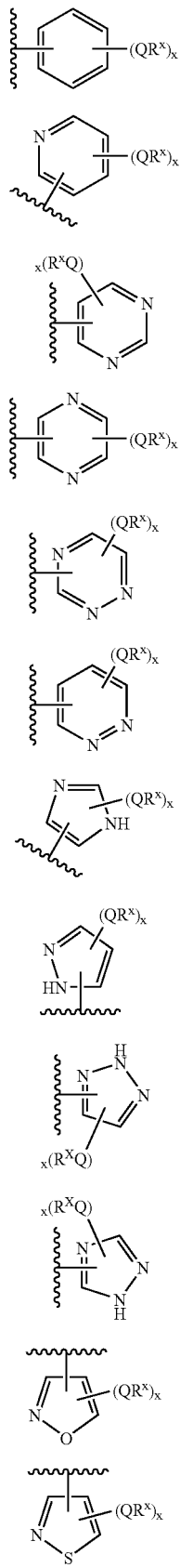
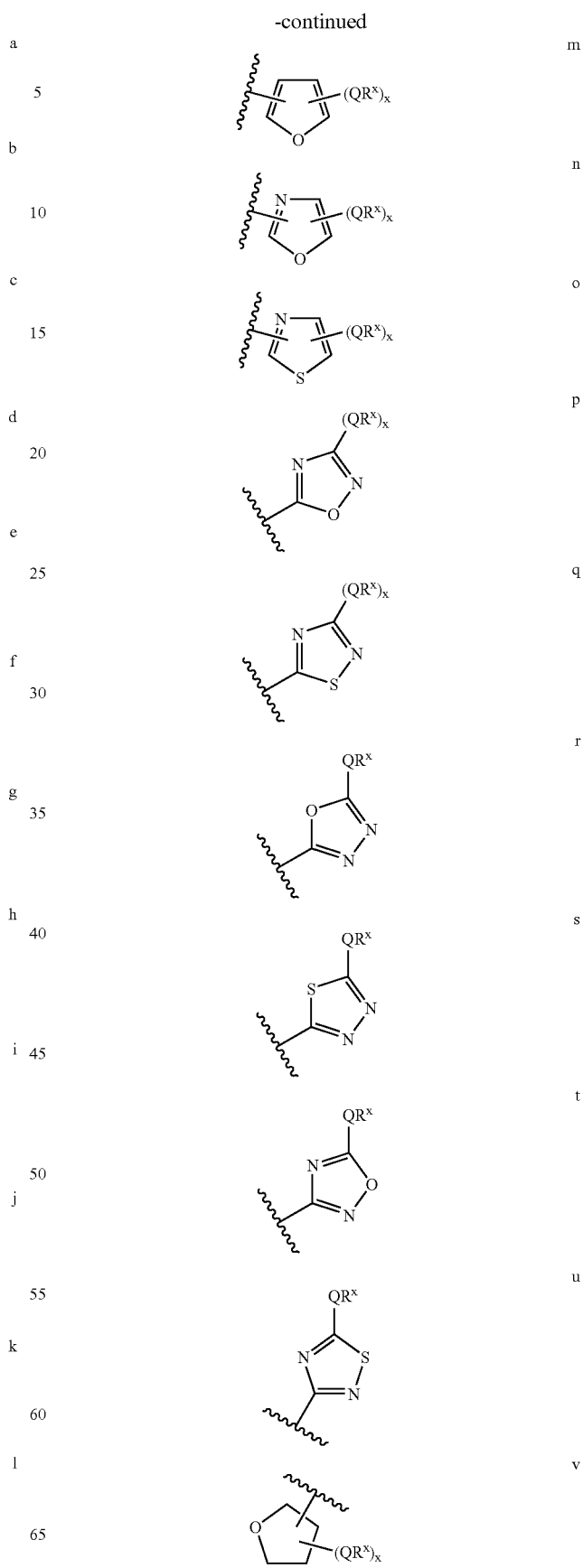

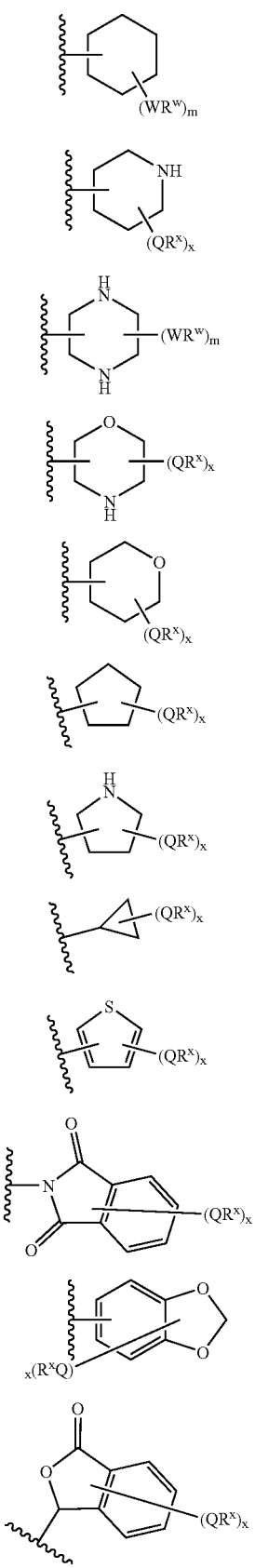
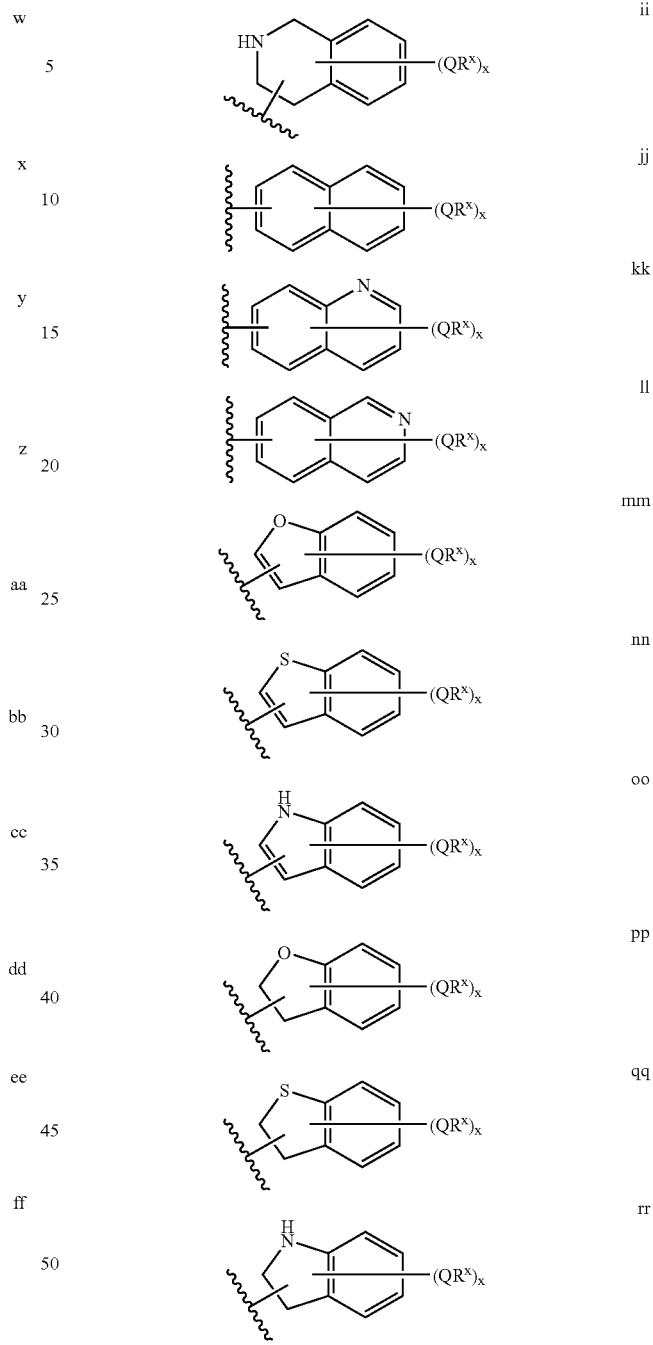

In other embodiments R¹ is one of rings a, b, c, d, m, n, o, ee, gg, or pp. In other embodiments R¹ is ring a. In certain other embodiments, R¹ is ring gg.

In certain embodiments, for compounds of formulae V, V-A, or V-B, x is 0, 1, 2 or 3, and Q is a bond or is an optionally substituted $C_{1-6}$ alkylidene chain wherein one or two methylene units are optionally and independently replaced by O, NR, S, $SO_2$, or $CO_2$, CO, and $R^x$ is R' or halogen. In other embodiments, x is 0, 1, 2 or 3 and each occurrence of $QR^x$, when present, is independently —$C_{1-3}$alkyl, —$O(C_{1-3}$alkyl), —$CF_3$, —$OCF_3$, —$SCF_3$, —F, —Cl, —Br, —COOR', —COR', —$O(CH_2)_2N(R)(R')$, —$O(CH_2)N(R)(R')$, —CON (R)(R'), —(CH$_2$)$_2$OR', —(CH$_2$)OR', optionally substituted phenyl, optionally substituted benzyl, —N(R)(R'), —(CH$_2$)$_2$N(R)(R'), —(CH$_2$)N(R)(R'), —or SO$_2$NRR'.

In certain embodiments, for compounds of general formulae V, V-A, or V-B, r is 1, $X^1$, $X^2$, $X^3$ and $X^5$ are each CH$_2$, and $X^4$ is CH—V$_p$-Cy$^1$, or N—V$_p$-Cy$^1$. In certain other embodiments, p is 1 and V is SO$_2$, —NRSO$_2$, CO, or NRCO. In still other embodiments, $X^4$ is N—V$_p$-Cy$^1$, p is 1 and V is SO$_2$ or CO. In yet other embodiments, for compounds of general formula V-A or V-B, $X^4$ is N—V$_p$—Cy$^1$, p is 1 and V is SO$_2$.

In certain embodiments, for compounds of general formulae V, V-A, or V-B, Cy$^1$ is selected from one of the following rings:

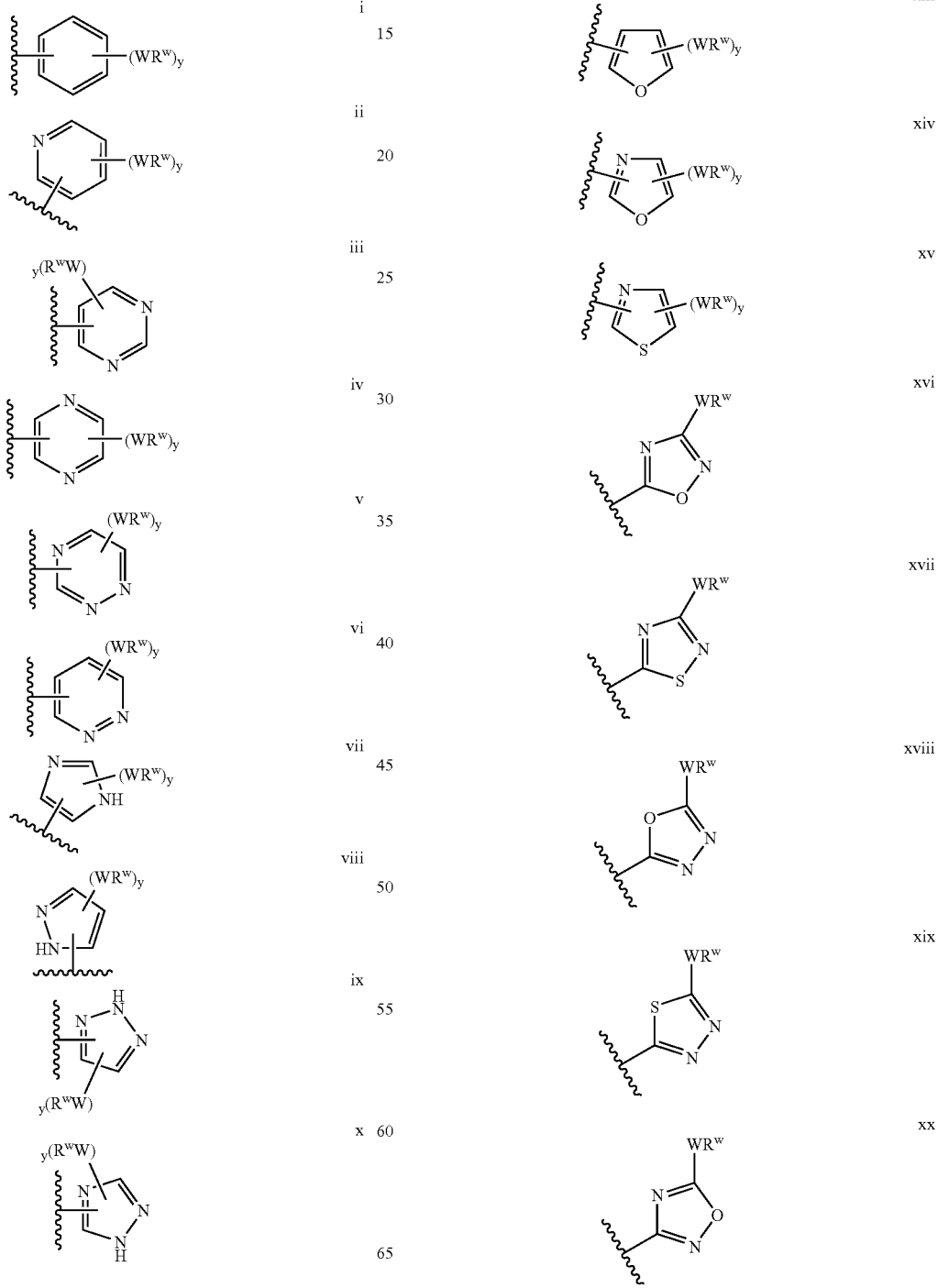

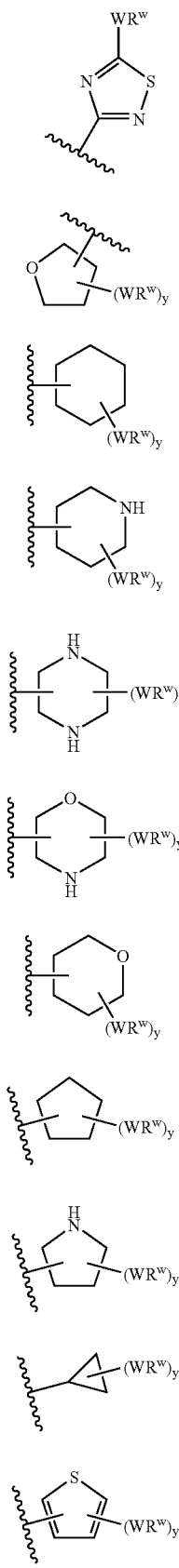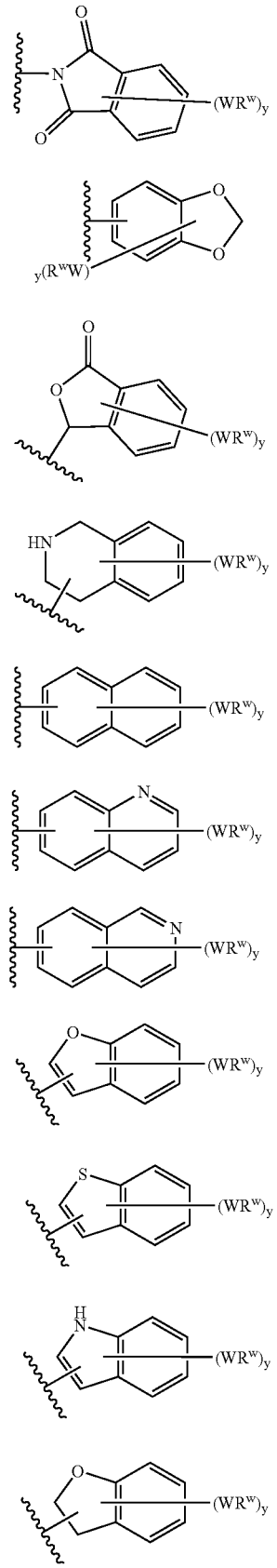

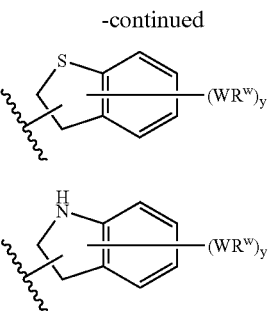

xLiii xLiv

In certain embodiments, for compounds of general formulae V, V-A, or V-B, y is 0-5; wherein W is a bond or is a $C_1$-$C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2$NR—, —$NRSO_2$NR—, —O—, —S—; or —NR—; and each occurrence of $R^W$ is independently R', halogen, $NO_2$, or CN, or —$WR^W$ is =O, =S, or =NR'. In certain embodiments, y is 0, 1, 2 or 3, and W is a bond or is an optionally substituted $C_{1-6}$ alkylidene chain wherein one or two methylene units are optionally and independently replaced by O, NR, S, $SO_2$, or $CO_2$, CO, and $R^W$ is R' or halogen. In other embodiments, y is 0, 1, 2, or 3 and each occurrence of $WR^W$, when present, is independently —$C_{1-3}$alkyl, —O($C_{1-3}$alkyl), —$CF_3$, —$OCF_3$, —$SCF_3$, —F, —Cl, —Br, —COOR', —COR', —O$(CH_2)_2$N(R)(R'), —O$(CH_2)$N(R)(R'), —CON(R)(R'), —$(CH_2)_2$OR', —$(CH_2)$OR', optionally substituted phenyl, optionally substituted benzyl, —N(R)(R'), —$(CH_2)_2$N(R)(R'), —$(CH_2)$N(R)(R'), -or $SO_2$NRR'.

In another embodiment, the present invention provides compounds of formula VI:

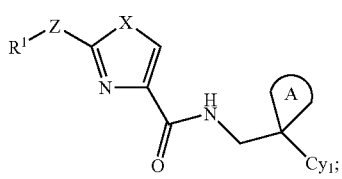

VI wherein:
ring A is a 3-7 membered ring having up to 3 heteroatoms selected from O, S, or NR;
R, $R^1$, Z, X, and Cy, are as defined above.

As described generally above, X is S or O, and compounds of formula VI-A or VI-B are provided:

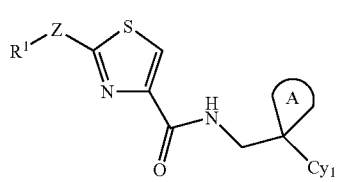

VI-A

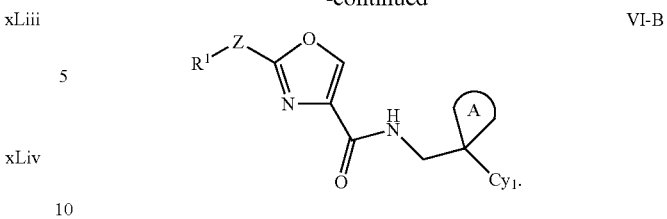

VI-B

In one embodiment, ring A is a 3-7 membered cycloalkyl ring. In another embodiment, ring A is cyclopropyl, cyclobutyl, cyclopentyl, or cyclohexyl. In certain embodiments, ring A is cyclopentyl or cyclohexyl.

In another embodiment, ring A has one oxygen ring heteroatom. Or, ring A has one sulfur ring heteroatom. Or, ring A has one nitrogen ring heteroatom. Preferably, R (in NR) is hydrogen.

In some embodiments, for compounds of general formulae VI, VI-A, or VI-B, $R^1$ is selected from one of the following groups:

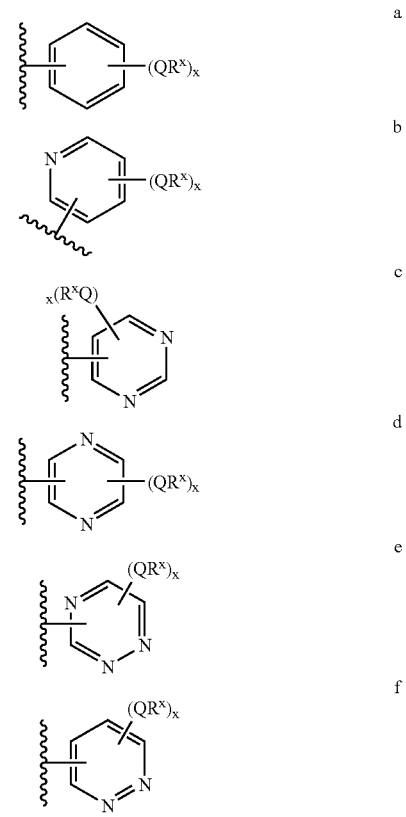

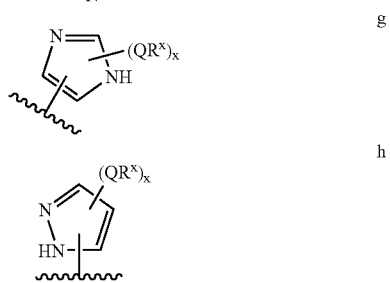

-continued
i
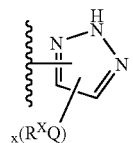
j
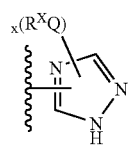
k
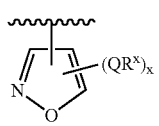
l
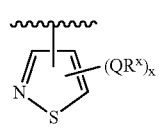
m
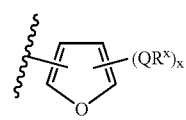
n
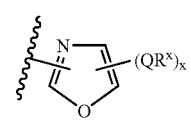
o
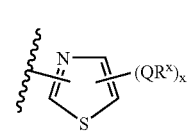
p
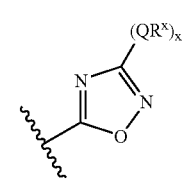
q
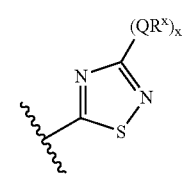
r
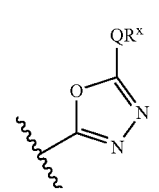
-continued
s
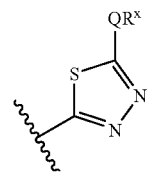
t
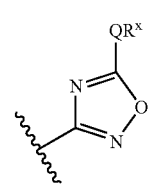
u
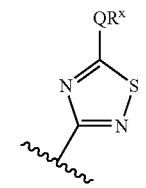
v
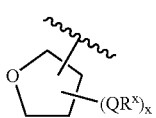
w
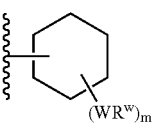
x
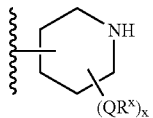
y
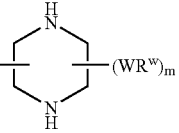
z
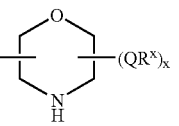
aa
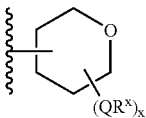
bb
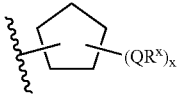

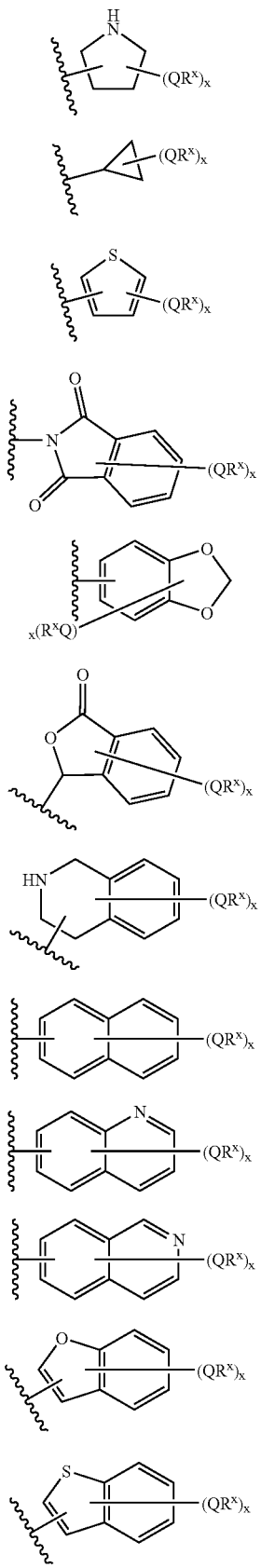
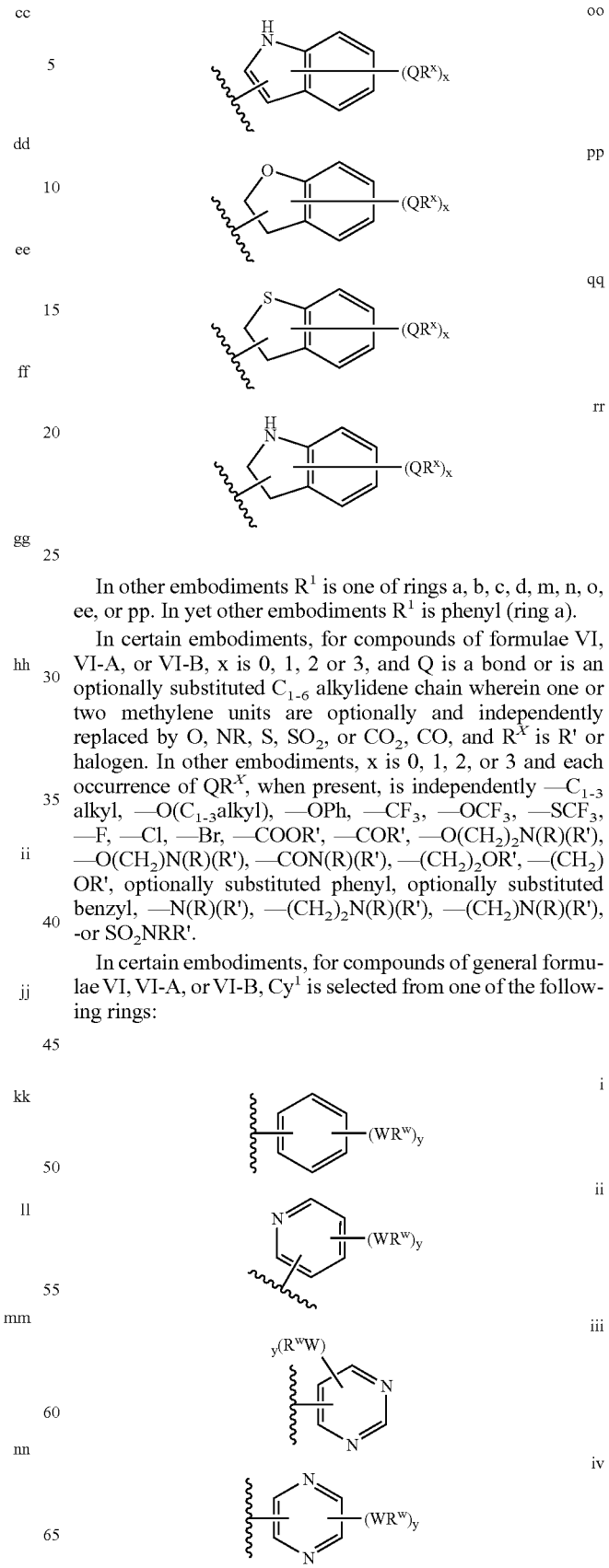

In other embodiments R¹ is one of rings a, b, c, d, m, n, o, ee, or pp. In yet other embodiments R¹ is phenyl (ring a).

In certain embodiments, for compounds of formulae VI, VI-A, or VI-B, x is 0, 1, 2 or 3, and Q is a bond or is an optionally substituted $C_{1-6}$ alkylidene chain wherein one or two methylene units are optionally and independently replaced by O, NR, S, $SO_2$, or $CO_2$, CO, and $R^X$ is R' or halogen. In other embodiments, x is 0, 1, 2, or 3 and each occurrence of $QR^X$, when present, is independently —$C_{1-3}$ alkyl, —$O(C_{1-3}alkyl)$, —OPh, —$CF_3$, —$OCF_3$, —$SCF_3$, —F, —Cl, —Br, —COOR', —COR', —$O(CH_2)_2N(R)(R')$, —$O(CH_2)N(R)(R')$, —$CON(R)(R')$, —$(CH_2)_2OR'$, —$(CH_2)OR'$, optionally substituted phenyl, optionally substituted benzyl, —N(R)(R'), —$(CH_2)_2N(R)(R')$, —$(CH_2)N(R)(R')$, -or $SO_2NRR'$.

In certain embodiments, for compounds of general formulae VI, VI-A, or VI-B, $Cy^1$ is selected from one of the following rings:

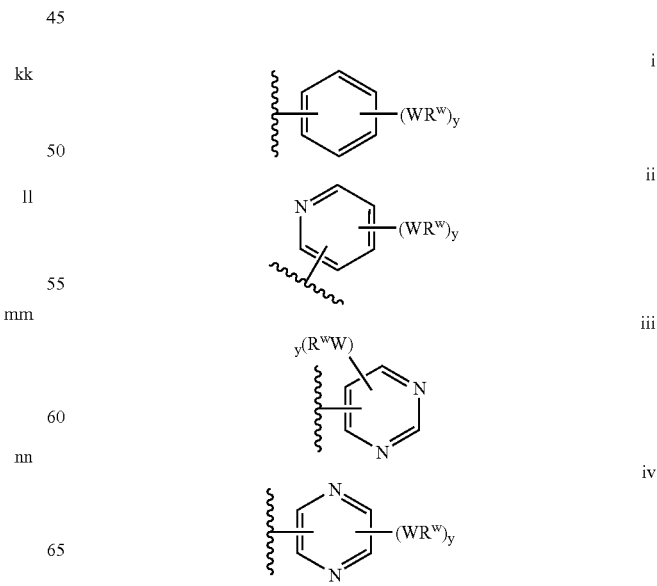

-continued

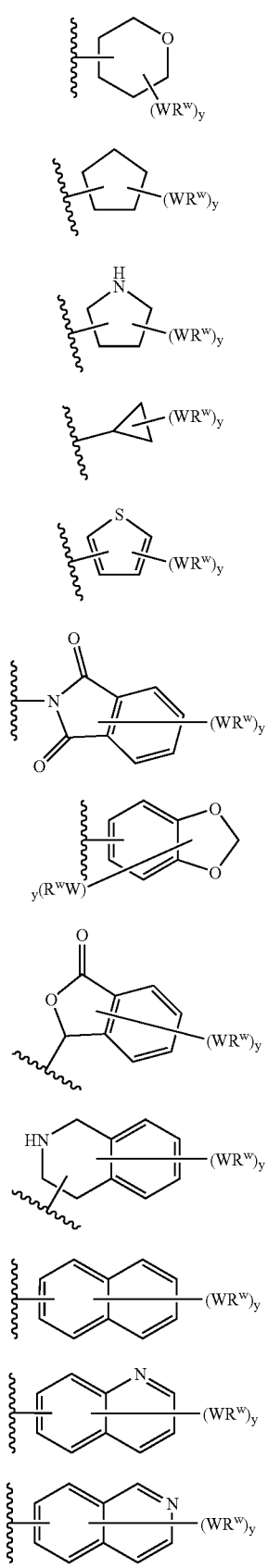
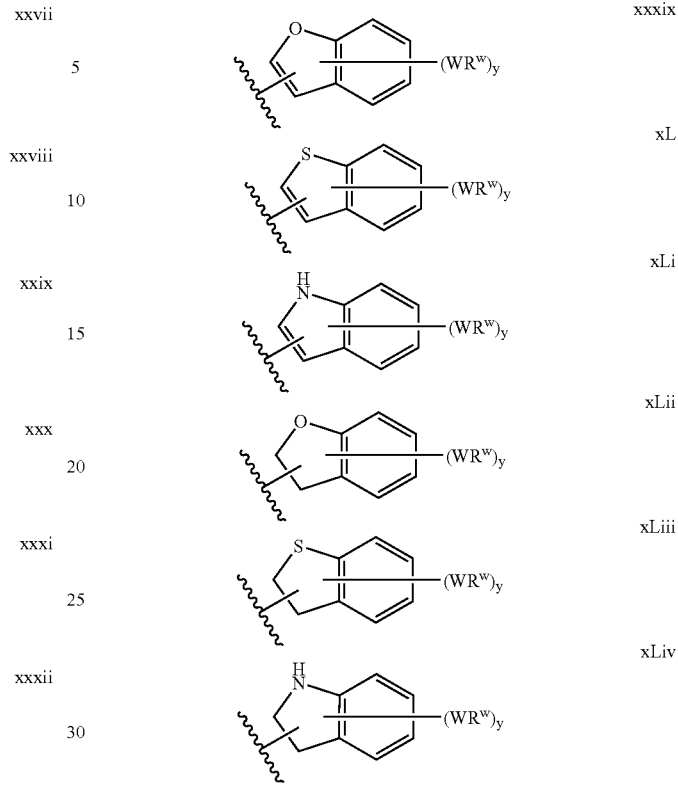

In one embodiment, $Cy_1$ is ring i or ring xxxiii above.

In certain embodiments, for compounds of general formulae VI, VI-A, or VI-B, y is 0-5; wherein W is a bond or is a $C_1-C_6$ alkylidene chain wherein up to two methylene units of W are optionally and independently replaced by —CO—, —$CO_2$—, —COCO—, —CONR—, —OCONR—, —NRNR—, —NRNRCO—, —NRCO—, —$NRCO_2$—, —NRCONR—, —SO—, —$SO_2$—, —$NRSO_2$—, —$SO_2NR$—, —$NRSO_2NR$—, —O—, —S—; or —NR—; and each occurrence of $R^W$ is independently R', halogen, $NO_2$, or CN, or —$WR^W$ is =O, =S, or =NR'. In certain embodiments, y is 0, 1, 2 or 3, and W is a bond or is an optionally substituted $C_{1-6}$ alkylidene chain wherein one or two methylene units are optionally and independently replaced by O, NR, S, $SO_2$, or $CO_2$, CO, and $R^W$ is R' or halogen. In other embodiments, y is 0, 1, 2, or 3 and each occurrence of $WR^W$, when present, is independently —$C_{1-3}$ alkyl, —O($C_{1-3}$alkyl), —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), —or $SO_2NRR'$.

In one embodiment, Z is —$CH_2$— or —$CH_2$—$CH_2$—. Or, Z is —$CH_2$—.

In another embodiment, $R^1$ is phenyl optionally substituted with up to three substituents selected from —$C_{1-3}$alkyl, —O($C_{1-3}$alkyl), —$CF_3$, —$OCF_3$, —$SCF_3$, —F, —Cl, —Br, —COOR', —COR', —O($CH_2$)$_2$N(R)(R'), —O($CH_2$)N(R)(R'), —CON(R)(R'), —($CH_2$)$_2$OR', —($CH_2$)OR', optionally substituted phenyl, optionally substituted benzyl, —N(R)(R'), —($CH_2$)$_2$N(R)(R'), —($CH_2$)N(R)(R'), —or $SO_2NRR'$.

Representative examples of compounds of formula I are set forth below in Table 1.

TABLE 1
Examples of Compounds of Formula I:
Cmpd #  Compound
1
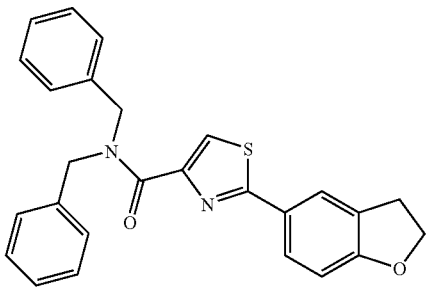
2
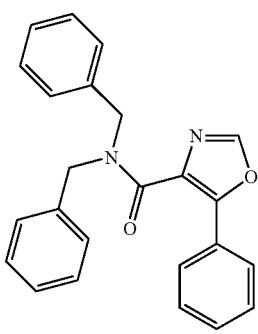
3
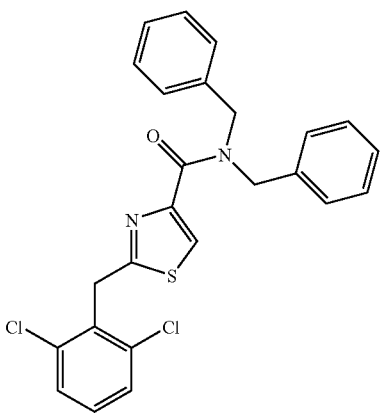
4
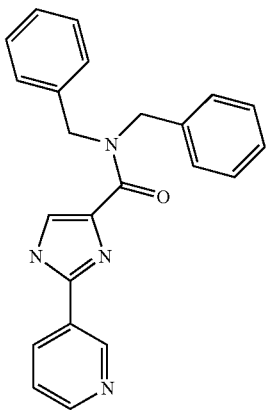

TABLE 1-continued
Examples of Compounds of Formula I:
| Cmpd # | Compound |
|---|---|
| 5 | 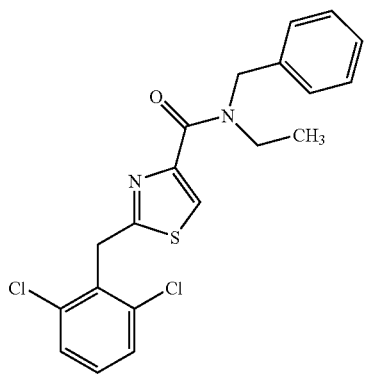 |
| 6 | 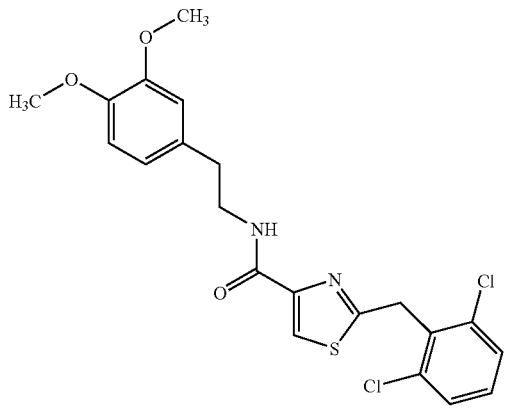 |
| 7 | 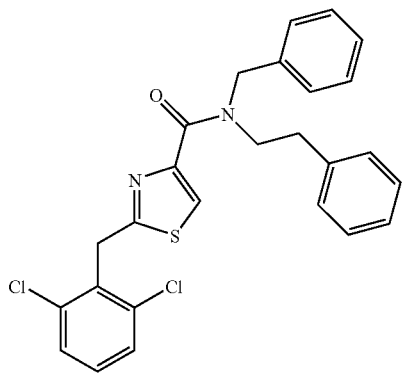 |
| 8 | 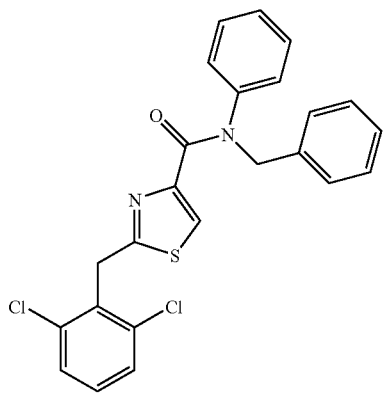 |

TABLE 1-continued
Examples of Compounds of Formula I:
Cmpd # Compound
9
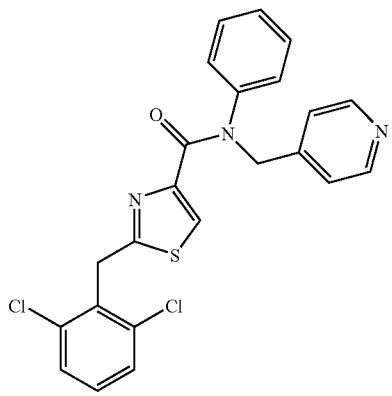
10
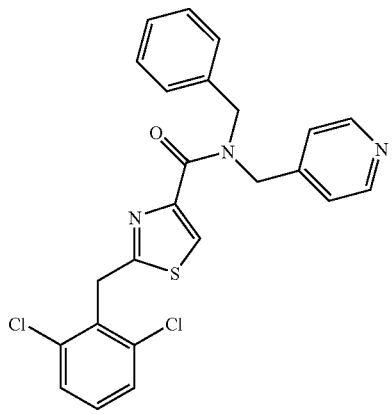
11
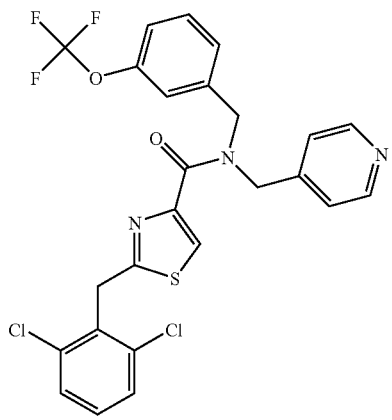

TABLE 1-continued
Examples of Compounds of Formula I:
Cmpd # Compound
12
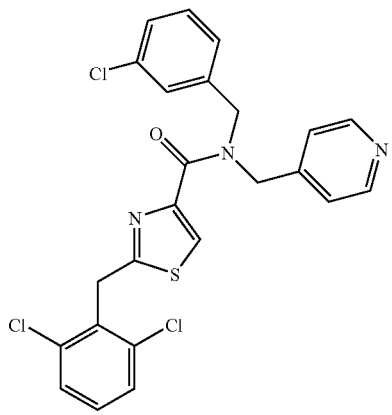
13
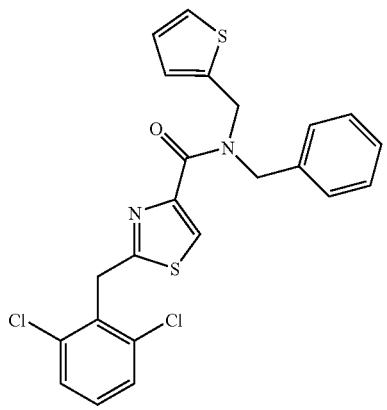
14
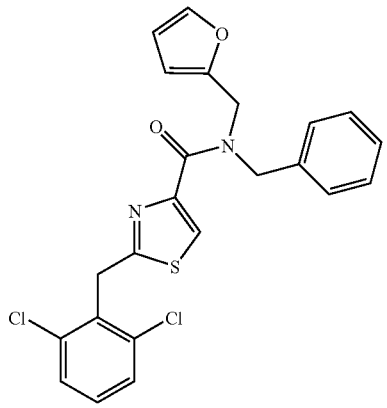

TABLE 1-continued
Examples of Compounds of Formula I:
Cmpd # Compound
15 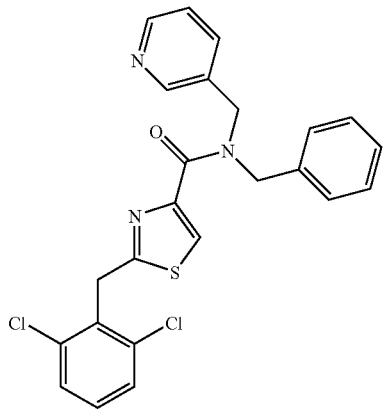
16 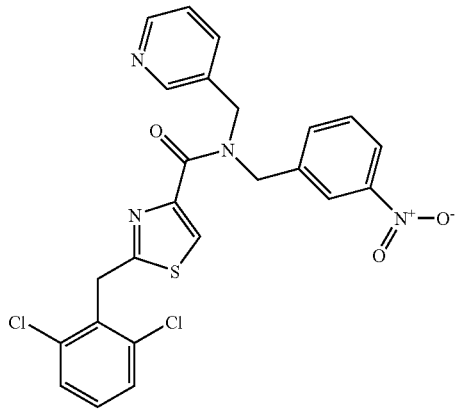
17 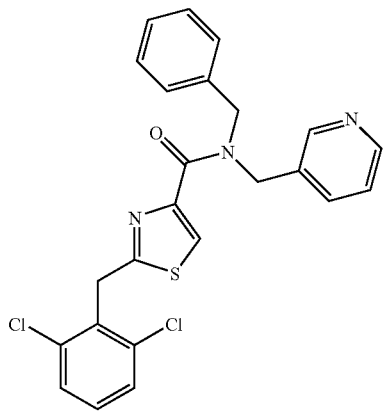

TABLE 1-continued
Examples of Compounds of Formula I:
Cmpd # Compound
18
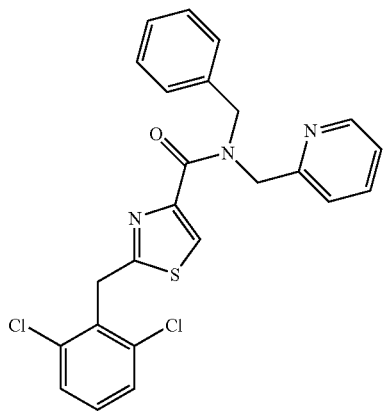
19
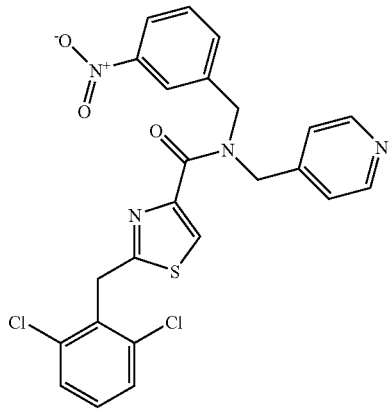
20
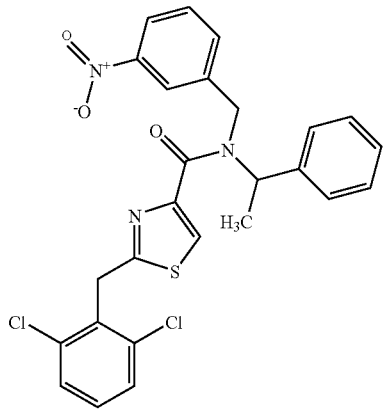

TABLE 1-continued
Examples of Compounds of Formula I:
Cmpd # Compound
21 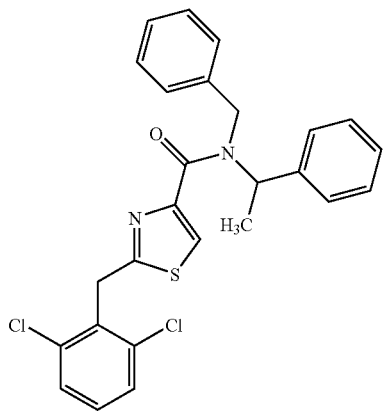
22 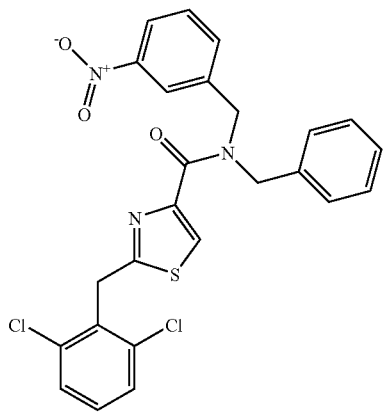
23 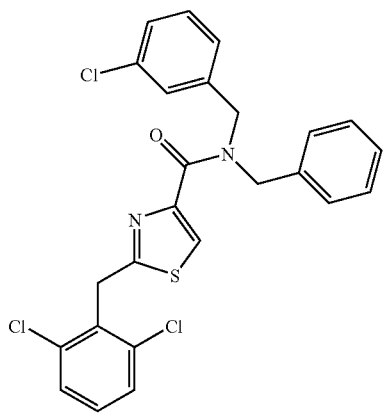

TABLE 1-continued
Examples of Compounds of Formula I:
Cmpd # Compound
24
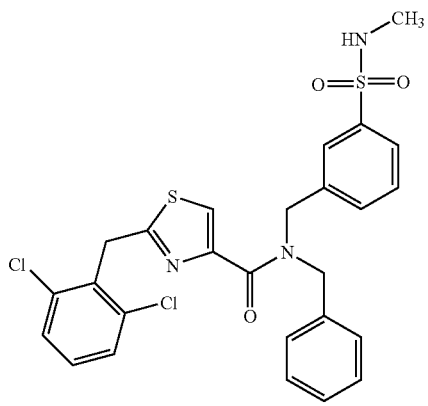
25
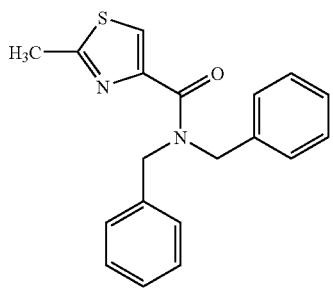
26
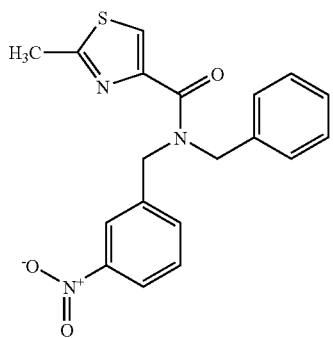
27
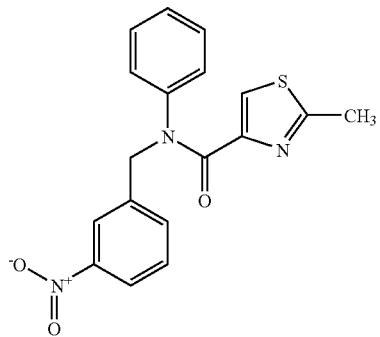

TABLE 1-continued
Examples of Compounds of Formula I:
Cmpd # Compound
28 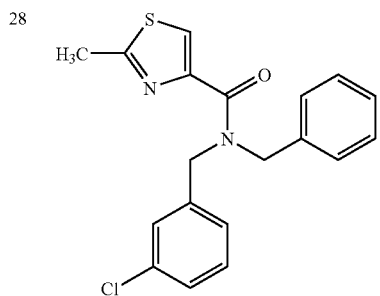
29 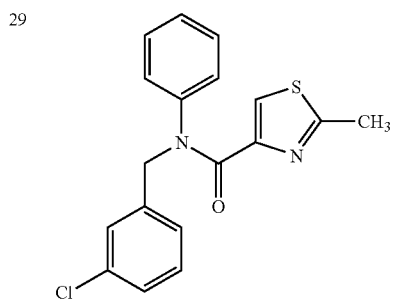
30 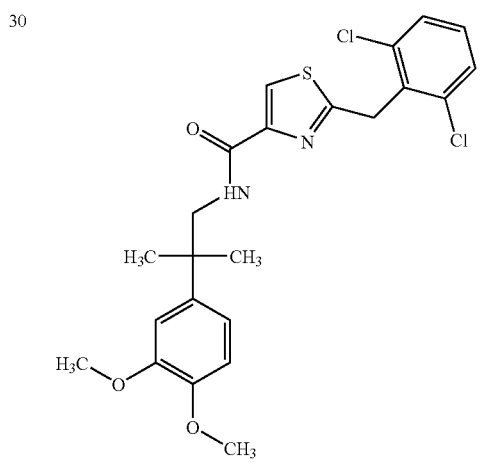
31 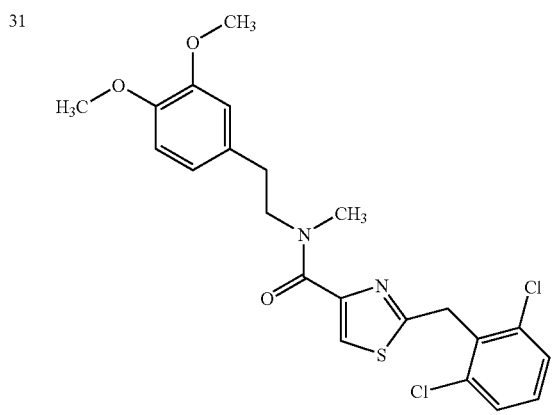

TABLE 1-continued
Examples of Compounds of Formula I:
Cmpd # Compound
32 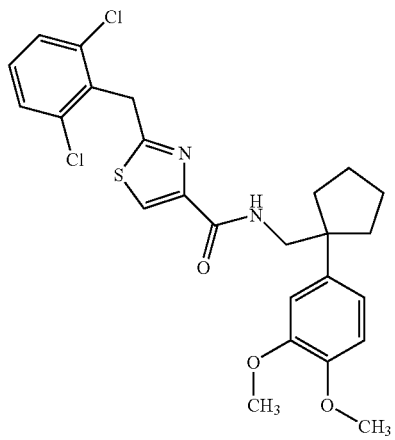
33 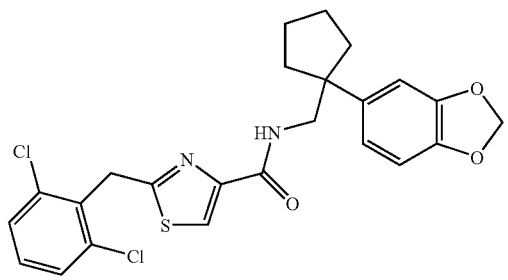
34 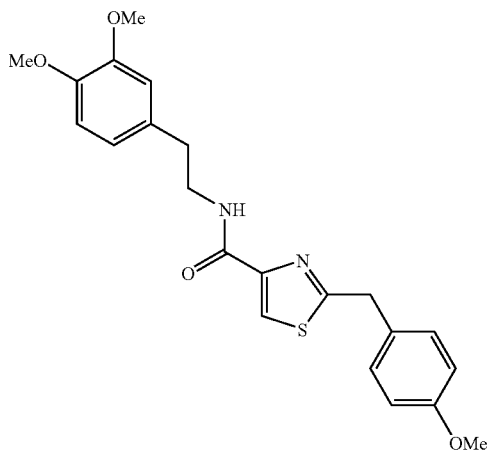

TABLE 1-continued
Examples of Compounds of Formula I:
Cmpd # Compound
35
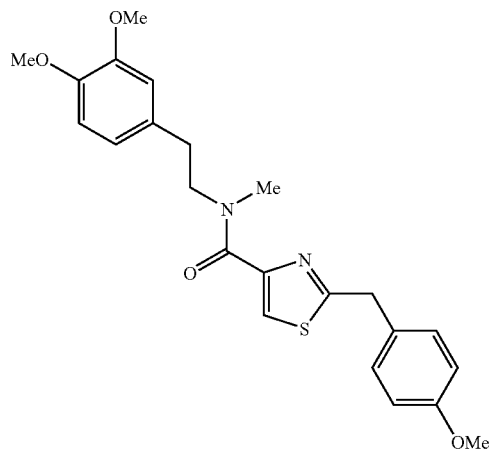
36
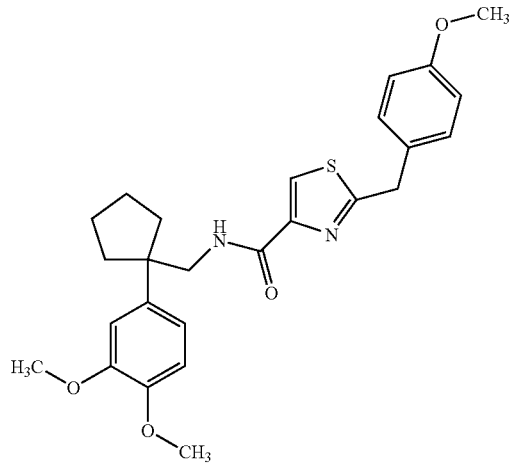
37
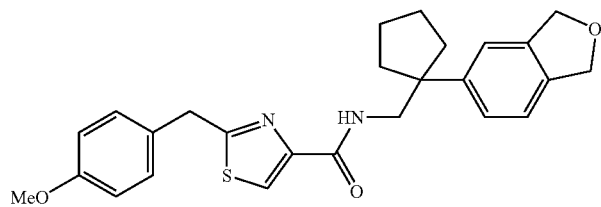

TABLE 1-continued
Examples of Compounds of Formula I:
Cmpd # Compound
38
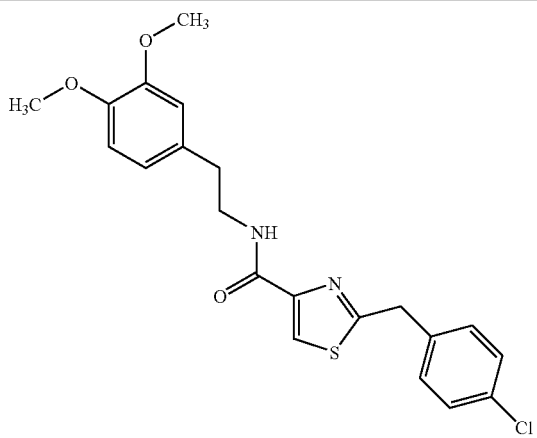
39
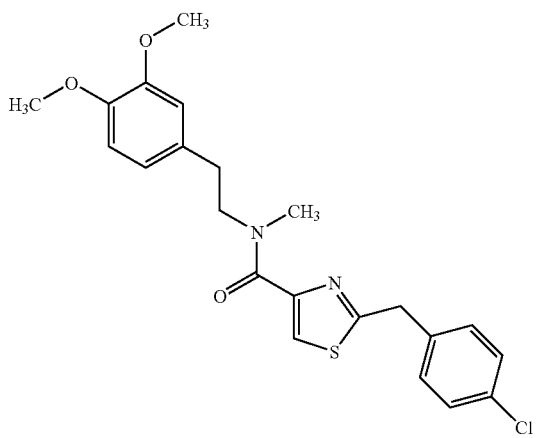
40
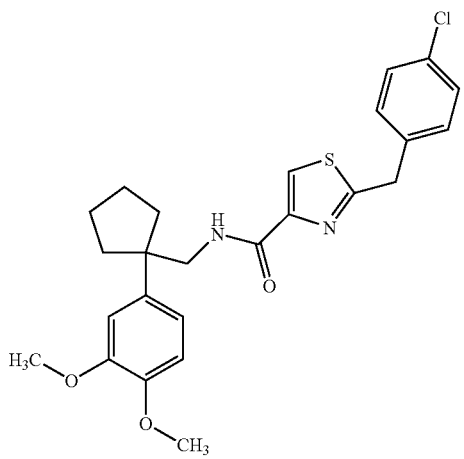
41
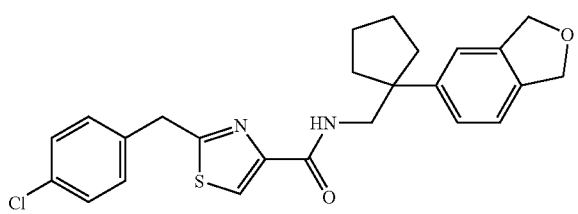

TABLE 1-continued
Examples of Compounds of Formula I:
Cmpd # Compound
42 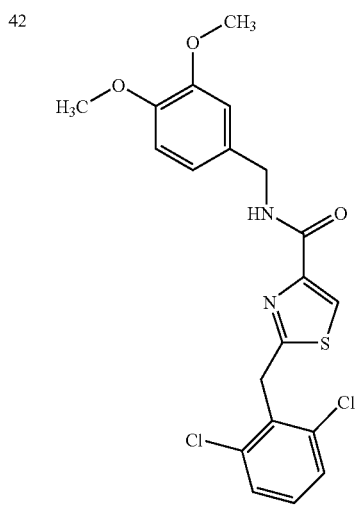
43 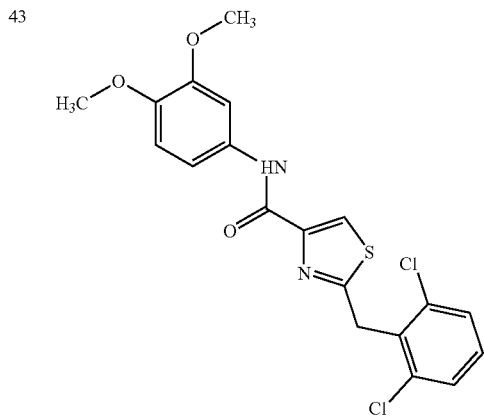
44 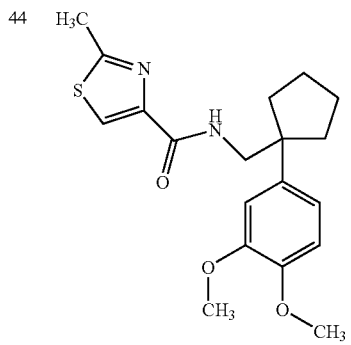

TABLE 1-continued
Examples of Compounds of Formula I:
| Cmpd # | Compound |
|---|---|
| 45 | 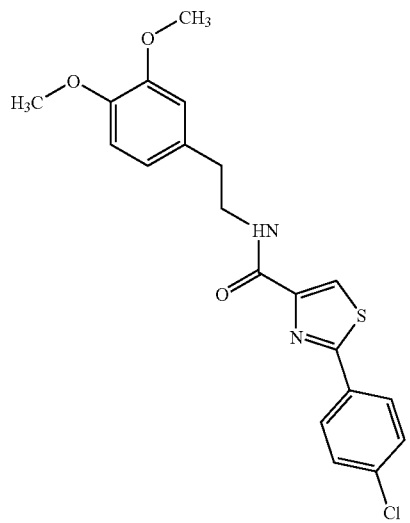 |
| 46 | 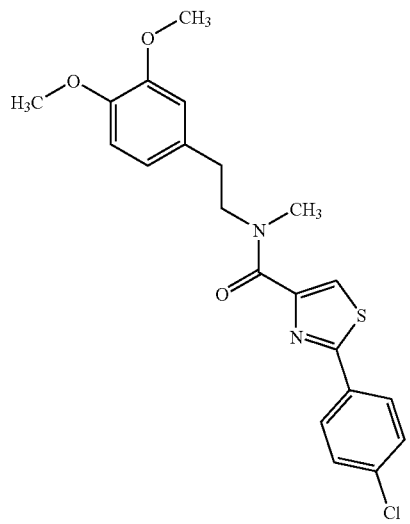 |
| 47 | 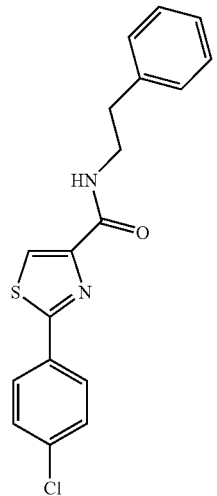 |

TABLE 1-continued
Examples of Compounds of Formula I:
Cmpd #  Compound
48 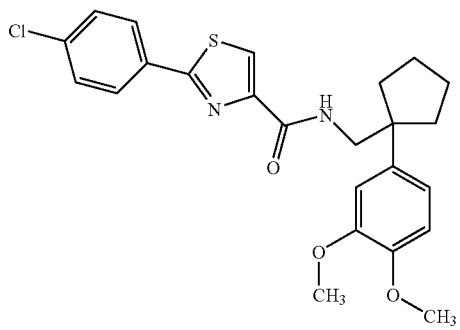
49 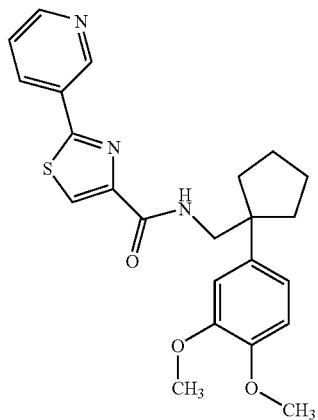
50 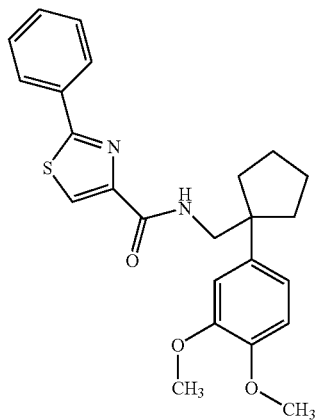

TABLE 1-continued
Examples of Compounds of Formula I:
Cmpd # Compound
51 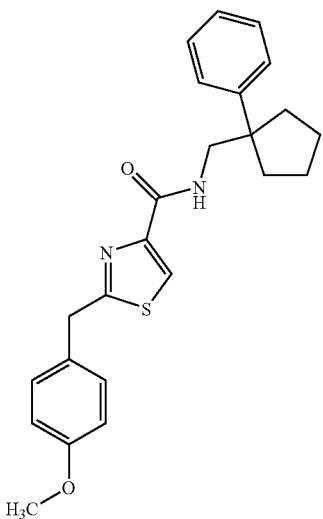
52 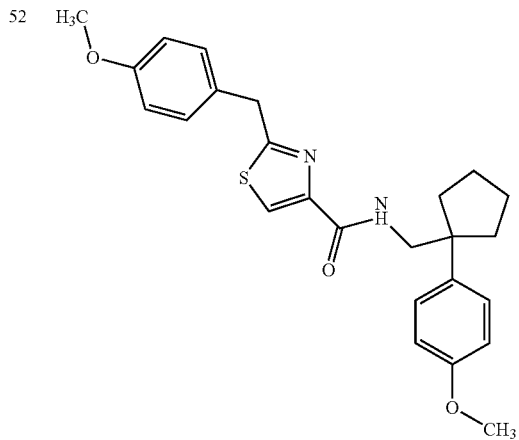
53 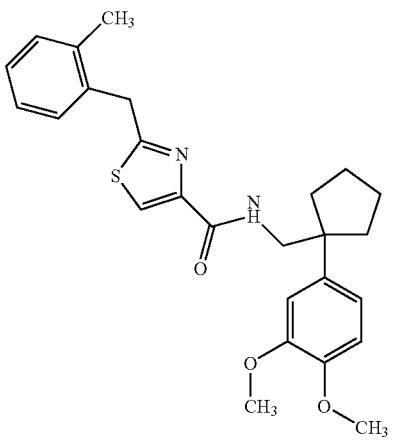

TABLE 1-continued
Examples of Compounds of Formula I:
Cmpd # Compound
54
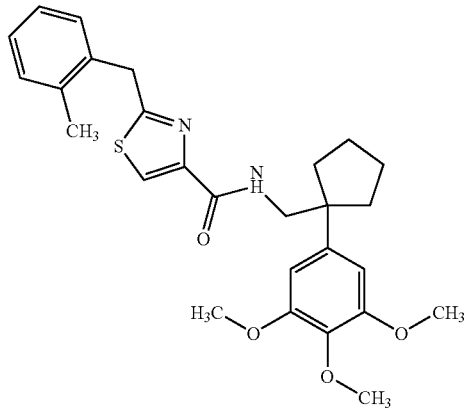
55
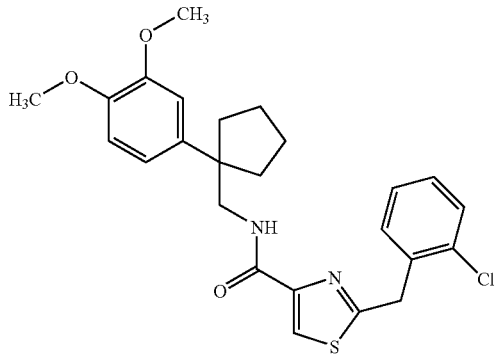
56
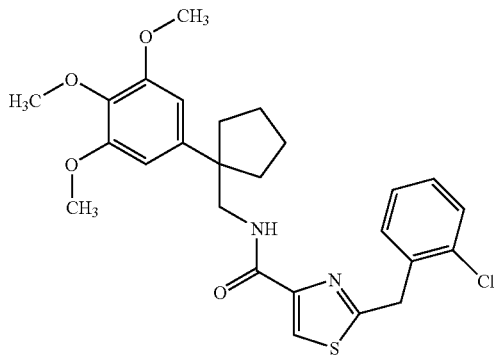
57
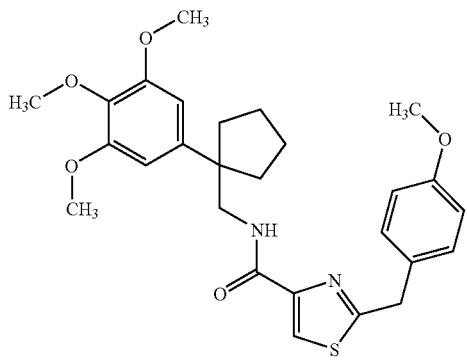

TABLE 1-continued
Examples of Compounds of Formula I:
Cmpd # Compound
58
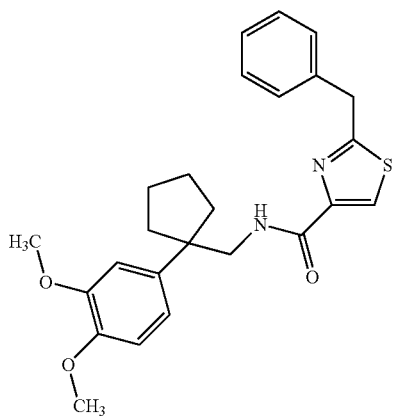
59
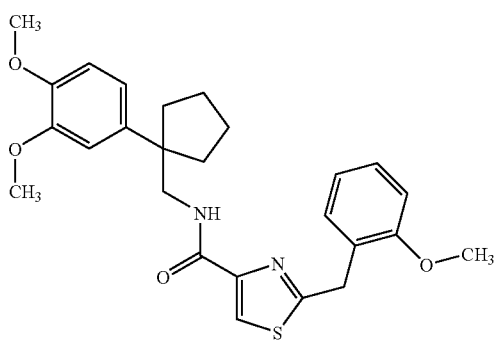
60
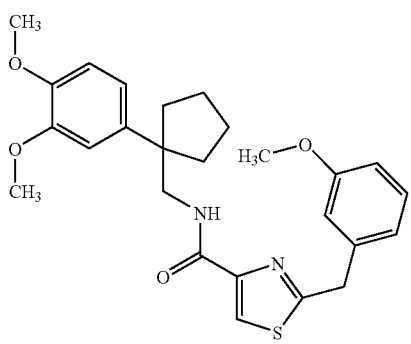
61
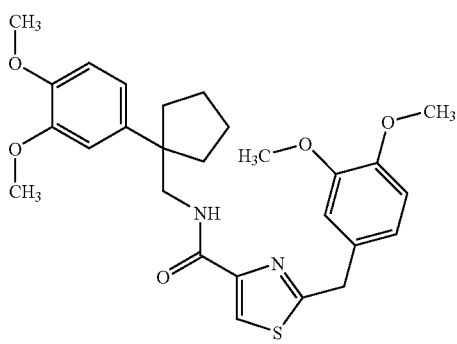

TABLE 1-continued
Examples of Compounds of Formula I:
Cmpd # Compound
62
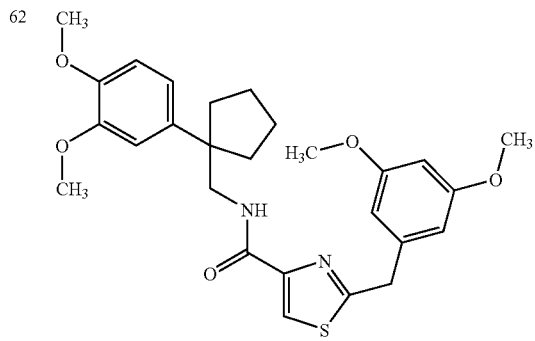
63
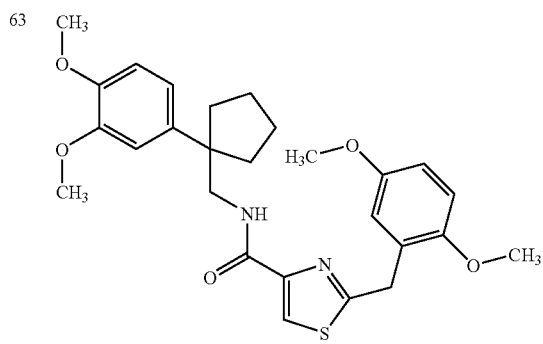
64
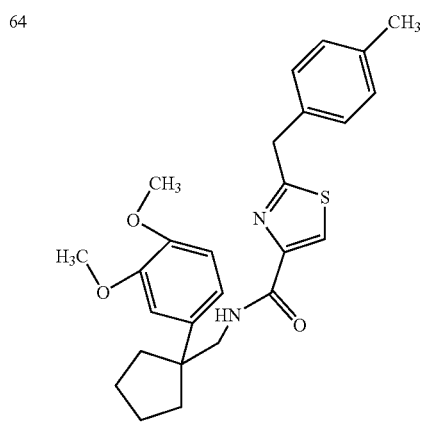

TABLE 1-continued
Examples of Compounds of Formula I:
Cmpd # Compound
65 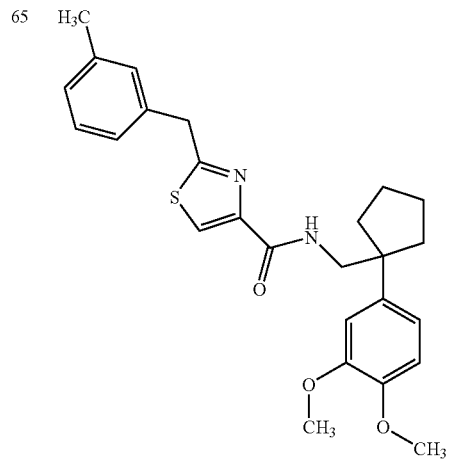
66 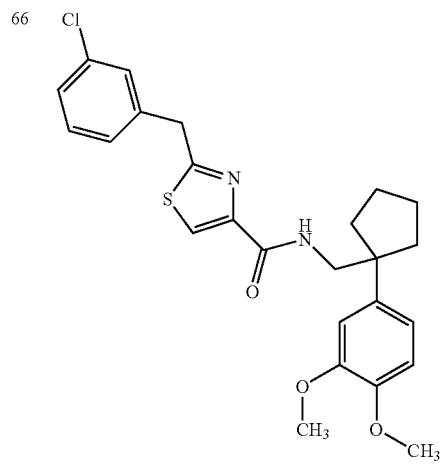
67 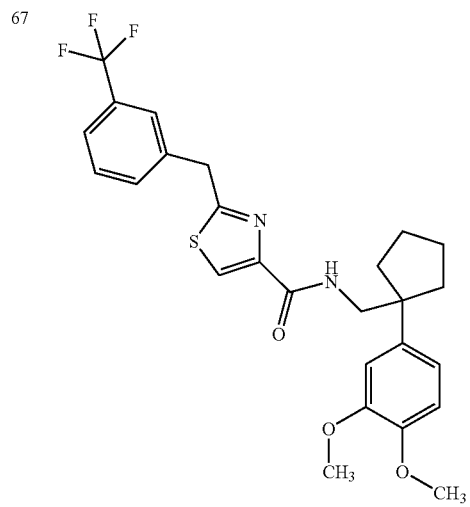

TABLE 1-continued
Examples of Compounds of Formula I:
Cmpd # Compound
68 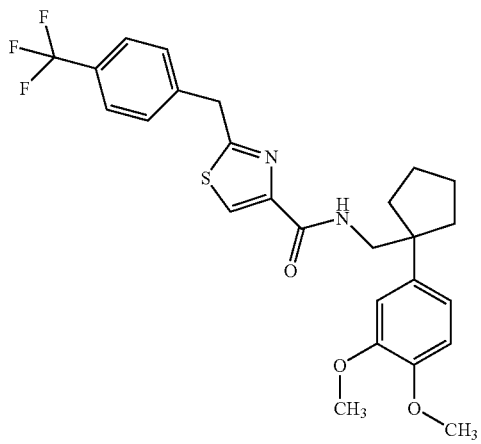
69 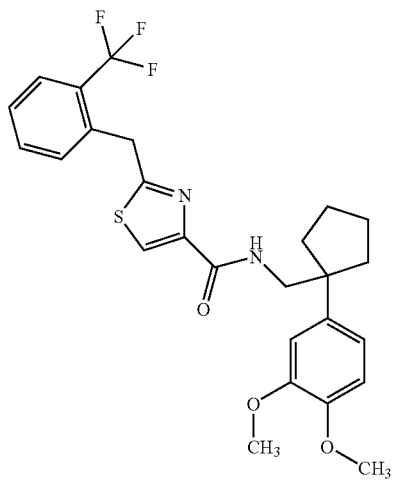
70 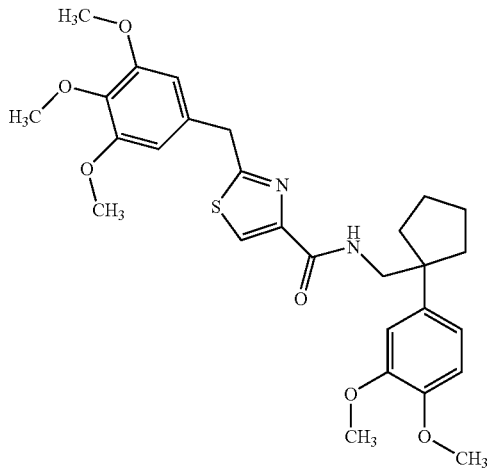

TABLE 1-continued
Examples of Compounds of Formula I:
Cmpd # Compound
71 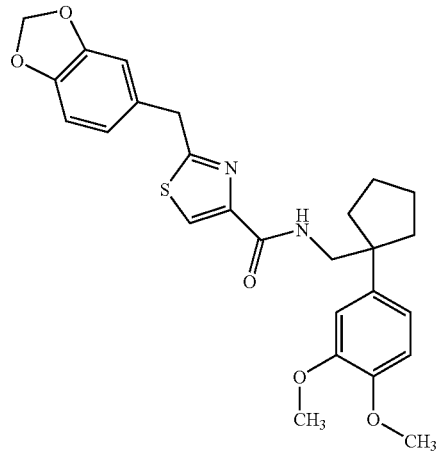
72 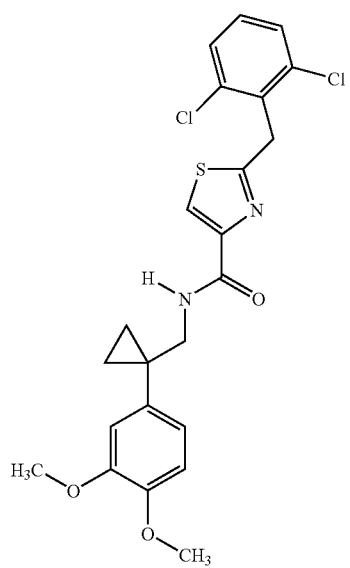
73 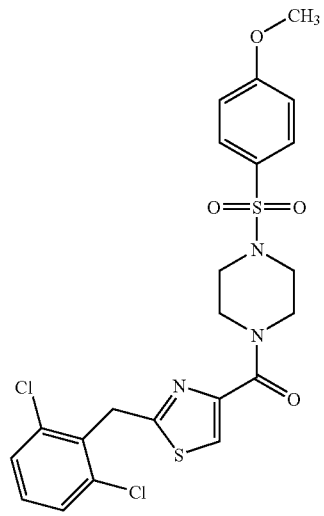

TABLE 1-continued
Examples of Compounds of Formula I:
Cmpd # Compound
74
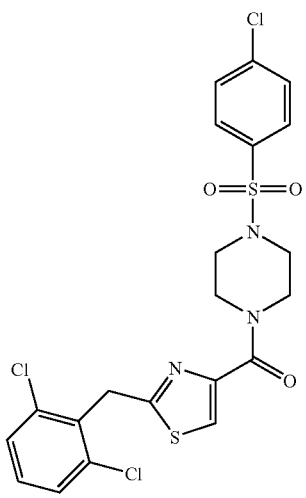
75
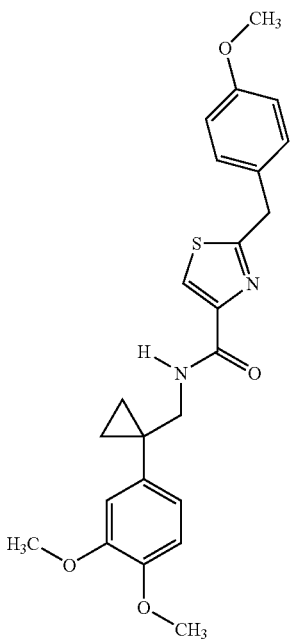
76
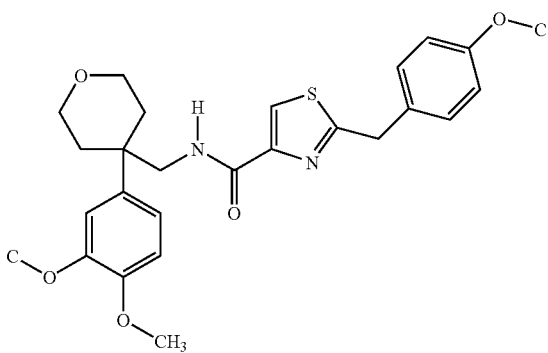

TABLE 1-continued
Examples of Compounds of Formula I:
Cmpd # Compound
77
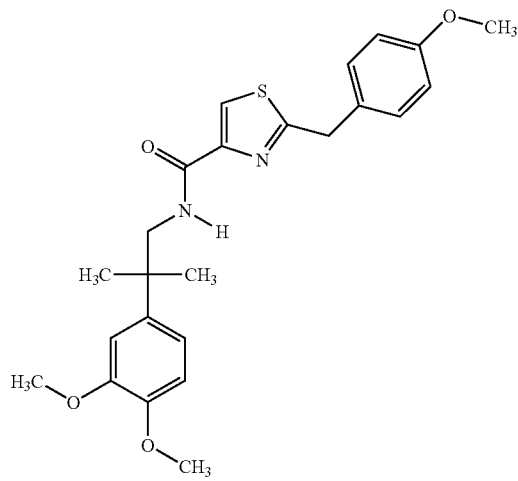
78
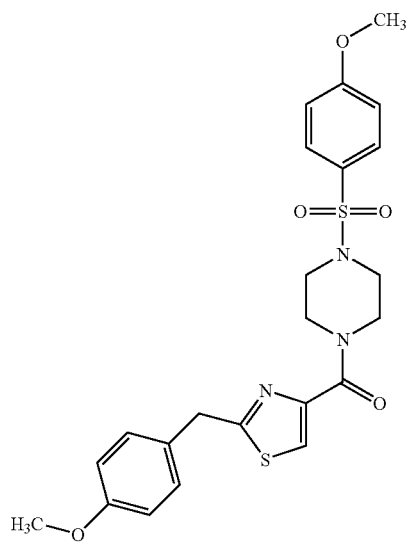
79
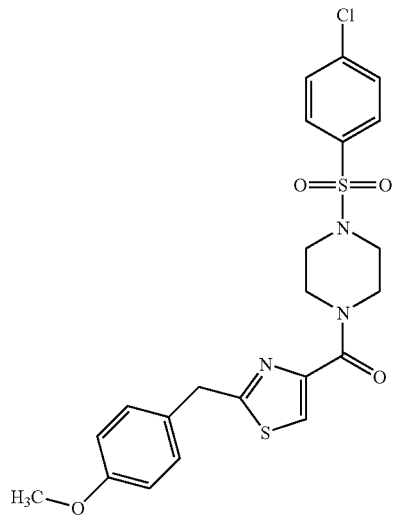

TABLE 1-continued
Examples of Compounds of Formula I:
Cmpd # Compound
80
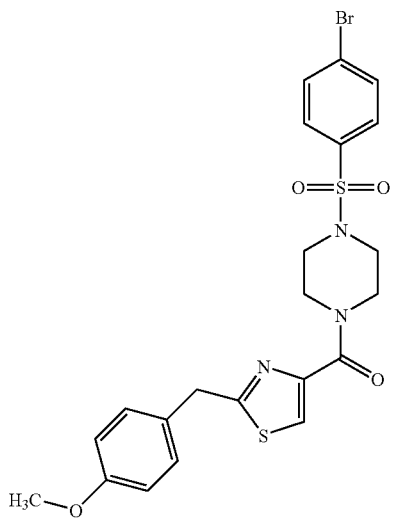
81
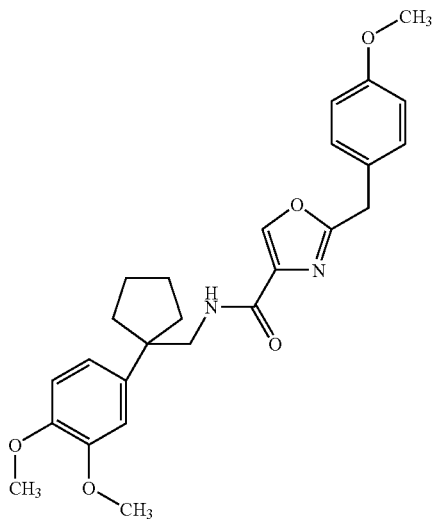
82
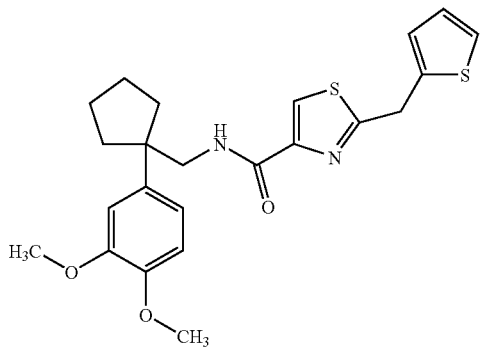

TABLE 1-continued
Examples of Compounds of Formula I:
Cmpd # Compound
83
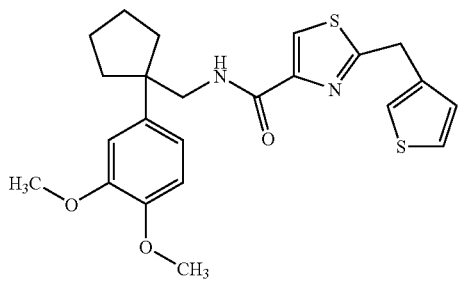
84
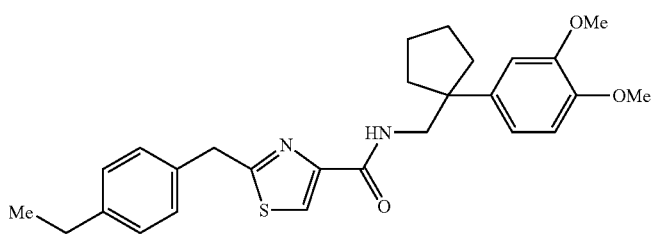
85
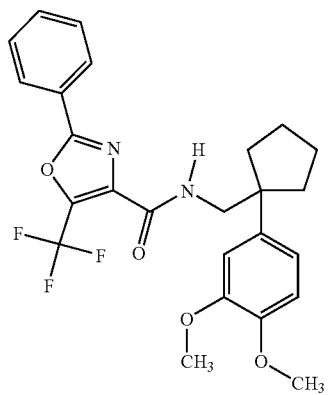
86
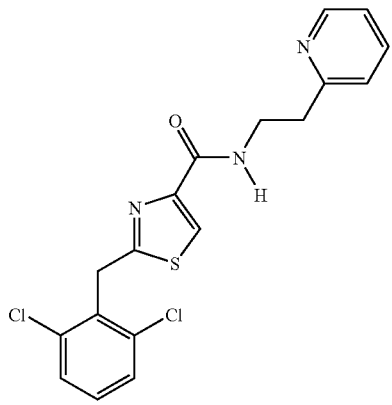

TABLE 1-continued
Examples of Compounds of Formula I:
Cmpd #  Compound
87
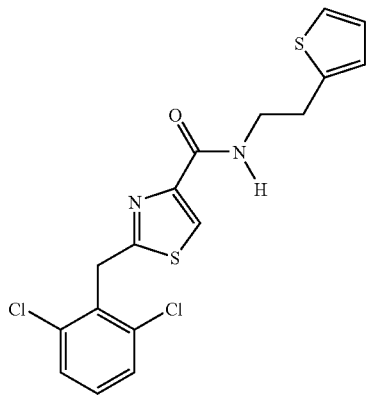
88
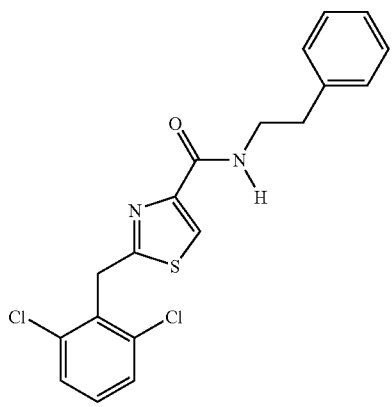
89
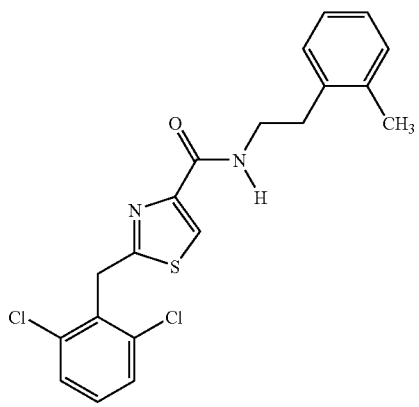

TABLE 1-continued
Examples of Compounds of Formula I:
Cmpd # Compound
90
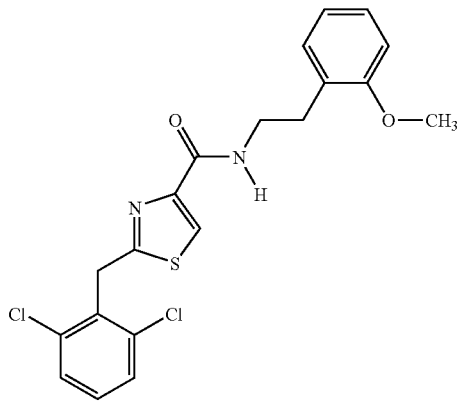
91
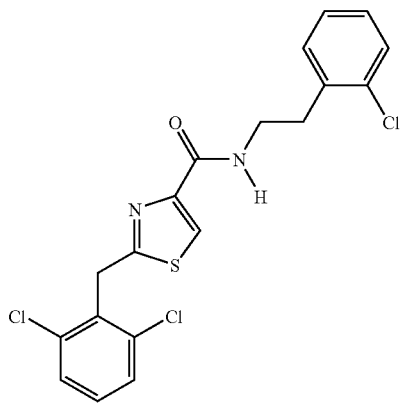
92
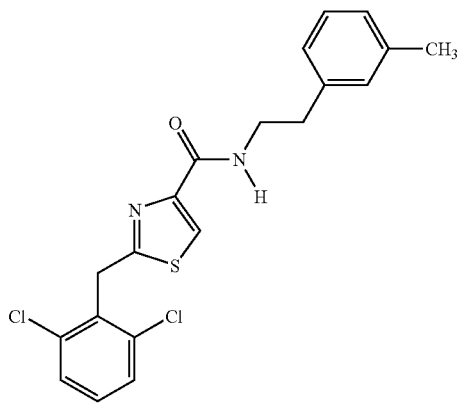

TABLE 1-continued
Examples of Compounds of Formula I:
Cmpd # Compound
93
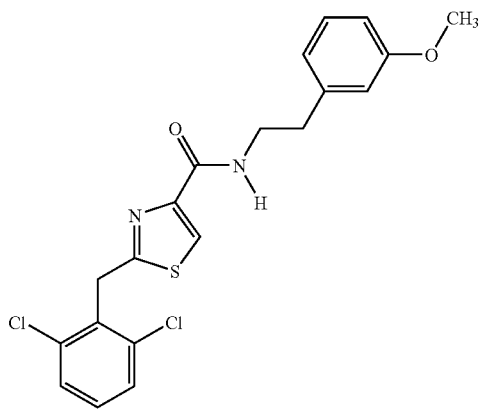
94
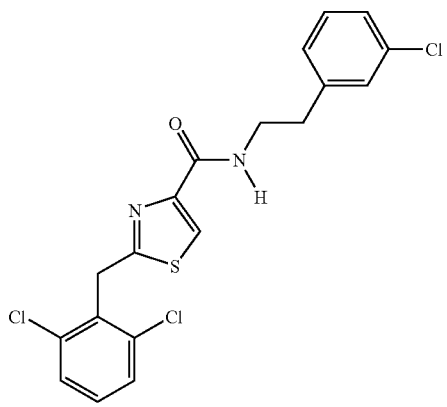
95
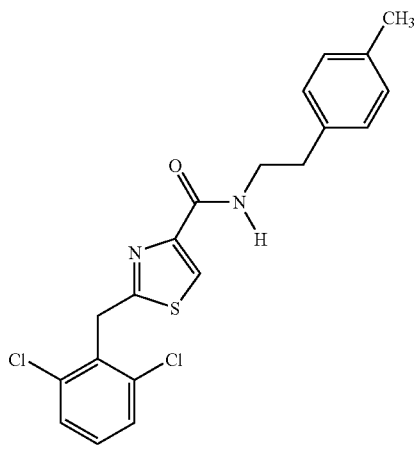

TABLE 1-continued
Examples of Compounds of Formula I:
Cmpd # Compound
96
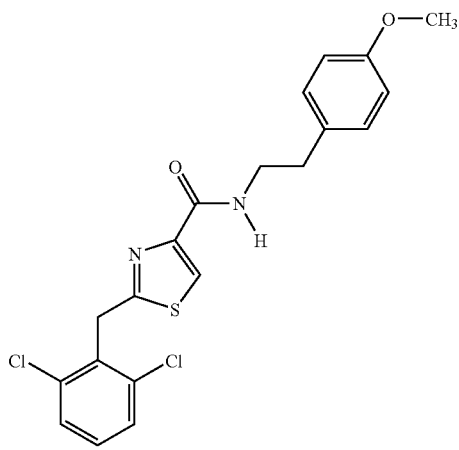
97
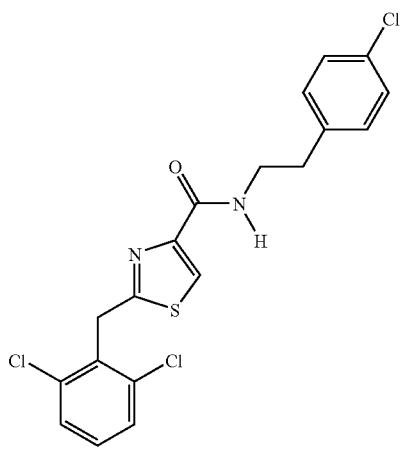
98
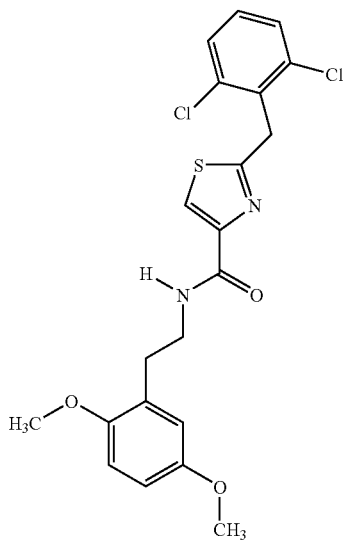

TABLE 1-continued

Examples of Compounds of Formula I:

Cmpd # Compound

99

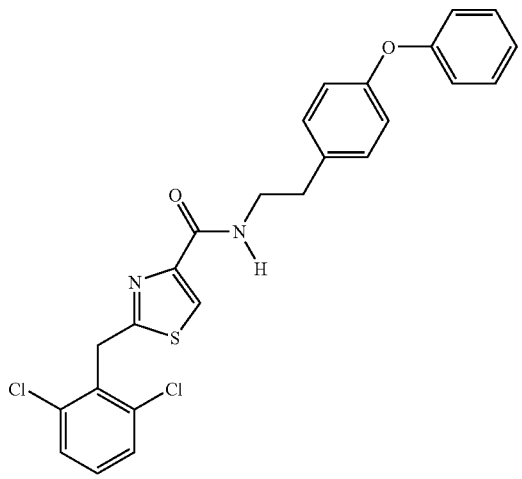

100

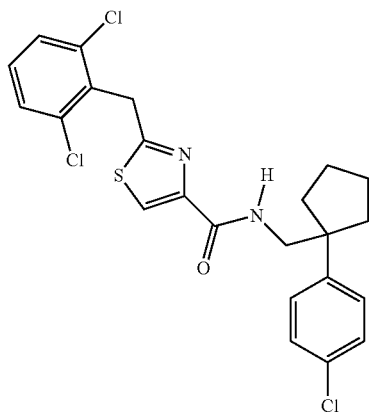

4. General Synthetic Methodology:

The compounds of this invention may be prepared in general by methods known to those skilled in the art for analogous compounds, as illustrated by the general scheme below, and the preparative examples that follow.

Schemes I and II below depict the synthesis of thiazole and oxazole starting materials where Z is —CH$_2$— and R$^1$ is optionally substituted phenyl.

Scheme I:

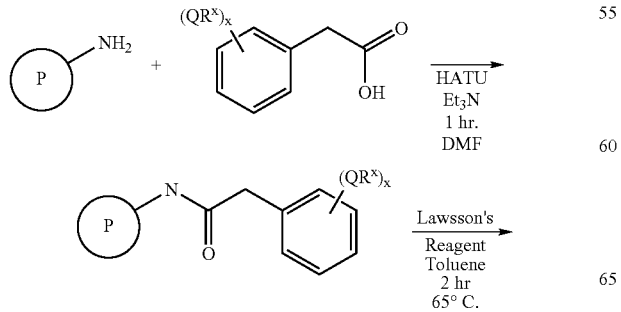

-continued

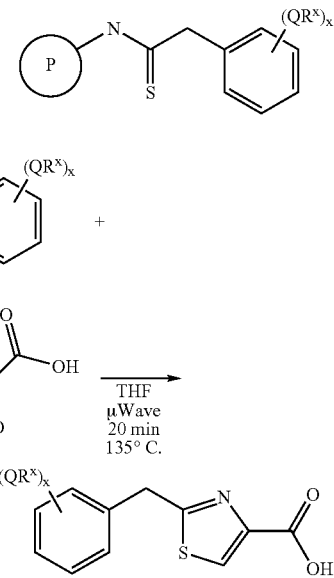

Scheme II:

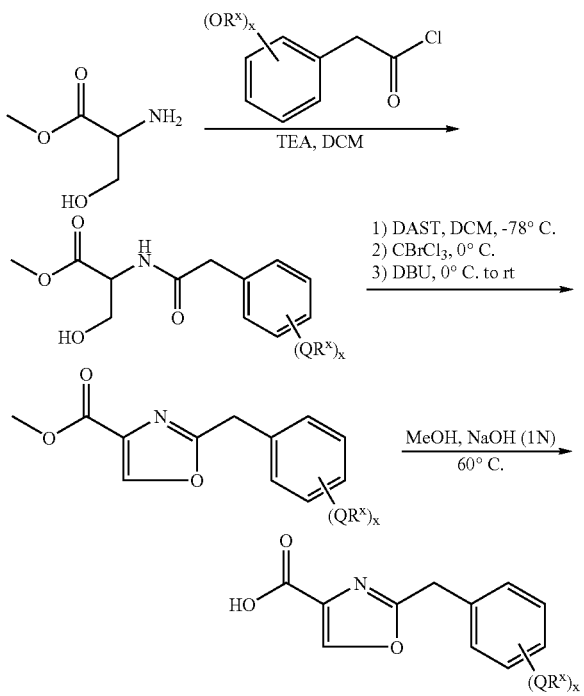

References:

*Org. Lett.*, 2000, 2(8), 1165-1168; A. J. Phillips et al.

*Chem Pharm Bull*, 1986, 34(7), 2851; K. Meguro et al.

Scheme III:

Scheme III depicts general reaction conditions for the coupling of the thiazole or oxazole starting materials (as depicted generally above) and an appropriate amine to generate thiazole or oxazole amides as represented generally by compounds of formula I.

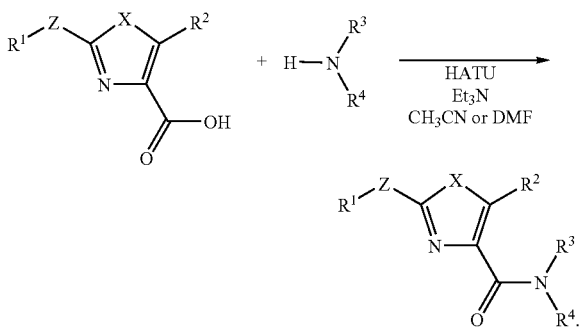

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are useful as modulators of ABC transporters and thus are useful in the treatment of disease, disorders or conditions such as cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

The compounds and compositions, according to the method of the present invention, may be administered using any amount and any route of administration effective for treating or lessening the severity of one or more of cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I); and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

A): Preparation of Certain Exemplary Compounds of the Invention:

General Experimental Procedures:

Amides Preparation: If the appropriate acid chloride was commercially available, it was added to one equivalent of the appropriate secondary amine in minimum of 1,4-dioxane containing two equivalents triethylamine. The reaction mixture was allowed to stir overnight at room temperature. The reaction mixture was then filtered and evaporated to dryness. The crude product was purified by reverse phase preparative mass-directed liquid chromatography/mass spectrometry.

If the appropriate acid chloride was not commercially available the appropriate carboxylic acid was added to a solution containing one equivalent of the appropriate amine in a minimum of acetonitrile containing two equivalents of triethylamine. O-(7-Azabenzotriazol-1-yl)-N,N,N',N'-tetramethyluronium hexafluorophosphate (HATU, 1.2 eq.) is added, and the reaction is stirred overnight. The crude product was then purified by reverse phase preparative mass-directed liquid chromatography/mass spectrometry.

Specific Examples

General. All reagents and solvents were used as received without further purification. Thin layer chromatography was performed on glass-backed silica gel 60 plates pre-coated with a fluorescent dye from EM Science. Mass spectrometry was performed in the positive mode on a PE SCIEX EX150 mass spectrometer. Purity was determined by the observed total ion current, and the ultraviolet absorption at 220 nm and 254 nm Preparation of Amines:

C-[1-(3,4-Dimethoxy-phenyl)-cyclopentyl]-methylamine: (3,4-Dimethoxy-phenyl)-acetonitrile (5.00 g, 28.2 mmol) was dissolved in 60 mL of anhydrous tetrahydrofuran in a 250 mL round bottom flask. Sodium hydride (2.03 g, 84.6 mmol) was slowly added and the reaction mixture was warmed to 50-60° C. 1,4-Dichlorobutane (4.30 g, 33.9 mmol) was then added and the reaction mixture was heated to reflux for 16 hours. An additional aliquot of 1,4-dichlorobutane (4.30 g, 33.9 mmol) was added and the reaction mixture was refluxed for an additional 24 hours. The reaction mixture was cooled to room temperature and quenched with the slow addition of methanol. The reaction mixture was evaporated to dryness and purified by column chromatography on silica gel to yield a pale yellow oil (1.61 g, 6.98 mmol, 24.8%). The resulting 1-(3,4-dimethoxy-phenyl)-cyclopentanecarbonitrile (363 mg, 1.57 mmol) was dissolved in dry ether (4 mL) and cooled to 0° C. under an atmosphere of nitrogen. Lithium aluminum hydride (1.57 mL, 1 M in ether) was slowly added and the reaction mixture was allowed to warm to room temperature and stirred for 16 hours. The reaction mixture was quenched with the slow addition of methanol. The reaction mixture was washed with a saturated aqueous sodium chloride solution, separated, and evaporated to dryness to give a colorless oil (356 mg, 1.38 mmol, 87.9%). ESI-MS m/z calc. 235.3, found 236.2 (M+1)$^+$. Retention time of 1.64 minutes.

Preparation of Amides:

2-(4-Methoxy-benzyl)-thiazole-4-carboxylic acid [1-(3,4-dimethoxy-phenyl)-cyclopentylmethyl]-amide: 2-(4-Methoxy-benzyl)-thiazole-4-carboxylic acid (101 mg, 0.405 mmol) and C-[1-(3,4-Dimethoxy-phenyl)-cyclopentyl]-methylamine (96.5 mg, 0.410 mmol) were dissolved in acetonitrile (2 mL) containing triethylamine (84.1 μL, 0.600 mmol). O-(7-Azabenzotriazol-1-yl)-N,N,N',N'-tetramethyluronium hexafluorophosphate (171 mg, 0.450 mmol) was added and the solution was allowed to stir for 16 hours. The reaction mixture was evaporated to dryness and purified by column chromatography on silica gel using a gradient of 5-30% ethyl acetate in hexanes. The pure fractions were combined and evaporated to dryness to yield a yellow solid (84.0 mg, 0.180 mmol, 43.9%). ESI-MS m/z calc. 466.6, found 467.2 (M+1)$^+$. Retention time of 8.32 minutes. $^1$H NMR (400 MHz, CD$_3$CN) δ1.68-2.07 (m, 8H), 3.50 (d, J=6.3 Hz, 2H), 3.82 (s, 9H), 4.20 (s, 2H), 6.83-7.29 (m, 8H), 7.87 (s, 1H).

2-Benzyl-thiazole-4-carboxylic acid [2-(3,4-dimethoxy-phenyl)-ethyl]-amide. Rink amide resin (0.627 g, 0.752 mmol, 1.20 mmol/g) was suspended and allowed to swell for 10 minutes in 4 mL of N,N-dimethylformamide (DMF). Phenylacetic acid (0.15 g, 1.1 mmol) and triethylamine (0.21 mL, 1.5 mmol) were then added to the reaction mixture. O-(7-Azabenzotriazol-1-yl)-N,N,N',N'-tetramethyluronium hexafluorophosphate (HATU, 0.46 g, 1.2 mmol) was added and the reaction mixture was swirled for two hours, filtered, and washed with DMF and dichloromethane. The resin was then suspended in 5 mL of toluene and 2,4-bis-(4-methoxyphenyl)-1,3-dithia-2,4-diphosphetane-2,4-disulfide (Lawesson's Reagent, 0.93 g, 2.3 mmol) was added to the suspension. The reaction mixture was then swirled for 2 hours at 65° C., filtered, and washed with DMF and dichloromethane. The resin (0.50 g, 0.60 mmol) was then allowed to swell in 5 mL of tetrahydrofuran for 10 minutes and bromopyruvic acid (0.060 g, 0.36 mmol) was added to the reaction mixture. The mixture was then subjected to microwave irradiation for 20 minutes at 135° C., and followed by filtration to yield crude 2-benzyl-thiazole-4-carboxylic acid. MS m/z calc. 219.0, found (ESI); 220.2 (M+H$^+$). Retention time 2.38 minutes. The crude acid was dissolved in 2 mL of acetonitrile containing triethylamine (0.0836 mL, 0.600 mmol) and 2-(3,4-dimethoxy-phenyl)-ethylamine (0.0332 mL, 0.200 mmol). O-(7-Azabenzotriazol-1-yl)-N,N,N',N'-tetramethyluronium hexafluorophosphate (0.0836 g, 0.220 mmol) was added and the solution was allowed to stir for 16 hours. The reaction mixture was then purified by reverse-phase preparative liquid chromatography to yield (0.011 g, 0.029 mmol, 4.8%) a colorless oil. MS m/z calc. 382.1, found (ESI); 383.2 (M+H$^+$) Retention time 2.97 minutes. $^1$H NMR (400 MHz, CD$_3$CN) δ2.85 (t, J=7.0 Hz, 2H), 3.53-3.65 (m, 2H), 3.78 (s, 3H), 3.80 (s, 3H), 4.33 (s, 2H), 6.78-6.91 (m, 3H), 7.29-7.42 (m, 5H), 7.52 (s, 1H), 7.92 (s, 1H)

2-(4-Methoxy-benzyl)-oxazole-4-carboxylic acid [1-(3,4-dimethoxy-phenyl)-cyclopentylmethyl]-amide:

3-Hydroxy-2-[2-(4-methoxy-phenyl)-acetylamino]-propionic acid methyl ester: to a suspension of DL-serine HCl (2.0 g, 12.8 mmol) in dichloromethane (10 mL) at 0° C. were added dropwise triethylamine (3.58 mL, 25.7 mmol) and (4-methoxyphenyl)-acetyl chloride (1.96 mL, 12.8 mmol). The mixture was stirred at 25° C. for 12 hours. The reaction mixture was washed with a saturated aqueous sodium chloride solution, separated, and evaporated to dryness and purified by column chromatography (hexanes: ethyl acetate from 25 to 100%). 3-Hydroxy-2-[2-(4-methoxy-phenyl)-acetylamino]-propionic acid methyl ester was isolated as a white solid (2g, 58%). ESI-MS m/z calc. 267.3, found 268.2 (M+1)$^+$. Retention time of 1.83 minutes. $^1$H NMR (400 MHz, CDCl$_3$) δ3.64 (s, 2H), 3.78 (s, 3H), 3.83 (s, 3H), 3.93 (qd, J=14.6 and 4.0 Hz, 2H), 4.66 (m, 1H), 6.40 (m, 1H), 7.01 (d, J=8.7 Hz, 2H), 7.23 (d, J=8.7 Hz, 2H).

2-(4-Methoxy-benzyl)-oxazole-4-carboxylic acid methyl ester: DAST (diethylaminosulfur trifluoride) was added to a cold (−78° C.) solution of 3-hydroxy-2-[2-(4-methoxy-phenyl)-acetylamino]-propanoic acid methyl ester (400 mg, 1.5 mmol) in dichloromethane (8 mL). After stirring for 1 h at −78° C., CCl$_3$Br (149 μL, 1.5 mmol) and DBU (226 μL, 1.5 mmol) were added and the reaction was allowed to warm to 25° C. and stirred at this temperature for 12h. The reaction was poured into saturated aqueous NaHCO$_3$ and the biphasic mixture was extracted with DCM. The combined organic extracts were dried with MgSO$_4$ and purified by column chromatography (hexanes: ethyl acetate from 25 to 100%). 2-(4-Methoxy-benzyl)-oxazole-4-carboxylic acid methyl ester was isolated as a white solid (80 mg, 21%). ESI-MS m/z calc. 247.5, found 248.2 (M+1)$^+$. Retention time of 2.64 minutes. $^1$H NMR (400 MHz, CDCl$_3$) δ3.80 (s, 3H), 3.92 (s, 3H), 4.12 (s, 2H), 6.87 (d, J=8.0 Hz, 2H).

2-(4-Methoxy-benzyl)-oxazole-4-carboxylic acid: A mixture of 2-(4-Methoxy-benzyl)-oxazole-4-carboxylic acid methyl ester (40 mg, 0.16 mmol), methanol (2 mL) and 1N NaOH (1 mL) was heated at 60° C. for 2 hours and allowed to stand at 25° C. for 30 minutes. After dilution with water, the mixture was adjusted to pH 2 with 2N HCl and extracted with ether. The organic layers were combined, dried with MgSO$_4$ and evaporated to dryness to yield 25 mg (66%) of 2-(4-Methoxy-benzyl)-oxazole-4-carboxylic acid as a white solid. ESI-MS m/z calc. 233.2, found 234.2 (M+1)$^+$. Retention time of 2.27 minutes.

2-(4-Methoxy-benzyl)-oxazole-4-carboxylic acid [1-(3,4-dimethoxy-phenyl)-cyclopentylmethyl]-amide: Starting from 2-(4-Methoxy-benzyl)-oxazole-4-carboxylic acid 25 g, 0.1 mmol) and [2-(3,4-Dimethoxy-phenyl)-2-methyl]-propylamine (47 mg, 0.2 mmol) following a similar procedure reported for the preparation of 2-(4-Methoxy-benzyl)-thiazole-4-carboxylic acid[1-(3,4-dimethoxy-phenyl)-cyclopentylmethyl]-amide, the amide (30 mg, 66%) was obtained as a white solid. ESI-MS m/Z calc. 450.5, found 451.2(M+1)$^+$. Retention time of 3.51 minutes $^1$H NMR (400 MHz, CDCl$_3$) δ1.68-2.19 (m, 8H), 3.50 (d, J=6.3 Hz, 2H), 3.81 (s, 3H), 3.88 (s, 3H), 3.92 (s, 3H), 4.00 (s, 2H), 6.73-6.88 (m, 6H), 7.20 (d, J=8.7 Hz, 2H), 8.07 (s, 1H).

Other compounds of formula I have been prepared by methods substantially similar to those described above. Table 2 below recites analytical data for selected compounds of formula I.

TABLE 2

| Cmpd # | LC-MS (M + 1)+ | LC-RT (min) |
|---|---|---|
| 6 | 451.20 | 3.60 |
| 10 | 468.00 | 3.17 |
| 12 | 502.00 | 3.25 |
| 13 | 473.00 | 4.84 |
| 14 | 457.00 | 4.66 |
| 15 | 454.00 | 4.19 |
| 16 | 499.00 | 4.25 |
| 17 | 468.00 | 3.17 |
| 18 | 468.00 | 3.23 |
| 19 | 513.20 | 3.16 |
| 20 | 422.00 | 4.32 |
| 21 | 377.00 | 4.46 |
| 22 | 512.00 | 4.57 |
| 23 | 501.00 | 4.96 |
| 24 | 560.20 | 4.33 |
| 25 | 323.00 | 4.14 |
| 26 | 368.00 | 4.12 |
| 27 | 354.00 | 3.18 |
| 28 | 357.00 | 3.90 |
| 29 | 343.00 | 3.40 |
| 30 | 479.00 | 4.28 |
| 31 | 465.40 | 3.52 |
| 32 | 505.40 | 4.24 |
| 33 | 489.20 | 4.46 |
| 34 | 413.20 | 3.62 |
| 35 | 427.00 | 3.45 |
| 36 | 467.20 | 4.23 |
| 37 | 451.20 | 4.42 |
| 38 | 417.20 | 3.87 |
| 39 | 431.40 | 3.73 |
| 40 | 471.20 | 4.46 |
| 41 | 455.20 | 4.68 |
| 42 | 437.20 | 3.24 |
| 43 | 423.20 | 3.40 |
| 44 | 361.00 | 2.91 |
| 45 | 403.40 | 3.25 |
| 46 | 417.20 | 3.17 |
| 47 | 343.00 | 3.53 |
| 48 | 457.40 | 3.84 |
| 49 | 424.20 | 2.53 |
| 50 | 423.20 | 3.55 |
| 51 | 407.60 | 3.71 |
| 52 | 437.40 | 3.78 |
| 53 | 451.40 | 3.64 |
| 54 | 481.20 | 3.65 |
| 55 | 471.20 | 3.67 |
| 56 | 501.20 | 3.67 |
| 57 | 497.20 | 3.49 |
| 58 | 437.20 | 3.51 |
| 59 | 467.40 | 3.63 |
| 60 | 467.40 | 3.54 |
| 61 | 497.40 | 3.33 |
| 62 | 497.40 | 3.55 |
| 63 | 497.20 | 3.58 |
| 64 | 451.20 | 3.77 |
| 65 | 451.40 | 3.76 |
| 66 | 471.20 | 3.72 |
| 67 | 505.40 | 3.78 |
| 68 | 505.40 | 3.80 |
| 69 | 505.20 | 3.80 |
| 70 | 527.20 | 3.35 |
| 71 | 481.40 | 3.50 |
| 72 | 477.20 | 3.48 |
| 73 | 526.00 | 3.37 |
| 74 | 530.20 | 3.62 |
| 75 | 439.40 | 3.17 |
| 76 | 483.40 | 2.90 |
| 77 | 441.20 | 3.25 |
| 78 | 488.20 | 3.03 |
| 79 | 492.20 | 3.27 |
| 80 | 538.20 | 3.32 |
| 81 | 451.20 | 3.88 |
| 82 | 443.20 | 3.51 |
| 83 | 443.40 | 3.51 |
| 84 | 481.40 | 3.74 |
| 85 | 475.20 | 4.09 |
| 86 | 392.00 | 2.28 |
| 87 | 397.00 | 3.60 |
| 88 | 391.00 | 3.70 |
| 89 | 405.20 | 3.84 |
| 90 | 421.00 | 3.75 |
| 91 | 427.20 | 3.85 |
| 92 | 405.20 | 3.87 |
| 93 | 421.20 | 3.73 |
| 94 | 425.00 | 3.89 |
| 95 | 405.40 | 3.87 |
| 96 | 421.20 | 3.63 |
| 97 | 425.20 | 3.89 |
| 98 | 451.00 | 3.81 |
| 99 | 483.40 | 4.12 |
| 100 | 481.20 | 4.19 |

B) Assays for Detecting and Measuring ΔF508—CFTR Correction Properties of Compounds I) Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

| Solutions | |
|---|---|
| Bath Solution #1: (in mM) | NaCl 160, KCl 4.5, $CaCl_2$ 2, $MgCl_2$ 1, HEPES 10, pH 7.4 with NaOH. |
| Chloride-free bath solution: | Chloride salts in Bath Solution #1 are substituted with gluconate salts. |
| CC2-DMPE: | Prepared as a 10 mM stock solution in DMSO and stored at −20° C. |
| $DiSBAC_2(3)$: | Prepared as a 10 mM stock in DMSO and stored at −20° C. |

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hoursB) Electrophysiological Assays for assaying ΔF508-CFTR modulation properties of compounds 1. Ussing Chamber Assay Ussing chamber experiments were performed on polarized epithelial cells expressing ΔF508-CFTR to further characterize the ΔF508-CFTR modulators identified in the optical assays. $FRT^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

| Solutions | |
|---|---|
| Basolateral solution (in mM): | NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH. |
| Apical solution (in mM): | Same as basolateral solution with NaCl replaced with Na Gluconate (135). |

Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/mi penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

| Solutions | |
|---|---|
| Intracellular solution | Cs-aspartate (90), CsCl (50), MgCl$_2$ (1), HEPES (10), and 240 μg/ml amphotericin-B (pH adjusted to 7.35 with CsOH). |
| Extracellular solution (in mM): | N-methyl-D-glucamine (NMDG)-Cl (150), MgCl$_2$ (2), CaCl$_2$ (2), HEPES (10) (pH adjusted to 7.35 with HCl). |

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

| Solutions | |
|---|---|
| Extracellular solution (in mM): | NMDG (150), aspartic acid (150), CaCl$_2$ (5), MgCl$_2$ (2), and HEPES (10) (pH adjusted to 7.35 with Tris base). |
| Intracellular solution (in mM): | NMDG-Cl (150), MgCl$_2$ (2), EGTA (5), TES (10), and Tris base (14) (pH adjusted to 7.35 with HCl). |

Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters, particularly CFTR. In some embodiments, certain compounds depicted in Table 1 exhibit a relative modulating efficacy of greater than 30%.

The invention claimed is:
1. A compound of formula I:

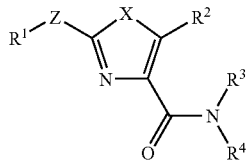

or a pharmaceutically acceptable salt thereof,
wherein X is S;
R$^1$ isphenyl, wherein R$^1$ is optionally substituted with x independent occurrences of —QR$^x$; wherein x is 0-5; wherein Q is a bond or is a C$_1$-C$_6$ alkylidene chain wherein up to two methylene units of Q are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and each occurrence of R$^x$ is independently R', halogen, NO$_2$, or CN, or —QR$^x$ is =O, =S, or =NR';
Z is —CH$_2$—;
each occurrence of R is independently hydrogen or C$_1$-C$_6$ aliphatic group; and each occurrence of R' is independently hydrogen or C1-C6 alkyl;
R$^2$ is halogen, —CN, —NO$_2$, or —T$_q$R;
R$^3$ is U$_m$R' and R$^4$ is V$_p$Cy$^1$,
wherein m is 0;
  p is 1;
  q is 0 or 1, and U, and T are each independently C$_1$-C$_4$alkylidene chain, wherein up to two methylene units of the chain are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—;
V is —CH$_2$C(R$^6$)$_2$— or —C(R$^6$)$_2$—;
R$^6$ is independently hydrogen, methyl, or two occurrences of R$^6$ on the same carbon are taken together to form a 3-6 membered ring selected from cyclopropyl, cyclobutyl, cyclopentyl, or cyclohexyl;
Cy$^1$ is a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein Cy$^1$ is optionally substituted at one or more carbon or nitrogen atoms with y independent occurrences of —WR$^W$; wherein y is 0-5; wherein W is a bond or is a C$_1$-C$_6$ alkylidene chain wherein up to two methylene units of W are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and
each occurrence of R$^W$ is independently R', halogen, NO$_2$, or CN, or —WRW is =O, =S, or =NR'; or provided that:
  a) when X is S; and R$^2$ is formyl, 4,5-dihydro-2-oxazolyl, —COOR', or COSR'; then:
    i) when Z is —CH$_2$—, R$^1$ is not phenyl optionally substituted with C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$haloalkylthio, halogen, cyano, or nitro;
  b) when X is S, R$^2$ is Sme or Me, Z is CH$_2$ and R$^1$ is unsubstituted phenyl,
    i) when R$^3$ is hydrogen, then R$^4$ is not unsubstituted benzyl; and
    ii) when R$^3$ is ethyl, then R$^4$ is not unsubstituted phenyl.

2. The compound of claim 1, wherein X is S and compounds of formula II-A are provided:

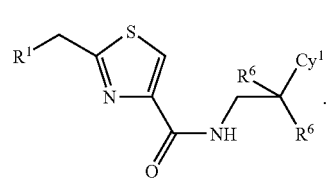

3. The compound of claim 1, wherein X is S and compounds of formula III-A are provided:

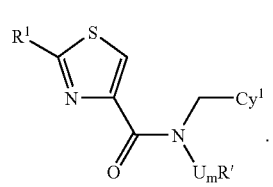

4. The compound according to claim 1, wherein said compound has formula VI-A:

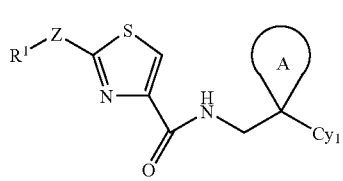

wherein ring A is cyclopropyl, cyclobutyl, cyclopentyl, or cyclohexyl.

5. The compound according to claim 4, wherein ring A is cyclopentyl or cyclohexyl.

6. The compound according to claim 1 or 4, wherein x is 0, 1, 2 or 3, and Q is a bond or C$_{1-6}$ alkylidene chain wherein one or two methylene units are optionally and independently replaced by O, NR, S, SO$_2$, or CO$_2$, CO, and R$^X$ is R' or halogen.

7. The compound according to claim 1 or 4, wherein y is 0-5 and W is a bond or is a C$_1$-C$_6$ alkylidene chain wherein up to two methylene units of W are optionally and independently replaced by —CO—, —CO$_2$—, —COCO—, —CONR—, —OCONR—, —NRNR—, —NRNRCO—, —NRCO—, —NRCO$_2$—, —NRCONR—, —SO—, —SO$_2$—, —NRSO$_2$—, —SO$_2$NR—, —NRSO$_2$NR—, —O—, —S—; or —NR—; and each occurrence of R$^W$ is independently R', halogen, NO$_2$, or CN, or —WR$^W$ is =O, =S, or =NR'.

8. The compound according to claim 7, wherein y is 0, 1, 2 or 3, and W is a bond or $C_{1-6}$ alkylidene chain wherein one or two methylene units are optionally and independently replaced by O, NR, S, $SO_2$, or $CO_2$, CO, and $R^W$ is R' or halogen.

9. The compound according to claim 8, wherein y is 0, 1, 2, or 3 and each occurrence of $WR^W$, when present, is independently —$C_{1-3}$alkyl, —O($C_{1-3}$alkyl), —$CF_3$, —$OCF_3$, —$SCF_3$, —F, —Cl, —Br, —COOR', —COR', —O($CH_2$)$_2$NI(R'), —O($CH_2$)NI(R'), —CONI(R'), —($CH_2$)$_2$OR', —($CH_2$)OR', phenyyl benzyl, —NI(R'), —($CH_2$)$_2$NI(R'), —($CH_2$)NI(R'), -or $SO_2$NRR'.

10. The compound according to claim 1 or 4, wherein $R^1$ is phenyl optionally substituted with up to three substituents selected from —$C_{1-3}$alkyl, —O($C_{1-3}$alkyl), —$CF_3$, —$OCF_3$, —$SCF_3$, —F, —Cl, —Br, —COOR', —COR', —O($CH_2$)$_2$NI(R'), —O($CH_2$)NI(R'), —CONI(R'), —($CH_2$)$_2$OR', —($CH_2$)OR', phenyl, benzyl, —NI(R'), —($CH_2$)$_2$NI(R'), —($CH_2$)NI(R'), -or $SO_2$NRR'.

11. A pharmaceutical composition comprising:
(i) a compound according to claim 1 or 4; and
(ii) a pharmaceutically acceptable carrier.

12. The compound according to claim 6, wherein x is 0, 1, 2, or 3 and each occurrence of $QR^x$, when present, is independently —$C_{1-3}$alkyl, —O($C_{1-3}$alkyl), —$CF_3$, —$OCF_3$, —$SCF_3$, —F, —Cl, —Br, —COOR', —COR', —O($CH_2$)$_2$NI(R'), —O($CH_2$)NI(R'), —CONI(R'), —($CH_2$)$_2$OR', —($CH_2$)OR', phenyl, benzyl, —NI(R'), —($CH_2$)$_2$NI(R'), —($CH_2$)NI(R'), -or $SO_2$NRR'.

13. The compound according claim 1 or 4, wherein $Cy^1$ is selected from one of the following rings:

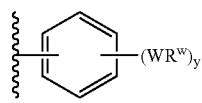
i

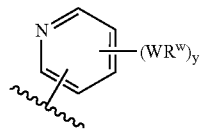
ii

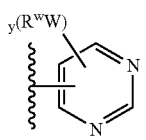
iii

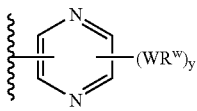
iv

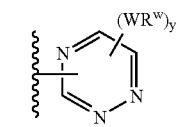
v

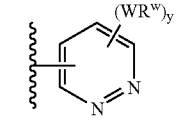
vi

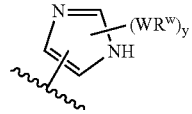
vii

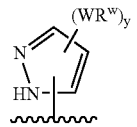
viii

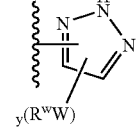
ix

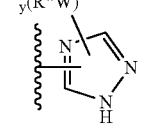
x

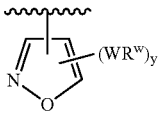
xi

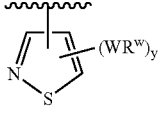
xii

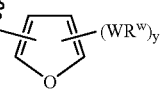
xiii

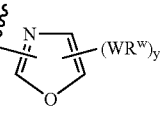
xiv

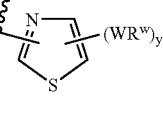
xv

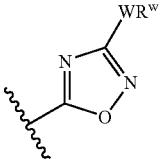
xvi

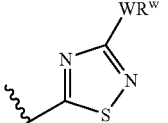
xvii

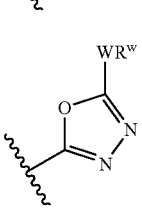
xviii

-continued
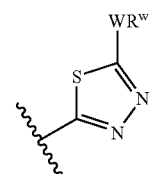 xix
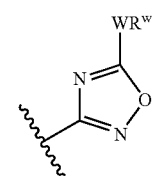 xx
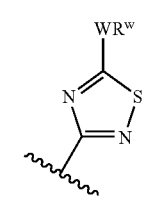 xxi
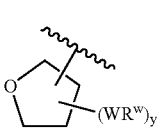 xxii
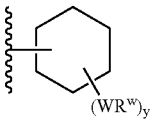 xxiii
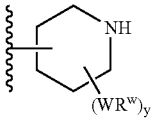 xxiv
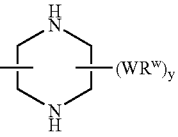 xxv
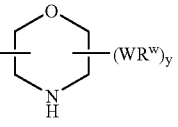 xxvi
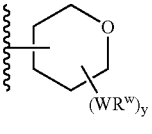 xxvii
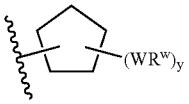 xxviii
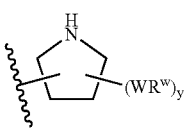 xxix
-continued
 xxx
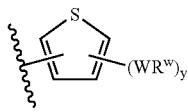 xxxi
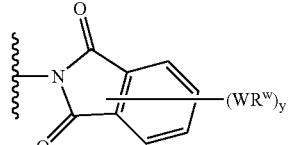 xxxii
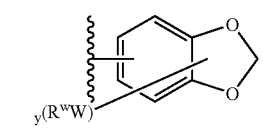 xxxiii
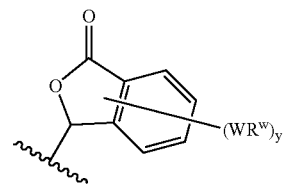 xxxiv
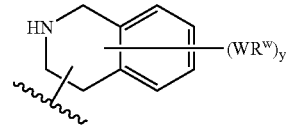 xxxv
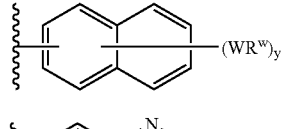 xxxvi
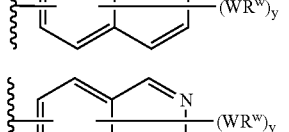 xxxvii
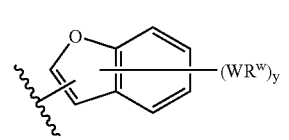 xxxviii
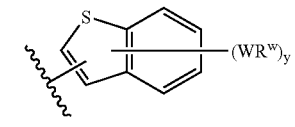 xxxix
xL
xLi -continued
xLii 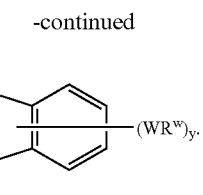
xLiii
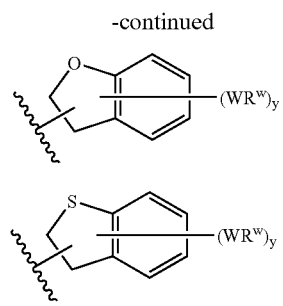
-continued
xLiv
14. The compound according to claim 1, wherein said compound is selected from Table 1 below:
TABLE 1
| Cmpd # | Compound |
| --- | --- |
| 32 | |
| 33 | |
| 36 | |

TABLE 1-continued

| Cmpd # | Compound |
|---|---|
| 37 | |
| 40 | |
| 41 | |
| 51 | |

TABLE 1-continued
| Cmpd # | Compound |
|---|---|
| 52 | 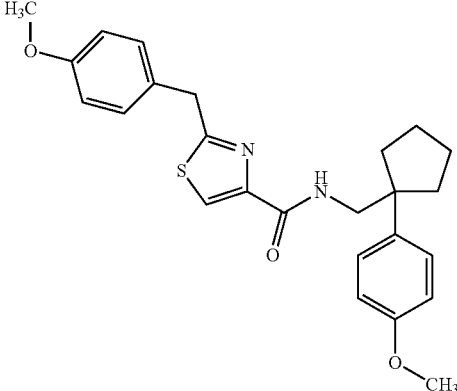 |
| 53 | 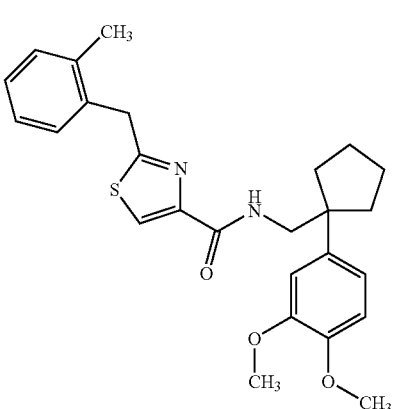 |
| 54 | 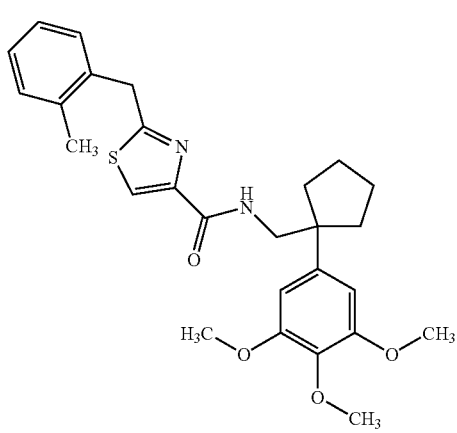 |
| 55 | 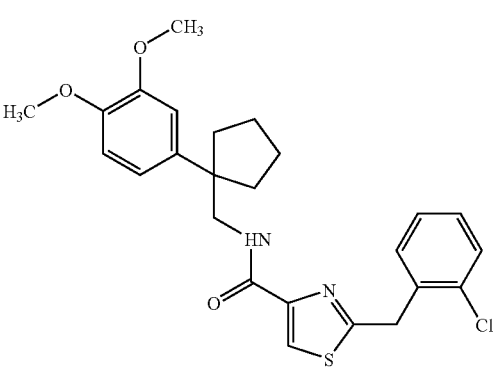 |

TABLE 1-continued
| Cmpd # | Compound |
|---|---|
| 56 | 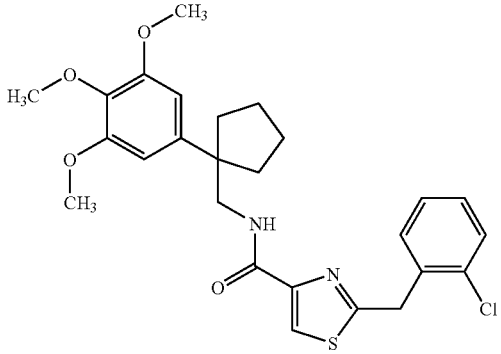 |
| 57 | 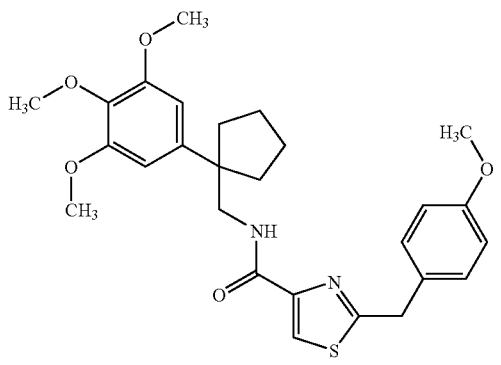 |
| 58 | 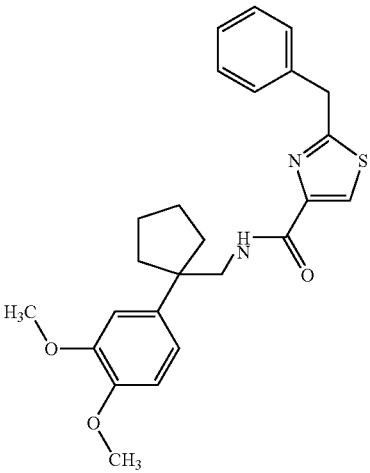 |
| 59 | 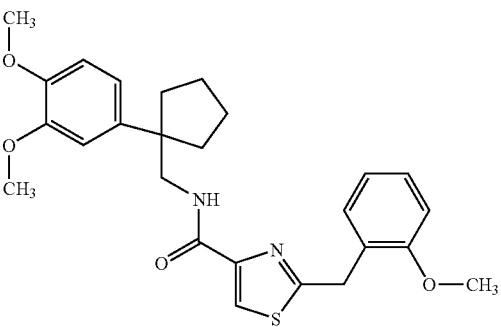 |

TABLE 1-continued
| Cmpd # | Compound |
|---|---|
| 60 | 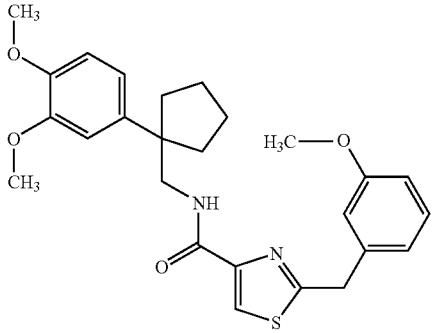 |
| 61 | 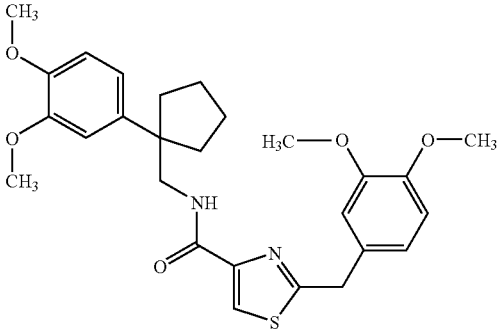 |
| 62 | 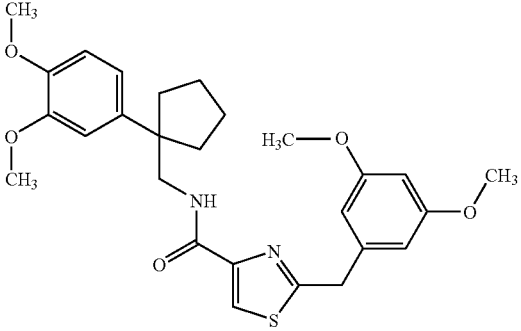 |
| 63 | 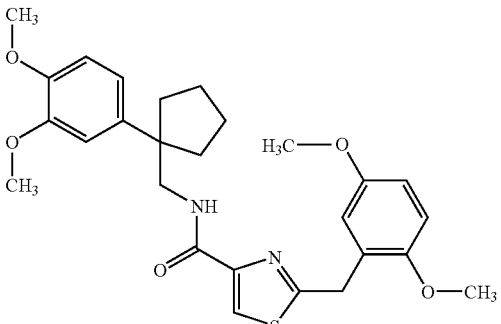 |

TABLE 1-continued
| Cmpd # | Compound |
|---|---|
| 64 | 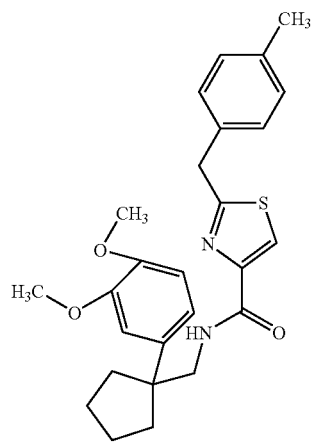 |
| 65 | 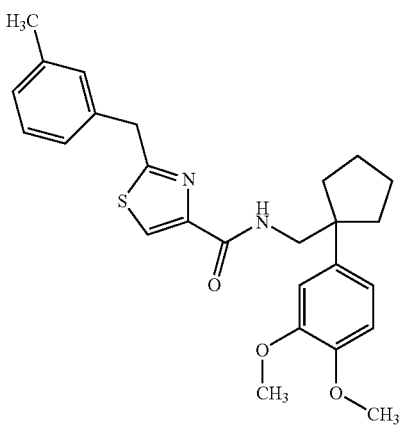 |
| 66 | 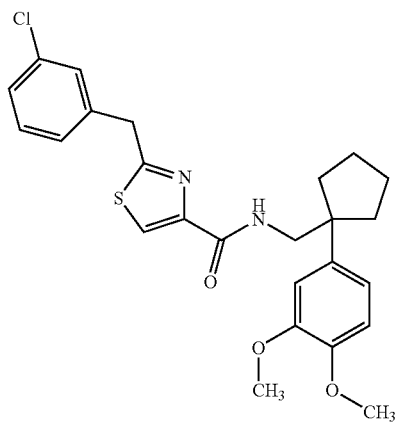 |

TABLE 1-continued
| Cmpd # | Compound |
|---|---|
| 67 | 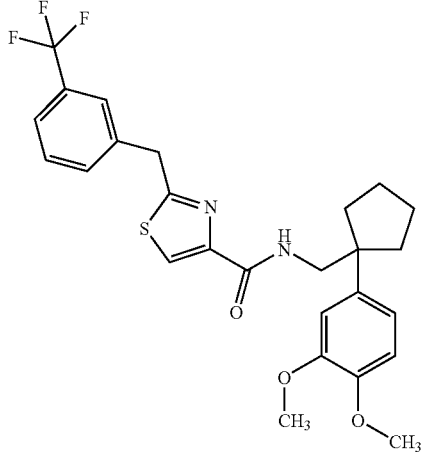 |
| 68 | 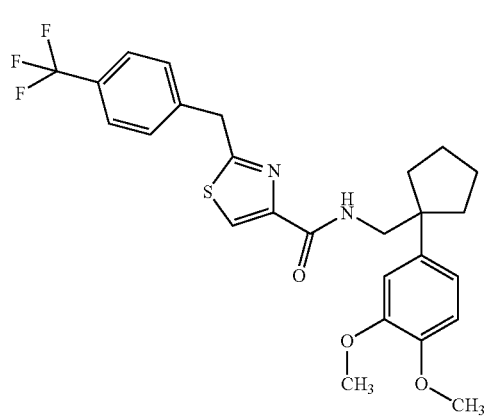 |
| 69 | 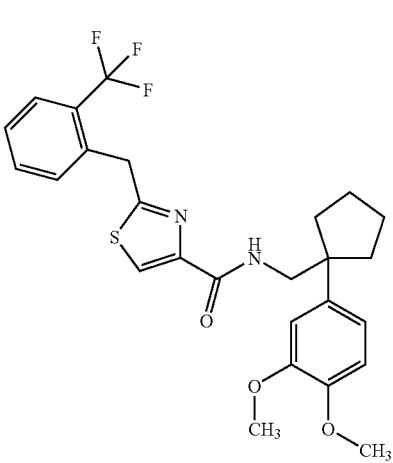 |

TABLE 1-continued
| Cmpd # | Compound |
|---|---|
| 70 | 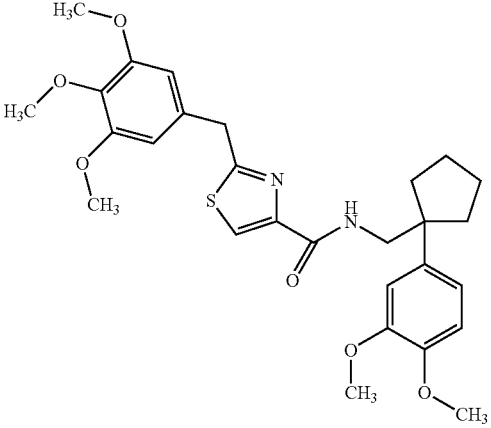 |
| 71 | 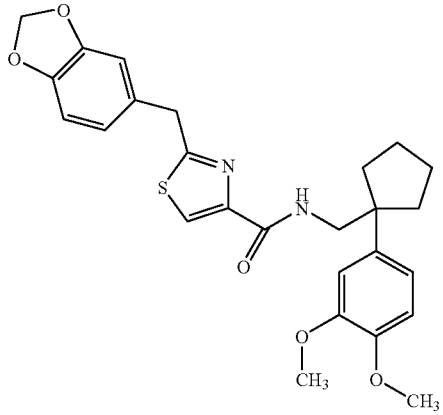 |
| 72 | 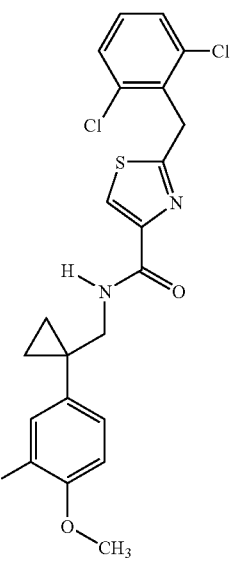 |

TABLE 1-continued
| Cmpd # | Compound |
|---|---|
| 75 | 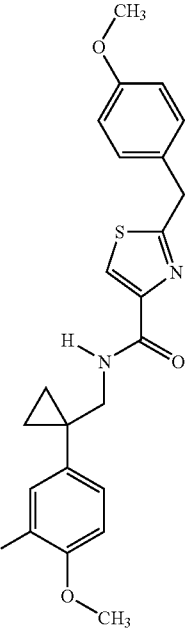 |
| 84 | 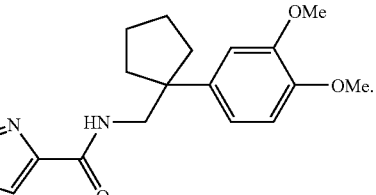 |
15. The compound according to claim 13, wherein $Cy_1$ is ring I or ring xxxiii.
* * * * *

UNITED STATES PATENT AND TRADEMARK OFFICE
CERTIFICATE OF CORRECTION

PATENT NO.         : 7,407,976 B2                                        Page 1 of 1
APPLICATION NO. : 10/989218
DATED              : August 5, 2008
INVENTOR(S)        : Mark T. Miller et al.

It is certified that error appears in the above-identified patent and that said Letters Patent is hereby corrected as shown below:

In column 169, claim 15, line 41, "ring I" should be --ring i--.

Signed and Sealed this

Twenty-first Day of October, 2008

JON W. DUDAS
*Director of the United States Patent and Trademark Office*